US007671254B2

(12) United States Patent
Tranel et al.

(10) Patent No.: US 7,671,254 B2
(45) Date of Patent: Mar. 2, 2010

(54) HERBICIDE RESISTANCE GENE, COMPOSITIONS AND METHODS

(75) Inventors: Patrick Tranel, Ogden, IL (US); Aaron Hager, Saint Joseph, IL (US); William Patzoldt, Roedersheim-Gronau (DE)

(73) Assignee: The Board of Trustees of the University of Illinois, Urbana, IL (US)

( * ) Notice: Subject to any disclaimer, the term of this patent is extended or adjusted under 35 U.S.C. 154(b) by 655 days.

(21) Appl. No.: 11/466,662

(22) Filed: Aug. 23, 2006

(65) Prior Publication Data

US 2007/0050863 A1 Mar. 1, 2007

Related U.S. Application Data

(60) Provisional application No. 60/711,204, filed on Aug. 25, 2005, provisional application No. 60/807,780, filed on Jul. 19, 2006.

(51) Int. Cl.
*A01H 5/00* (2006.01)
*C07H 21/04* (2006.01)
*C12N 5/04* (2006.01)

(52) U.S. Cl. ....................... 800/300; 800/306; 800/312; 800/314; 800/317.4; 800/322; 536/23.2; 435/320.1; 435/419; 530/370

(58) Field of Classification Search ....................... None
See application file for complete search history.

(56) References Cited

U.S. PATENT DOCUMENTS

| | | | | |
|---|---|---|---|---|
| 4,746,352 | A | 5/1988 | Wenger et al. | |
| 5,183,492 | A | 2/1993 | Suchy et al. | |
| 5,405,829 | A | 4/1995 | Hatfiel et al. | |
| 5,451,513 | A | 9/1995 | Maliga et al. | |
| 5,545,817 | A | 8/1996 | McBride et al. | |
| 5,545,818 | A | 8/1996 | McBride et al. | |
| 5,731,181 | A * | 3/1998 | Kmiec | 435/6 |
| 5,877,462 | A | 3/1999 | Chenais | |
| 5,939,602 | A | 8/1999 | Volrath et al. | |
| 6,282,837 | B1 | 9/2001 | Ward et al. | |
| 6,808,904 | B2 | 10/2004 | Ward et al. | |

FOREIGN PATENT DOCUMENTS

| | | |
|---|---|---|
| WO | WO 9310100 A1 | 5/1993 |
| WO | WO 9408999 A1 | 4/1994 |
| WO | WO 9516783 A1 | 6/1995 |
| WO | WO 9732977 A1 | 9/1997 |
| WO | WO 0183459 A2 | 11/2001 |

OTHER PUBLICATIONS

Maughan et al., Database Uniprot_14.6, Sep. 11, 2008. Attached to office action.*

Moore et al., Abstracts of the Weed Science Society of America (1993) 33:9.

*Arabidopsis* Genome Initiative. (2000). Analysis of the genome sequence of the flowering plant *Arabidopsis thaliana*. Nature 408:796-815.

Bartlett et al. In: Edelmann et al. (Eds.) Methods in Chloroplast Molecular Biology, Elsevier, pp. 1081-1091, 1982.

Beale et al. 1990. Tetrapyrrole Metabolism In Photosynthetic Organisms In Biosynthesis of Heme and Chlorophylls (ed. By H.A. Dailey). McGraw-Hill, New York. pp. 287-391.

Camadro et al. 1982. A new Assay for Protoporphyrinogen Oxidase—Evidence for a Total Deficiency in that Activity in a Heme-Less Mutant of *Saccharomyces cerevisiae*. Biochem. Biophys. Res. Comm. 106: 724-730.

Chabregas et al. 2001. Dual Targeting Properties of the N-terminal Signal Sequence of *Araidopsis thaliana* THI1 Protein to Mitochondria and Chloroplasts. Plant Mol. Biol. 46:639-650.

Che et al. 1993. Localization of Target-Site of the Protoporphyrinogen Oxidase-Inhibiting Herbicide, S-23142, in *Spinacia oleracea* L. Z. Naturforsch. 48c: 350-355.

Che et al. 2000. Molecular Characterization and Subcellular Localization of Protoporphyrinogen Oxidase in Spinach Chloroplasts. Plant Physiol. 124:59-70.

Choi K. W. et al. 1998. Generation of Resistance to the Diphenyl Ether Hericde, Oxyfluorfen, via Expression of the *Bacillus subtilis* Protoporphyrinogen Oxidase Gene in Transgenic Tobacco Plants. Biosci. Biotech. Biochem. 62:558-560.

Chow, K. S. et al. 1997. A Single Precursor Protein for Ferrochelatase-I From *Arabidopsis* is Imported In Vitro Into Both Chloroplasts and Mitochondria. A J. Biol. Chem. 272:27565-27571.

Comai et al. 1985. Expression in Plants of a Mutant aroA gene from *Salmonella typhimurium* Confers Tolerance to Glyphosate Nature 317:741-744.

Comai et al. 1988. Chloroplast Transport of a Ribulose Biophosphate Carboxylase Small Subunit-5-Enolpyruvyl 3-Phosphoshikimate Synthase Chimeric Protein Requires Part of the Mature Small Subunit in Addition to the Transit Peptide. J. Biol. Chem. 263: 15104-15109.

Cox et al. 1983. Excited State Interactions of Protoporphyrin IX and Related Porphyrins with Molecular Oxygen In Solutions and Organized Assemblies, In Porphyrin Photosensitization (ed. by D. Kessel and T.J. Dougherty). Plenum Press, New York, NY.

Dailey et al. 1994. Expression of a Cloned Protoporphyrinogen Oxidase. J. Biol. Chem. 269: 813-815.

Dayan, et al. 1997. Phytotoxicity of Protoporphyrinogen Oxidase Inhibitors: Phenomenology, Mode of Action and Mechanisms of Resistance, In Herbicide Activity: Toxicology, Biochemistry and Molecular Biology (ed. by R.M. Roe, J.D. Burton and R.J. Kuhr) IOS Press, Amsterdam, Netherlands. pp. 11-36.

(Continued)

*Primary Examiner*—Eileen B O Hara
(74) *Attorney, Agent, or Firm*—Greenlee, Winner and Sullivan, P.C.

(57) ABSTRACT

The present disclosure provides methods, recombinant DNA molecules, recombinant host cells containing the DNA molecules, and transgenic plant cells, plant tissue, seeds and plants which contain and express an herbicide resistant protoporphyrinogen oxidase such that they germinate from seed and grow in the presence of an amount of herbicide where the parent plant does not. Such plants are especially appropriate for use in agriculture or horticulture where herbicides are used to kill undesirable plants which might contaminate or compete with the transgenic plant of interest.

26 Claims, 11 Drawing Sheets

OTHER PUBLICATIONS

Duke, S. O. et al. 1997. Mechanisms of Resistance to Protoporphyrinogen Oxidase-Inhibiting Herbicides In Weed and Crop Resistance to Herbicides (ed. by R. De Prado, J. Jorrín, and L. García-Torres). Kluwer Academic Publishers. Netherlands. pp. 155-160.

Duke et al. 1991. Protoporphyrinogen Oxidase-Inhibiting Herbicides. Weed Sci. 39: 465-473.

Emanuelsson, et al. 2000. Predicting Subcellular Localization of Proteins Based on their N-terminal Amino Acid Sequence. J. Mol. Biol. 300:1005-1016.

Roder et al. 1994. Efficiency of the Tetracycline-Dependent Gene Expression System: Complete Suppression and Efficient Induction of the ro IB Phenotype in Transgenic Plants. Mol. Gen. Genetics 243:32-38.

Gordon-Kamm et al. 1990. Transformation of Maize Cells and Regeneration of Fertile Transgenic Plants. Plant Cell 2:603-618.

Ha et al. 2004. The Plastidic *Arabidopsis* Protoporphyrinogen IX Oxidase Gene, With or Without the Transit Sequence, Confers Resistance to the Diphenyl Ether Herbicide in Rice. Plant Cell Environ. 27: 79-88.

Harley and Reynolds. 1987. Analysis of *E. coli* Promoter Sequences. Nucleic Acids Res. 15:2343-2361.

Gatz et al. 1991. Regulation of a Modified CaMV 35S Promoter by the Tn*10*-Encoded Tet Repressor in Transgenic Tobacco. Mol. Gen. Genetics 227:229-237.

Hinchee et al. 1988. Production of Transgenic Soybean Plants Using *Agrobacterium*-Mediated DNA Transfer. Bio/Technology 6:915-922.

Horikoshi, M. and T. Hirooka. 1999. Selection of Tobacco Cell Lines Resistant to Photobleaching Hericides. Pestic. Sci. 24:13-16.

Horikoshi, M., K. et al. Jan. 5, 1999. *Nicotiana tabacum* Protoporphyrinogen Oxidase PX-2 mRNA. GenBank Accession No. AF044129.

Jackson and Moore, in Plant Organelles, Reid, ed., pp. 1-12.

Jacobs and Jacobs. 1982. Assay for Enzymatic Protoporphyrinogen Oxidation, a Late Step in Heme Synthesis. Enyzme 28: 206-219.

Jacobs, J. M. and N. J. Jacobs. 1984. Protoporphyrinogen Oxidation, an Enzymatic Step in Heme and Chlorophyll Synthesis: Partial Characterization of the Reaction in Plant Organelles and Comparison with Mammalian and Bacterial Systems. Arch. Biochem. Biophys. 229:312-319.

Jacobs, J. M. and N. J. Jacobs. 1993. Porphyrin Accumulation and Export by Isolated Barley (*Hordeum vulgare*) Plastids. Plant Physiol. 101:1181-1187.

Johnson, D. J., et al. Apr. 15, 2005. *Solanum tuberosum*, Cultivar Binje, mRNA for Ferrochelatase. GenBank assession AJ005802.

Johnson, D. J., et al. Feb. 9, 1999. *Solanum tuberosum* (*Cultivar bintje*) Cholorplastid Protoporphyrinogen IX Oxidase. GenBank accession AJ225107.

Johnson, D.J., et al. Apr. 10, 2000. *Solanum tuberosum* (*Cultivar bintje*) Mitochondrial Protoporphyrinogen IX Oxidase. GenBank accession AJ225108.

Jung et al. 2004. Dual Targeting of *Myxococcus xanthus* Protoporphyrinogen Oxidase into Choloroplasts and Mitochondria and High Level Oxyfluorfen Resistance. Plant Cell Environ. 27, 1436-1446.

Kashi, Y. and King, D. G. 2006. Simple Sequence Repeats as Advantageous Mutators in Evolution. Trends Genetics 22: 253-259.

Kataoka et al. 1990. Isolation and Partial Characterization of Mutant *Chlamydomonas reinhardtii* Resistant to Herbicide S-23142. J. Pesticide Sci. 15: 449-451.

Koch et al. 2004. Crystal Structure of Protoporphyrinogen IX Oxidase: A Key Enzyme in Haem and Chlorophyll Biosynthesis. EMBO 23:1720-1728.

Koehler and Ho. 1990. Hormonal Regulation, Processing, and Secretion of Cysteine Proteinases in Barley Aleurone Layers. Plant Cell 2: 769-783.

Lee, H. J. and S. O. Duke. 1994. Protoporphyrinogen IX-Oxidizing Activities Involved in the Mode of Action of Peroxidizing Herbicides. J. Agric. Food Chem. 42:2610-2618.

Lee, H. J. et al. 1993. Cellular Localization of Protoporphyrinogen—Oxidizing Activities of Etiolated Barley (*Hordeum vulgare* L.) Leaves. Plant Physiol. 102:881-889.

Lee, H. J. et al. 2000. Transgenic Rice Plants Expressing a *Bacillus subtilis* Protoporphyrinogen Oxidase Gene are Resistant to Diphenyl Ether Herbicide Oxyfluorfen. Plant Cell Physiol. 41:743-749.

Lee, Y., Jung, S., and Back, K. (2004) Expression of Human Protoporphyrinogen Oxidase in Transgenic Rice Induces Both a Photodynamic Response and Oxyfluorfen Resistance. Pestic. Biochem. Physiol. 80, 65-74.

Lermontova, I. and B. Grimm. 2000. Overexpression of Plastidic Protoporphyrinogen IX Oxidase Leads to Resistance to The Diphehyl-Ether Herbicide Acifluorfen. Plant Physiol. 122:75-83.

Lermontova, I. et al. 1997. Cloning and Characterization of a Plastidal and a Mitochondrial Isoform of Tobacco Protoporphyrinogen IX Oxidase. PNAS 94:8895-8900.

Li et al. 2004. Physiological basis for Resistance to Diphenyl Ether Herbicides in Common Waterhemp (*Amaranthus rudis*) Weed Sci. 52: 333-338.

Li, X. and D. Nicholl. 2005. Development of PPO Inhibitor-Resistant Cultures and Crops. Pest Manag. Sci. 61:277-285.

Li et al. 2003. Development of Protoporphyrinogen Oxidase As An Efficient Selection Marker for *Agrobacterium tumefaciens*-Mediated Transformation of Maize. Plant Physiol. 133:736-747.

Lyga et al. 1994. Synthesis Mechanism of Action, and QSAR of Herbicidal 3-Substituted-2-aryl-4.5.6.7-tetrahydroindazoles. Pesticide Sci. 42:29-36.

Martz, E. 2002. Protein Explorer: Easy Yet Powerful Macromolecular Visualization. Trends Biochem. Sci. 27: 107-109.

Matringe et al. 1989. Protoporphyrinogen Oxidase as a Molecular Target for Diphenyl Ether Hericides. Biochem. J. 260: 231-235.

Matringe et al. 1989. Protoporphyrinogen Oxidase Inhibition by Three Peroxidizing Herbicides: Oxidation, LS 82-556 and M&B 39279. FEBS Lett. 245: 35-38.

Matringe, M. et al. 1992. Localization Within Chloroplasts of Protoporphyrinogen Oxidase, The Target Enzyme for Diphenylether-Like Herbicides. J. Biol. Chem. 267:4646-4651.

McBride et al. 1994. Controlled Expression of Plastid Transgenes in Plants Based on a Nuclear DNA-encoded and Plastid-Targeted T7 RNA Polymerase. Proc. Natl. Acad. Sci. USA 91: 7301-7305.

Nandihalli et al. 1992. Quantitative Structure—Activity Relationships of Protoporphyrinogen Oxidase-inhibiting Diphenyl Ether Herbicides. Pesticide Biochem. Physiol. 43: 193-211.

Narita, S. et al. 1996. Molecular Cloning and Characterization of a cDNA that Encodes Protoporphyrinogen Oxidase of *Arabidopsis thaliana*. Gene 182:169-175.

Oshio et al. 1993. Isolation and Characterization of a *Chlamydomonas reinhardtii* Mutant Resistant to Photobleaching Herbicides. Z. Naturforsch. 48c: 339-344.

Papenbrock, J. and B. Grimm. 2001. Regulatory Network of Tetrapyrrole Biosynthesis—Studies of Intracellular Signalling Involved in Metabolic and Developmental Control of Plastids. Planta 213:667-681.

Patzold et al. 2002. Variable Herbicide Responses Among Illinois Waterhemp (*Amaranthus rudis* and *A. tuberculatus*) Populations. Crop Prot. 21:707-712.

Patzoldt et al. 2005. A Waterhemp (*Amaranthus tuberculatus*) Biotype with Multiple Resistance Across Three Herbicide Sites of Action. Weed Sci. 53:30-36.

Patzoldt et al. 2001. A Common Ragweed Population Resistant to Cloransulam-Methyl. Weed Sci. 49: 485-490.

Patzoldt et al. 2006. A Codon Deletion Confers Resistance to Herbicides Inhibiting Protoporphyrinogen Oxidase. PNAS. 103:12329-12334.

Patzoldt, W.L., et al. Aug. 18, 2006. *Amaranthus tuberculatus* Biotype Herbicide-Susceptible WC Plastid Protoporphyrinogen Oxidase (PPX!) mRNA; Nuclear Gene for Plastid Product. NCBI GenBank accession DQ386112.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386113.

Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386114.
Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386115.
Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386116.
Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386117.
Patzoldt, W.L., et al. Aug. 18, 2006. *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ386118.
Patzoldt, W.L., et al. Aug. 18, 2006 *Amaranthus tuberculatus* Biotype Herbicide-Susceptible WC Plastid Protoporphyrinogen Oxidase (PPX1) mRNA; Nuclear Gene for Plastid Product. NCBI GenBank accession DQ394875.
Patzoldt, W.L., et al. Aug. 18, 2006. *Amaranthus tuberculatus* Biotype Herbicide-Susceptible WC Plastid Protoporphyrinogen Oxidase (PPX!) mRNA; Nuclear Gene for Plastid Product. NCBI GenBank accession DQ394876.
Pornprom, T. et al. 1994. Characterization of Oxyfluorfen Tolerance in Selected Soybean Cell Line. Pestic. Biochem. Physiol. 50:107-114.
Prado et al. 1979. ATP Requirement for Mg Chelatase in Developing Chloroplasts. Plant Physiol. 65: 956-960.
Retzlaff, K. and P. Böger. 1996. An Endoplasmic Reticulum Plant Enzyme Has Protoporphyrinogen IX Oxidase Activity. Pest. Biochem. Physiol. 54:105-114.
Roberts, et al. 1979. A General Method for Maximizing the Expression of a Cloned Gene. Proc. Natl. Acad. Sci. USA 76:760-764.
Rogers et al. 1985. Aleurain: A Barley Thiol Protease Closely Related to Mammalian Cathepsin H. Proc. Natl. Acad. Sci. USA 82: 6512-6516.
Sasarman, A. et al. 1993. Nucleotide Sequence of the *HemG* gene Involved in the Protoporphyrinogen Oxidase Activity of *Escherichia coli* K12. Can. J. Microbiol. 39:1155-1161.
Sasarman, A. et al. 1979. Mapping of a New *Hem* Gene in *Escherichia coli* K12. J. Gen. Microbiol. 113: 297-303.
Sato et al. 1994. Chapter 7—Characterization of a Mutant of *Chlamydomonas reinhardtii* Resistant to Protoporphyrinogen Oxidase Inhibitors. In ACS Symposium on Porphyric Pesticides, S. Duke, ed. ACS Press: Washington, DC.
Seefeldt, S. S. et al. 1995. Log-Logistic Analysis of Herbicide Dose-Response Relationships. Weed Technol. 9:218-227.
Sherman et al. 1991. Physiological Basis for Differential Sensitivities of Plant Species to Protoporphyrinogen Oxidase-Inhibiting Herbicides. Plant Physiol. 97:280-287.
Shibata et al. 1992. Isolation and Characterization of a *Chlamydomonas reinhardtii* Mutant Resistant to an Experimental Herbicide S-23142, Which Inhibits Chlorophyll Synthesis. In Research in Photosynthesis, vol. III, N. Murata, ed. Kluwer:Netherlands. pp. 567-570.
Shinshi et al. 1990. Structure of a Tobacco Endochitinase Gene: Evidence that Different Chitinase Genes can Arise by Transposition of Sequences Encoding a Cystein-Rich Domain. Plant Molec. Biol. 14: 357-368.
Shoup, D. E. and Al-Khatib, K. 2005. Fate of Acifluorfen and Lactofen in Common Waterhemp (*Amaranthus rudis*) Resistant to Protoporphyrinogen Oxidase-Inhibiting Herbicides. Weed Sci. 53: 284-289.
Shoup, D. E. et al. 2003. Common Waterhemp (*Amaranthus rudis*) Resistance to Protoporphyrinogen Oxidase-Inhibiting Herbicides. Weed Sci. 51:145-150.
Smith, A. G. et al. 1993. Investigation of the Subcellular Location of the Tetrapyrrole-Biosynthesis Enzyme Coproporphyrinogen Oxidase in Higher Plants. Biochem J. 292:503-508.
Stalker et al. 1988. Purification and Properties of a Nitrilase Specific For The Herbicide Bromoxynil and Corresponding Nucleotide Sequence Analysis Of The bxn Gene. J. Biol. Chem. 263:6310-6314.
Stalker et al. 1988. Herbicide Resistance in Transgenic Plants Expressing a Bacterial Detoxification Gene. Science. 242:419-423.
Staub et al. (1992) Long Regions of Homologous DNA Are Incorporated into the Tobacco Plastid Genome by Transformation. Plant Cell 4, 39-45.
Staub et al. 1993. Accumulation of D1 Polypeptide in Tobacco Plastids is Regulated Via the Untranslated Region of the *psbA* mRNAEMBO J. 12: 601-606.
Stone, B. F. 1968. A Formula for Determining Degree of Dominance In Cases of Monofactorial Inheritance of Resistance to Chemicals. Bull. W.H.O. 38:325-326.
Suggs, S.V. et al. 1981. Use of Synthetic Oligodeoxyribonucleotides for the Isolation of Specific Cloned DNA Sequences. ICB-UCLA Symp. Dev. Biol. Using Purified Genes, D.D. Brown (ed.), Academic Press, New York, 23:683-693.
Svab et al. 1990. Stable Transformation of Plastids in Higher Plants. Proc. Natl. Acad. Sci. USA 87: 8526-8530.
Svab et al. 1993. High-Frequency Plastid Transformation in Tobacco by Selection for a Chimeric aadA Gene. Proc. Natl. Acad. Sc. USA 90: 913-917.
Thompson et al. 1994. CLUSTAL W: Improving the Sensitivity of Progressive Multiple Sequence Alignment Through Sequence Weighting, Position-Specific Gap Penalties and Weight Matrix Choice Nucleic Acids Res. 22: 4673-4690.
Unger et al. 1989. Isolation of a cDNA Encoding Mitochondrial Citrate Synthase from *Arabidopsis thaliana*. Plant Molec. Biol. 13: 411-418.
van den Broeck et al. 1985. Targeting of a Foreign Protein to Chloroplasts by Fusion to the Transit Peptide From the Small Subunit of Ribulose 1, 5-Bisphosphate Carboxylase. Nature 313: 358-363.
Wasmann et al. 1986. The Importance of the Transit Peptide and the Transported Protein for Protein Import into Chloroplasts. Mol. Gen. Genet. 205: 446-453.
Watanabe, N. et al. 1998. Molecular Characterization of Photomixotrophic Tobacco Cells Resistant to Protoporphyrinogen Oxidase-Inhibiting Herbicides. Plant Physiol. 118:751-758.
Watanabe, N. et al. 2001. Dual Targeting of Spinach Protoporphyrinogen Oxidase II to Mitochondria and Chloroplasts by Alternative Use of Two In-Frame Initiation Codons. J. Biol. Chem. 276:20474-20481.
Written Opinion of the International Searching Authority for PCT/US06/32453.
Xu et al. 1992. The Genes Required for Heme Synthesis in *Salmonella typhimurium* Include Those Encoding Alternative Functions For Aerobic and Anaerobic Coproporphyrinogen Oxidation. J. Bacteriol. 174: 3953-3963.
Yanase and Andoh. 1989. Porphyrin Synthesis Involvement in Diphenyl Ether-Like Mode of Action of TNPP-Ethyl, A Novel Phenylpyrazole Herbicide. Pesticide Biochem. Physiol. 35: 70-80.
Yang, H. et al. 1996. Proc. Natl. Acad. Sci USA 93:2459-2463.

* cited by examiner

```
                1
S-WT            MVIQSITHLS PNLALPSPLS VSTKNYPVAV MGNISEREEP TSAKRVAVVG AGVSGLAAAY
S-BioAC         MVIQSITHLS PNLALPSPLS VSTKNYPVAV MGNISEREEP TSAKRVAVVG AGVSGLAAAY
R-BioAC         MVIQSITHLS PNLALPSPLS VSTKNYPVAV MGNISEREEP TSAKRVAVVG AGVSGLAAAY
R-BioCC         MVIQSITHLS PNLALPSPLS VSTKNYPVAV MGNISEREEP TSAKRVAVVG AGVSGLAAAY

                61             *
S-WT            KLKSHGLSVT LFEADSRAGG KLKTVKKDGF IWDEGANTMT ESEAEVSSLI DDLGLREKQQ
S-BioAC         KLKSHGLSVT LFEADSRAGG KLKTVKKDGF IWDEGANTMT ESEAEVSSLI DDLGLREKQQ
R-BioAC         KLKSHGLSVT LFEADSRAGG KLKTVKKDGF IWDEGANTMT ESEAEVSSLI DDLGLREKQQ
R-BioCC         KLKSHGLSVT LFEANSRAGG KLKTVKKDGF IWDEGANTMT ESEAEVSSLI DDLGLREKQQ

                121          *
S-WT            LPISQNKRYI ARDGLPVLLP SNPAALLTSN ILSAKSKLQI MLEPFLWRKH NATELSDEHV
S-BioAC         LPISQNKRYI ARAGLPVLLP SNPAALLTSN ILSAKSKLQI MLEPFLWRKH NATELSDEHV
R-BioAC         LPISQNKRYI ARDGLPVLLP SNPAALLTSN ILSAKSKLQI MLEPFLWRKH NATELSDEHV
R-BioCC         LPISQNKRYI ARDGLPVLLP SNPAALLTSN ILSAKSKLQI MLEPFLWRKH NATELSDEHV

                181                            *         *
S-WT            QESVGEFFER HFGKEFVDYV IDPFVAGTCQ GDPQSLSMHH TFPEVWNIEK RFGSVFAGLI
S-BioAC         QESVGEFFER HFGKEFVDYV IDPFVAGTCQ GDPQSLSMHH TFPEVWNIEK RFGSVFAGLI
R-BioAC         QESVGEFFER HFGKEFVDYV IDPFVAGTC- GDPQSLSMHH TFPEVWNIEK RFGSVFAGLI
R-BioCC         QESVGEFFER HFGKEFVDYV IDPFVAGTC- GDPQSLSMYH TFPEVWNIEK RFGSVFAGLI

                241
S-WT            QSTLLSKKEK GGENASIKKP RVRGSFSFQG GMQTLVDTMC KQLGEDELKL QCEVLSLSYN
S-BioAC         QSTLLSKKEK GGENASIKKP RVRGSFSFQG GMQTLVDTMC KQLGEDELKL QCEVLSLSYN
R-BioAC         QSTLLSKKEK GGENASIKKP RVRGSFSFQG GMQTLVDTMC KQLGEDELKL QCEVLSLSYN
R-BioCC         QSTLLSKKEK GGENASIKKP RVRGSFSFQG GMQTLVDTMC KQLGEDELKL QCEVLSLSYN

                301
S-WT            QKGIPSLGNW SVSSMSNNTS EDQSYDAVVV TAPIRNVKEM KIMKFGNPFS LDFIPEVTYV
S-BioAC         QKGIPSLGNW SVSSMSNNTS EDQSYDAVVV TAPIRNVKEM KIMKFGNPFS LDFIPEVTYV
R-BioAC         QKGIPSLGNW SVSSMSNNTS EDQSYDAVVV TAPIRNVKEM KIMKFGNPFS LDFIPEVTYV
R-BioCC         QKGIPSLGNW SVSSMSNNTS EDQSYDAVVV TAPIRNVKEM KIMKFGNPFS LDFIPEVTYV

                361
S-WT            PLSVMITAFK KDKVKRPLEG FGVLIPSKEQ HNGLKTLGTL FSSMMFPDRA PSDMCLFTTF
S-BioAC         PLSVMITAFK KDKVKRPLEG FGVLIPSKEQ HNGLKTLGTL FSSMMFPDRA PSDMCLFTTF
R-BioAC         PLSVMITAFK KDKVKRPLEG FGVLIPSKEQ HNGLKTLGTL FSSMMFPDRA PSDMCLFTTF
R-BioCC         PLSVMITAFK KDKVKRPLEG FGVLIPSKEQ HNGLKTLGTL FSSMMFPDRA PSDMCLFTTF

                421                                                         *
S-WT            VGGSRNRKLA NASTDELKQI VSSDLQQLLG TEDEPSFVNH LFWSNAFPLY GHNYDSVLRA
S-BioAC         VGGSRNRKLA NASTDELKQI VSSDLQQLLG TEDEPSFVNH LFWSNAFPLY GHNYDSVLRA
R-BioAC         VGGSRNRKLA NASTDELKQI VSSDLQQLLG TEDEPSFVNH LFWSNAFPLY GHNYDCVLRA
R-BioCC         VGGSRNRKLA NASTDELKQI VSSDLQQLLG TEDEPSFVNH LFWSNAFPLY GHNYDSVLRA

                481
S-WT            IDKMEKDLPG FFYAGNHKGG LSVGKAMASG CKAAELVISY LDSHIYVKMD EKTA
S-BioAC         IDKMEKDLPG FFYAGNHKGG LSVGKAMASG CKAAELVISY LDSHIYVKMD EKTA
R-BioAC         IDKMEKDLPG FFYAGNHKGG LSVGKAMASG CKAAELVISY LDSHIYVKMD EKTA
R-BioCC         IDKMEKDLPG FFYAGNHKGG LSVGKAMASG CKAAELVISY LDSHIYVKMD EKTA
```

FIG. 7

| | Reference Sequence SEQ ID NO:15 | SEQ ID NO:21 | Additional Sensitive PPX2L Isolate | SEQ ID NO:27 | "pBAD" Sensitive | SEQ ID NO:46 | Synthetic (Sensitive) | Synthetic (Resistant) | Additional Synthetic (Resistant) |
|---|---|---|---|---|---|---|---|---|---|
| Difference | | A to C @ 66 | | | | | A to C @ 66 | A to C @ 66 | A to C @ 66 |
| AA Change | | none | | | | | none* | none* | none* |
| Difference | | | | | | | G to A @111 | G to A @111 | G to A @111 |
| AA Change | | | | | | | none* | none* | none* |
| Difference | | | | A to C @398 | | | | | |
| AA Change | | | | D to A | | | | | |
| Difference | | | | C to T @ 603 | | | C to T @ 603 | C to T @ 603 | C to T @ 603 |
| AA Change | | | | none | | | none* | none* | none* |
| Difference | | | | | G to A @ 641 | G to A @ 641 | | | |
| AA Change | | | | | Q to R | Q to R | | | |
| Difference | | | | T to C @711 | | | | | |
| AA Change | | | | none | | | | | |
| Difference | | | | T to C @919 | | | | | |
| AA Change | | | | none | | | | | |
| Difference | | | | | A to G @ 1016 | | | | |
| AA Change | | | | | E to G | | | | |
| Difference | | | | | | | | C to T @ 1272 | C to T @ 1272 |
| AA Change | | | | | | | | none | none |
| Difference | | | | | | | C to G @ 1427 | C to G @ 1427 | C to G @ 1427 |
| AA Change | | | | | | | S to C* | S to C* | S to C* |
| Difference | | | | | | | | T to C @ 1461 | T to C @ 1461 |
| AA Change | | | | | | | | none | none |
| Difference | | | | | | | | | A to G at 1571 |
| AA Change | | | | | | | | | H to R** |
| Difference | | | T to C @ 1578 | T to C @ 1578 | T to C @ 1578 | T to C @ 1578 | T to C @ 1578 | T to C @ 1578 | T to C @ 1578 |
| AA Change | | | none | none | none | none | none | none | none |

* synthesized clone was made to match Resistant allele at these spots

FIG. 10A

| | Reference Sequence SEQ ID NO:13 | SEQ ID NO:25 | SEQ ID NO:21 | Additional Isolate | "pBAD" Resistant | Additional Isolate | SEQ ID NO:45 | Additional Isolate | Additional Isolate |
|---|---|---|---|---|---|---|---|---|---|
| Difference | | A to C @ 66 | A to C @ 66 | A to C @ 66 | | A to C @ 66 | A to C @ 66 | A to C @ 66 | A to C @ 66 |
| AA Change | | none | none | none | | none | none | none | none |
| Difference | | G to A @ 111 | | | | G to A @ 111 | | G to A @ 111 | G to A @ 111 |
| AA Change | | none | | | | none | | none | none |
| Difference | | | G to A @ 223 | | | | | | |
| AA Change | | | D to N | | | | | | |
| Difference | | C to T @ 603 | C to T @ 603 | | C to T @ 603 | C to T @ 603 | C to T @ 603 | C to T @ 603 | C to T @ 603 |
| AA Change | | none | none | | none | none | none | none | none |
| Difference | | | | | C to T @ 652 | | | | |
| AA Change | | | | | H to Y | | | | |
| Difference | | | | | | | | C to T @ 1269 | |
| AA Change | | | | | | | | None | |
| Difference | | C to G @ 1424 | | | | C to G @ 1424 | | C to G @ 1424 | C to G @ 1424 |
| AA Change | | S to C | | | | S to C | | S to C | S to C |
| Difference | | | | | | | | T to C @ 1458 | |
| AA Change | | | | | | | | None | |
| Difference | | | | | | | | | A to G at 1568 |
| AA Change | | | | | | | | | H to R** |
| Difference | | T to C @ 1575 | T to C @ 1575 | | T to C @ 1575 | T to C @ 1575 | T to C @ 1575 | T to C @ 1575 | T to C @ 1575 |
| AA Change | | none | none | | none | none | none | none | none |

NB the deletion that causes tolerance is a deletion base 628-630 in the wild-type, a glycine codon.

** not all clones carried this mutation, nor did the parent CDS only clone; it was caused by cloning or E. coli

FIG. 10B

SEQUENCE LISTING

```
<160> NUMBER OF SEQ ID NOS: 54

<210> SEQ ID NO 1
<211> LENGTH: 22
<212> TYPE: DNA
<213> ORGANISM: Artificial
<220> FEATURE:
<223> OTHER INFORMATION: Synthetic:  oligonucleotide useful as primer.

<400> SEQUENCE: 1

gagagagtgc gagagagatg ag                                              22


<210> SEQ ID NO 2
<211> LENGTH: 23
<212> TYPE: DNA
<213> ORGANISM: Artificial
<220> FEATURE:
<223> OTHER INFORMATION: Synthetic:  oligonucleotide useful as primer

<400> SEQUENCE: 2

caagatgctg gagccctatt gac                                             23


<210> SEQ ID NO 3
<211> LENGTH: 22
<212> TYPE: DNA
<213> ORGANISM: Artificial
<220> FEATURE:
<223> OTHER INFORMATION: Synthetic:  oligonucleotide useful as primer

<400> SEQUENCE: 3

gccatcgcca ttgtcagttt ac                                              22


<210> SEQ ID NO 4
<211> LENGTH: 24
<212> TYPE: DNA
<213> ORGANISM: Artificial
<220> FEATURE:
<223> OTHER INFORMATION: Synthetic:  oligonucleotide useful as primer

<400> SEQUENCE: 4
```

-continued gaattacgcg gtcttctcat ccat 24

<210> SEQ ID NO 5
<211> LENGTH: 25
<212> TYPE: DNA
<213> ORGANISM: Artificial
<220> FEATURE:
<223> OTHER INFORMATION: Synthetic: oligonucleotide useful as primer

<400> SEQUENCE: 5
gacaaaattg gattcagaat ttagc 25

<210> SEQ ID NO 6
<211> LENGTH: 24
<212> TYPE: DNA
<213> ORGANISM: Artificial
<220> FEATURE:
<223> OTHER INFORMATION: Synthetic: oligonucleotide useful as primer

<400> SEQUENCE: 6
gaattacgcg gtcttctcat ccat 24

<210> SEQ ID NO 7
<211> LENGTH: 21
<212> TYPE: DNA
<213> ORGANISM: Artificial
<220> FEATURE:
<223> OTHER INFORMATION: Synthetic: oligonucleotide useful as primer

<400> SEQUENCE: 7
tgataagtcg ctcaatggag a 21

<210> SEQ ID NO 8
<211> LENGTH: 21
<212> TYPE: DNA
<213> ORGANISM: Artificial
<220> FEATURE:
<223> OTHER INFORMATION: Synthetic: oligonucleotide useful as primer

<400> SEQUENCE: 8
agatttgtag cacctccaat g 21

<210> SEQ ID NO 9
<211> LENGTH: 21
<212> TYPE: DNA
<213> ORGANISM: Artificial
<220> FEATURE:
<223> OTHER INFORMATION: Synthetic: oligonucleotide useful as primer

<400> SEQUENCE: 9
aagagacctc ttgagggctt c 21

<210> SEQ ID NO 10
<211> LENGTH: 24
<212> TYPE: DNA
<213> ORGANISM: Artificial
<220> FEATURE:
<223> OTHER INFORMATION: Synthetic: oligonucleotifde useful as primer

<400> SEQUENCE: 10
gaattacgcg gtcttctcat ccat 24

<210> SEQ ID NO 11
<211> LENGTH: 30
<212> TYPE: DNA

-continued

<213> ORGANISM: Artificial
<220> FEATURE:
<223> OTHER INFORMATION: Synthetic: oligonucleotide useful as primer

<400> SEQUENCE: 11
caggaataag taatgggcaa catttctgag 30

<210> SEQ ID NO 12
<211> LENGTH: 24
<212> TYPE: DNA
<213> ORGANISM: Artificial
<220> FEATURE:
<223> OTHER INFORMATION: Synthetic: oligonucleotide useful as primer

<400> SEQUENCE: 12
gaagaattac gcggtcttct catc 24

<210> SEQ ID NO 13
<211> LENGTH: 1602
<212> TYPE: DNA
<213> ORGANISM: Amaranthus tuberculatus

<400> SEQUENCE: 13
atggtaattc aatccattac ccacctttca ccaaaccttg cattgccatc gccattgtca 60
gtttcaacca agaactaccc agtagctgta atgggcaaca tttctgagcg ggaagaaccc 120
acttctgcta aaagggttgc tgttgttggt gctggagtta gtggacttgc tgctgcatat 180
aagctaaaat cccatggttt gagtgtgaca ttgtttgaag ctgattctag agctggaggc 240
aaacttaaaa ctgttaaaaa agatggtttt atttgggatg agggggcaaa tactatgaca 300
gaaagtgagg cagaggtctc gagtttgatc gatgatcttg ggcttcgtga gaagcaacag 360
ttgccaattt cacaaaataa aagatacata gctagagacg gtcttcctgt gctactacct 420
tcaaatcccg ctgcactact cacgagcaat atcctttcag caaaatcaaa gctgcaaatt 480
atgttggaac catttctctg gagaaaacac aatgctactg aactttctga tgagcatgtt 540
caggaaagcg ttggtgaatt ttttgagcga cattttggga aagagtttgt tgattatgtt 600
atcgaccctt ttgttgcggg tacatgtgga gatcctcaat cgctttccat gcaccataca 660
tttccagaag tatggaatat tgaaaaaagg tttggctctg tgtttgctgg actaattcaa 720
tcaacattgt tatctaagaa ggaaaagggt ggagaaaatg cttctattaa gaagcctcgt 780
gtacgtggtt cattttcatt tcaaggtgga atgcagacac ttgttgacac aatgtgcaaa 840
cagcttggtg aagatgaact caaactccag tgtgaggtgc tgtccttgtc atataaccag 900
aaggggatcc cctcattagg gaattggtca gtctcttcta tgtcaaataa taccagtgaa 960
gatcaatctt atgatgctgt ggttgtcact gctccaattc gcaatgtcaa agaaatgaag 1020
attatgaaat ttggaaatcc attttcactt gactttattc cagaggtgac gtacgtaccc 1080
ctttccgtta tgattactgc attcaaaaag gataaagtga agagacctct tgagggcttc 1140
ggagttctta tcccctctaa agagcaacat aatggactga agactcttgg tactttattt 1200
tcctccatga tgtttcctga tcgtgctcca tctgacatgt gtctctttac tacatttgtc 1260
ggaggaagca gaaatagaaa acttgcaaac gcttcaacgg atgaattgaa gcaaatagtt 1320
tcttctgacc ttcagcagct gttgggcact gaggacgaac cttcatttgt caatcatctc 1380
ttttggagca acgcattccc attgtatgga cacaattacg attctgtttt gagagccata 1440
gacaagatgg aaaaggatct tcctggattt ttttatgcag gtaaccataa gggtggactt 1500
tcagtgggaa aagcgatggc ctccggatgc aaggctgcgg aacttgtaat atcctatctg 1560

-continued

```
gactctcata tatatgtgaa gatggatgag aagaccgcgt aa                    1602


<210> SEQ ID NO 14
<211> LENGTH: 533
<212> TYPE: PRT
<213> ORGANISM: Amaranthus tuberculatus

<400> SEQUENCE: 14

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365
```

-continued

```
Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525

Asp Glu Lys Thr Ala
    530


<210> SEQ ID NO 15
<211> LENGTH: 1605
<212> TYPE: DNA
<213> ORGANISM: Amaranthus tuberculatus

<400> SEQUENCE: 15

atggtaattc aatccattac ccacctttca ccaaaccttg cattgccatc gccattgtca      60

gtttcaacca agaactaccc agtagctgta atgggcaaca tttctgagcg ggaagaaccc     120

acttctgcta aaagggttgc tgttgttggt gctggagtta gtggacttgc tgctgcatat     180

aagctaaaat cccatggttt gagtgtgaca ttgtttgaag ctgattctag agctggaggc     240

aaacttaaaa ctgttaaaaa agatggtttt atttgggatg agggggcaaa tactatgaca     300

gaaagtgagg cagaggtctc gagtttgatc gatgatcttg ggcttcgtga gaagcaacag     360

ttgccaattt cacaaaataa aagatacata gctagagacg gtcttcctgt gctactacct     420

tcaaatcccg ctgcactact cacgagcaat atcctttcag caaaatcaaa gctgcaaatt     480

atgttggaac catttctctg gagaaaacac aatgctactg aactttctga tgagcatgtt     540

caggaaagcg ttggtgaatt ttttgagcga cattttggga aagagtttgt tgattatgtt     600

atcgaccctt ttgttgcggg tacatgtggt ggagatcctc aatcgctttc catgcaccat     660

acatttccag aagtatggaa tattgaaaaa aggtttggct ctgtgtttgc tggactaatt     720

caatcaacat tgttatctaa gaaggaaaag ggtggagaaa atgcttctat taagaagcct     780

cgtgtacgtg gttcattttc atttcaaggt ggaatgcaga cacttgttga cacaatgtgc     840

aaacagcttg gtgaagatga actcaaactc cagtgtgagg tgctgtcctt gtcatataac     900

cagaagggga tcccctcatt agggaattgg tcagtctctt ctatgtcaaa taataccagt     960

gaagatcaat cttatgatgc tgtggttgtc actgctccaa ttcgcaatgt caaagaaatg    1020

aagattatga aatttggaaa tccattttca cttgacttta ttccagaggt gacgtacgta    1080

cccctttccg ttatgattac tgcattcaaa aaggataaag tgaagagacc tcttgagggc    1140
```

-continued

```
ttcggagttc ttatcccctc taaagagcaa cataatggac tgaagactct tggtacttta   1200

ttttcctcca tgatgtttcc tgatcgtgct ccatctgaca tgtgtctctt tactacattt   1260

gtcggaggaa gcagaaatag aaaacttgca aacgcttcaa cggatgaatt gaagcaaata   1320

gtttcttctg accttcagca gctgttgggc actgaggacg aaccttcatt tgtcaatcat   1380

ctcttttgga gcaacgcatt cccattgtat ggacacaatt acgattctgt tttgagagcc   1440

atagacaaga tggaaaagga tcttcctgga ttttttatg caggtaacca taagggtgga   1500

ctttcagtgg gaaaagcgat ggcctccgga tgcaaggctg cggaacttgt aatatcctat   1560

ctggactctc atatatatgt gaagatggat gagaagaccg cgtaa                   1605
```

<210> SEQ ID NO 16
<211> LENGTH: 534
<212> TYPE: PRT
<213> ORGANISM: Amaranthus tuberculatus

<400> SEQUENCE: 16

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285
```

-continued

```
Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530


<210> SEQ ID NO 17
<211> LENGTH: 1653
<212> TYPE: DNA
<213> ORGANISM: Amaranthus tuberculatus

<400> SEQUENCE: 17

atgagtgcga tggcgttatc gagcagcatt ctacaatgtc cgccgcactc cgacatctcg      60

ttccgctttt ttgctcatac acgaacccaa ccccccatct tcttcggaag accacgaaaa     120

ttatcatata tccattgttc cacaagctca agctcaactg ccaattacca gaacaccatt     180

acgagccaag gagaaggaga taaagtatta gattgtgtaa ttgttggagc tggtatcagt     240

ggactttgca ttgctcaggc tctttctacc aaacacattc aatccaatct caatttcatt     300

gtcactgaag ctaaacatcg tgttggaggt aatatcacta ccatggagtc cgatggctat     360

atctgggaag agggtcctaa tagtttccaa ccctccgatc ctgtgcttac tatggcggtt     420

gacagtggat tgaaagacga tttggtcttg ggagatccta atgcccctcg tttcgtgctc     480

tggaatggta aattaaggcc tgttccttcc aaacctacgg accttccctt ttttgatctc     540

atgagctttc ctggtaagat tagggctggt cttggtgcac ttggtcttcg tcctcctcct     600

ccttcttatg aggaatctgt tgaagaattt gtgcgccgta atctcggcga tgaggtcttc     660

gaacgcttga tcgaaccctt ttgttctggt gtctatgctg gtgatcctgc aaagttgagt     720
```

-continued

```
atgaaagctg catttggaaa ggtctggacc ttagagcaaa agggtggtag tatcatagcc    780

ggtacactca aaactattca ggaaaggaaa aataatcctc caccccctcg agacccccgc    840

cttcctaaac ctaagggcca gactgttgga tcctttagga aagggctcat tatgttacct    900

accgccattg ctgctaggct tggcagtaaa gtcaaactat cgtggacact ttctaatatt    960

gataagtcgc tcaatggaga atacaatctc acttatcaaa cacccgatgg accggtttct   1020

gttaggacca aagcggttgt catgaccgtc ccttcgtaca ttgcaagtag cttgcttcgt   1080

ccgctctcag atgttgctgc agattctctt tctaaatttt actatccacc agtcgcagca   1140

gtgtcccttt cttatcccaa agaagcaatt agaccagaat gcttgatcga tggtgaacta   1200

aaaggattcg ggcaattgca tccccgcagc cagggtgtgg aaaccttggg aacaatttat   1260

agttcatctc ttttccctgg tcgagcaccc cccggtagga ccttgatctt gagctacatt   1320

ggaggtgcta caaatcttgg catattacaa aagagtgaag atgaacttgc ggagacagtt   1380

gataaggatc tcagaaaaat tctgataaat ccaaatgcga aaggcagccg tgttctggga   1440

gtgagagtat ggccaaaagc aatcccccaa tttttagttg gtcactttga tgtgctagat   1500

gctgcaaaag ctggtttggc aaatgctggg caaaaggggt tgtttcttgg tggtaattat   1560

gtatcaggtg ttgccttggg gaggtgtata gagggtgctt atgactctgc ttctgaggta   1620

gtggatttcc tctcacagta caaagataag tag                                1653
```

```
<210> SEQ ID NO 18
<211> LENGTH: 550
<212> TYPE: PRT
<213> ORGANISM: Amaranthus tuberculatus

<400> SEQUENCE: 18

Met Ser Ala Met Ala Leu Ser Ser Ser Ile Leu Gln Cys Pro Pro His
1               5                   10                  15

Ser Asp Ile Ser Phe Arg Phe Phe Ala His Thr Arg Thr Gln Pro Pro
            20                  25                  30

Ile Phe Phe Gly Arg Pro Arg Lys Leu Ser Tyr Ile His Cys Ser Thr
        35                  40                  45

Ser Ser Ser Ser Thr Ala Asn Tyr Gln Asn Thr Ile Thr Ser Gln Gly
    50                  55                  60

Glu Gly Asp Lys Val Leu Asp Cys Val Ile Val Gly Ala Gly Ile Ser
65                  70                  75                  80

Gly Leu Cys Ile Ala Gln Ala Leu Ser Thr Lys His Ile Gln Ser Asn
                85                  90                  95

Leu Asn Phe Ile Val Thr Glu Ala Lys His Arg Val Gly Gly Asn Ile
            100                 105                 110

Thr Thr Met Glu Ser Asp Gly Tyr Ile Trp Glu Glu Gly Pro Asn Ser
        115                 120                 125

Phe Gln Pro Ser Asp Pro Val Leu Thr Met Ala Val Asp Ser Gly Leu
    130                 135                 140

Lys Asp Asp Leu Val Leu Gly Asp Pro Asn Ala Pro Arg Phe Val Leu
145                 150                 155                 160

Trp Asn Gly Lys Leu Arg Pro Val Pro Ser Lys Pro Thr Asp Leu Pro
                165                 170                 175

Phe Phe Asp Leu Met Ser Phe Pro Gly Lys Ile Arg Ala Gly Leu Gly
            180                 185                 190

Ala Leu Gly Leu Arg Pro Pro Pro Pro Ser Tyr Glu Glu Ser Val Glu
        195                 200                 205
```

-continued

```
Glu Phe Val Arg Arg Asn Leu Gly Asp Glu Val Phe Glu Arg Leu Ile
    210                 215                 220

Glu Pro Phe Cys Ser Gly Val Tyr Ala Gly Asp Pro Ala Lys Leu Ser
225                 230                 235                 240

Met Lys Ala Ala Phe Gly Lys Val Trp Thr Leu Glu Gln Lys Gly Gly
                245                 250                 255

Ser Ile Ile Ala Gly Thr Leu Lys Thr Ile Gln Glu Arg Lys Asn Asn
            260                 265                 270

Pro Pro Pro Pro Arg Asp Pro Arg Leu Pro Lys Pro Lys Gly Gln Thr
        275                 280                 285

Val Gly Ser Phe Arg Lys Gly Leu Ile Met Leu Pro Thr Ala Ile Ala
    290                 295                 300

Ala Arg Leu Gly Ser Lys Val Lys Leu Ser Trp Thr Leu Ser Asn Ile
305                 310                 315                 320

Asp Lys Ser Leu Asn Gly Glu Tyr Asn Leu Thr Tyr Gln Thr Pro Asp
                325                 330                 335

Gly Pro Val Ser Val Arg Thr Lys Ala Val Val Met Thr Val Pro Ser
            340                 345                 350

Tyr Ile Ala Ser Ser Leu Leu Arg Pro Leu Ser Asp Val Ala Ala Asp
        355                 360                 365

Ser Leu Ser Lys Phe Tyr Tyr Pro Pro Val Ala Ala Val Ser Leu Ser
    370                 375                 380

Tyr Pro Lys Glu Ala Ile Arg Pro Glu Cys Leu Ile Asp Gly Glu Leu
385                 390                 395                 400

Lys Gly Phe Gly Gln Leu His Pro Arg Ser Gln Gly Val Glu Thr Leu
                405                 410                 415

Gly Thr Ile Tyr Ser Ser Ser Leu Phe Pro Gly Arg Ala Pro Pro Gly
            420                 425                 430

Arg Thr Leu Ile Leu Ser Tyr Ile Gly Gly Ala Thr Asn Leu Gly Ile
        435                 440                 445

Leu Gln Lys Ser Glu Asp Glu Leu Ala Glu Thr Val Asp Lys Asp Leu
    450                 455                 460

Arg Lys Ile Leu Ile Asn Pro Asn Ala Lys Gly Ser Arg Val Leu Gly
465                 470                 475                 480

Val Arg Val Trp Pro Lys Ala Ile Pro Gln Phe Leu Val Gly His Phe
                485                 490                 495

Asp Val Leu Asp Ala Ala Lys Ala Gly Leu Ala Asn Ala Gly Gln Lys
            500                 505                 510

Gly Leu Phe Leu Gly Gly Asn Tyr Val Ser Gly Val Ala Leu Gly Arg
        515                 520                 525

Cys Ile Glu Gly Ala Tyr Asp Ser Ala Ser Glu Val Val Asp Phe Leu
    530                 535                 540

Ser Gln Tyr Lys Asp Lys
545                 550
```

<210> SEQ ID NO 19
<211> LENGTH: 1518
<212> TYPE: DNA
<213> ORGANISM: Amaranthus tuberculatus

<400> SEQUENCE: 19

```
atgggcaaca tttctgagcg ggatgaaccc acttctgcta aaagggttgc tgttgttggt      60

gctggagtta gtggacttgc tgctgcatat aagctaaaat cccatggttt gaatgtgaca     120
```

-continued

```
ttgtttgaag ctgattctag agctggaggc aaacttaaaa ctgttaaaaa agatggtttt    180

atttgggatg agggggcaaa tactatgaca gaaagtgagg cagaagtctc gagtttgatc    240

gatgatcttg ggcttcgtga gaagcaacag ttgccaattt cacaaaataa aagatacata    300

gctagagatg gtcttcctgt gctactacct tcaaatcccg ctgcactgct cacgagcaat    360

atcctttcag caaaatcaaa gctgcaaatt atgttggaac cattttctg gagaaaacac     420

aatgctactg agctttctga tgagcatgtt caggaaagcg ttggtgaatt ttttgagcga    480

cattttggga aagagtttgt tgattatgtt attgaccctt ttgttgcggg tacatgtggt    540

ggagatcctc aatcgctttc tatgcaccat acatttccag aagtatggaa tattgaaaaa    600

aggtttggct ctgtgtttgc tggactaatt caatcaacat tgttatctaa gaaggaaaag    660

ggtggaggag gaaatgcttc tatcaagaag cctcgtgtac gtggttcatt ttcattccat    720

ggtggaatgc agacacttgt tgacacaata tgcaaacagc ttggtgaaga tgaactcaaa    780

ctccagtgtg aggtgctgtc cttgtcatac aaccagaagg ggatcccttc attagggaat    840

tggtcagtct cttctatgtc aaataatacc agtgaagatc aatcttatga tgctgtggtt    900

gtcactgctc caattcgcaa tgtcaaagaa atgaagatta tgaaattcgg aaatccattt    960

tcacttgact ttattccaga ggtgagttac gtacccctct ctgttatgat tactgcattc   1020

aagaaggata aagtgaagag accactcgag ggctttggag ttcttatccc ctctaaagag   1080

caacataatg gactgaagac tcttggtact ttattttcct ccatgatgtt tcccgatcgt   1140

gctccatctg acatgtgtct ctttactaca tttgtcggag gaagcagaaa tagaaaactt   1200

gcaaacgctt caacggatga attgaagcaa atagtttctt ctgaccttca gcagctgttg   1260

ggcactgagg acgaaccttc atttgtcaat catctctttt ggagcaacgc attcccgttg   1320

tatggacaca attacgattc tgttttgaga gccatagaca agatggaaaa ggatcttcct   1380

ggattttttt atgcaggtaa ccataagggt ggactttcag tgggaaaagc gatggcctcc   1440

ggatgcaagg ctgcggaact tgtaatatcc tatctggact ctcatatata tgtgaagatg   1500

gatgagaaga ccgcgtaa                                                 1518
```

<210> SEQ ID NO 20
<211> LENGTH: 505
<212> TYPE: PRT
<213> ORGANISM: Amaranthus tuberculatus

<400> SEQUENCE: 20

```
Met Gly Asn Ile Ser Glu Arg Asp Glu Pro Thr Ser Ala Lys Arg Val
1               5                   10                  15

Ala Val Val Gly Ala Gly Val Ser Gly Leu Ala Ala Ala Tyr Lys Leu
            20                  25                  30

Lys Ser His Gly Leu Asn Val Thr Leu Phe Glu Ala Asp Ser Arg Ala
        35                  40                  45

Gly Gly Lys Leu Lys Thr Val Lys Lys Asp Gly Phe Ile Trp Asp Glu
    50                  55                  60

Gly Ala Asn Thr Met Thr Glu Ser Glu Ala Glu Val Ser Ser Leu Ile
65                  70                  75                  80

Asp Asp Leu Gly Leu Arg Glu Lys Gln Gln Leu Pro Ile Ser Gln Asn
                85                  90                  95

Lys Arg Tyr Ile Ala Arg Asp Gly Leu Pro Val Leu Leu Pro Ser Asn
            100                 105                 110

Pro Ala Ala Leu Leu Thr Ser Asn Ile Leu Ser Ala Lys Ser Lys Leu
        115                 120                 125
```

-continued

```
Gln Ile Met Leu Glu Pro Phe Phe Trp Arg Lys His Asn Ala Thr Glu
    130                 135                 140

Leu Ser Asp Glu His Val Gln Glu Ser Val Gly Glu Phe Phe Glu Arg
145                 150                 155                 160

His Phe Gly Lys Glu Phe Val Asp Tyr Val Ile Asp Pro Phe Val Ala
                165                 170                 175

Gly Thr Cys Gly Gly Asp Pro Gln Ser Leu Ser Met His His Thr Phe
            180                 185                 190

Pro Glu Val Trp Asn Ile Glu Lys Arg Phe Gly Ser Val Phe Ala Gly
        195                 200                 205

Leu Ile Gln Ser Thr Leu Leu Ser Lys Lys Glu Lys Gly Gly Gly Gly
    210                 215                 220

Asn Ala Ser Ile Lys Lys Pro Arg Val Arg Gly Ser Phe Ser Phe His
225                 230                 235                 240

Gly Gly Met Gln Thr Leu Val Asp Thr Ile Cys Lys Gln Leu Gly Glu
                245                 250                 255

Asp Glu Leu Lys Leu Gln Cys Glu Val Leu Ser Leu Ser Tyr Asn Gln
            260                 265                 270

Lys Gly Ile Pro Ser Leu Gly Asn Trp Ser Val Ser Ser Met Ser Asn
        275                 280                 285

Asn Thr Ser Glu Asp Gln Ser Tyr Asp Ala Val Val Val Thr Ala Pro
    290                 295                 300

Ile Arg Asn Val Lys Glu Met Lys Ile Met Lys Phe Gly Asn Pro Phe
305                 310                 315                 320

Ser Leu Asp Phe Ile Pro Glu Val Ser Tyr Val Pro Leu Ser Val Met
                325                 330                 335

Ile Thr Ala Phe Lys Lys Asp Lys Val Lys Arg Pro Leu Glu Gly Phe
            340                 345                 350

Gly Val Leu Ile Pro Ser Lys Glu Gln His Asn Gly Leu Lys Thr Leu
        355                 360                 365

Gly Thr Leu Phe Ser Ser Met Met Phe Pro Asp Arg Ala Pro Ser Asp
    370                 375                 380

Met Cys Leu Phe Thr Thr Phe Val Gly Gly Ser Arg Asn Arg Lys Leu
385                 390                 395                 400

Ala Asn Ala Ser Thr Asp Glu Leu Lys Gln Ile Val Ser Ser Asp Leu
                405                 410                 415

Gln Gln Leu Leu Gly Thr Glu Asp Glu Pro Ser Phe Val Asn His Leu
            420                 425                 430

Phe Trp Ser Asn Ala Phe Pro Leu Tyr Gly His Asn Tyr Asp Ser Val
        435                 440                 445

Leu Arg Ala Ile Asp Lys Met Glu Lys Asp Leu Pro Gly Phe Phe Tyr
    450                 455                 460

Ala Gly Asn His Lys Gly Gly Leu Ser Val Gly Lys Ala Met Ala Ser
465                 470                 475                 480

Gly Cys Lys Ala Ala Glu Leu Val Ile Ser Tyr Leu Asp Ser His Ile
                485                 490                 495

Tyr Val Lys Met Asp Glu Lys Thr Ala
            500                 505
```

<210> SEQ ID NO 21
<211> LENGTH: 1605
<212> TYPE: DNA
<213> ORGANISM: Amaranthus tuberculatus -continued

<400> SEQUENCE: 21

```
atggtaattc aatccattac ccacctttca ccaaaccttg cattgccatc gccattgtca     60
gtttcaacca agaactaccc agtagctgta atgggcaaca tttctgagcg ggaagaaccc    120
acttctgcta aaagggttgc tgttgttggt gctggagtta gtggacttgc tgctgcatat    180
aagctaaaat cccatggttt gagtgtgaca ttgtttgaag ctgattctag agctggaggc    240
aaacttaaaa ctgttaaaaa agatggtttt atttgggatg agggggcaaa tactatgaca    300
gaaagtgagg cagaggtctc gagtttgatc gatgatcttg ggcttcgtga gaagcaacag    360
ttgccaattt cacaaaataa aagatacata gctagagacg gtcttcctgt gctactacct    420
tcaaatcccg ctgcactact cacgagcaat atcctttcag caaaatcaaa gctgcaaatt    480
atgttggaac catttctctg gagaaaacac aatgctactg aactttctga tgagcatgtt    540
caggaaagcg ttggtgaatt ttttgagcga cattttggga aagagtttgt tgattatgtt    600
atcgaccctt ttgttgcggg tacatgtggt ggagatcctc aatcgctttc catgcaccat    660
acatttccag aagtatggaa tattgaaaaa aggtttggct ctgtgtttgc tggactaatt    720
caatcaacat tgttatctaa gaaggaaaag ggtggagaaa atgcttctat taagaagcct    780
cgtgtacgtg gttcattttc atttcaaggt ggaatgcaga cacttgttga cacaatgtgc    840
aaacagcttg gtgaagatga actcaaactc cagtgtgagg tgctgtcctt gtcatataac    900
cagaagggga tcccctcatt agggaattgg tcagtctctt ctatgtcaaa taataccagt    960
gaagatcaat cttatgatgc tgtggttgtc actgctccaa ttcgcaatgt caaagaaatg   1020
aagattatga aatttggaaa tccattttca cttgacttta ttccagaggt gacgtacgta   1080
cccctttccg ttatgattac tgcattcaaa aaggataaag tgaagagacc tcttgagggc   1140
ttcggagttc ttatcccctc taaagagcaa cataatggac tgaagactct tggtacttta   1200
ttttcctcca tgatgtttcc tgatcgtgct ccatctgaca tgtgtctctt tactacattt   1260
gtcggaggaa gcagaaatag aaaacttgca aacgcttcaa cggatgaatt gaagcaaata   1320
gtttcttctg accttcagca gctgttgggc actgaggacg aaccttcatt tgtcaatcat   1380
ctcttttgga gcaacgcatt cccattgtat ggacacaatt acgattctgt tttgagagcc   1440
atagacaaga tggaaaagga tcttcctgga ttttttatg caggtaacca taagggtgga    1500
ctttcagtgg gaaaagcgat ggcctccgga tgcaaggctg cggaacttgt aatatcctat   1560
ctggactctc atatatacgt gaagatggat gagaagaccg cgtaa                   1605
```

<210> SEQ ID NO 22
<211> LENGTH: 534
<212> TYPE: PRT
<213> ORGANISM: Amaranthus tuberculatus

<400> SEQUENCE: 22

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80
```

-continued

```
Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
```

-continued

```
            500                 505                 510

Ala Ala Glu Leu Val Ile Ser Tyr Leu Asp Ser His Ile Tyr Val Lys
        515                 520                 525

Met Asp Glu Lys Thr Ala
    530


<210> SEQ ID NO 23
<211> LENGTH: 1659
<212> TYPE: DNA
<213> ORGANISM: Amaranthus tuberculatus

<400> SEQUENCE: 23

atgagtgcga tggcgttatc gagcagcatt ctacaatgtc cgccgcactc cgacatctcg     60

ttccgctttt ttgctcatac acgaacccca tccccccatct tcttcggaag aacacgaaaa    120

ttatcatata tccattgttc cacaagctca agctcaactg ccaattacca gaacacgatt    180

acgagccaag gagaaggaga taaagtatta gattgtgtaa ttgttggagc tggtatcagt    240

ggactttgca ttgctcaggc tctttctacc aaacacattc aatccaatct caatttcatt    300

gtcactgaag ctaaacatcg tgttggaggt aatatcacta ccatggagtc cgatggctat    360

atctgggaag agggtcctaa tagtttccaa ccctccgatc ctgtgcttac tatggcggtt    420

gacagtggat tgaaagacga tttagtcttg ggagatccta atgcccctcg tttcgtgctc    480

tggaatggta aattaaggcc tgttccttcc aaacctacgg accttccctt ttttgatctc    540

atgagctttc ctggtaagat tagggctggt cttggtgcac ttggtcttcg tcctcctcct    600

cctcctcctt cttatgagga atctgttgaa gaatttgtgc gccgtaatct cggcgatgag    660

gtcttcgaac gcttgatcga acccttttgt tctggtgtct atgctggtga tcctgcaaag    720

ttgagtatga aagctgcatt tggaaaggtc tggaccttag agcaaaaggg tggtagtatc    780

atagccggta cactcaaaac tattcaggaa aggaaaaata atcctccacc ccctcgagac    840

ccccgccttc ctaaacctaa gggccagact gttggatcct ttaggaaagg gctcattatg    900

ttacctaccg ccattgctgc taggcttggc agtaaagtca aactatcgtg gacactttct    960

aatattgata agtcgctcaa tggagaatac aatctcactt atcaaacacc cgatggaccg   1020

gtttctgtta ggaccaaagc ggttgtcatg accgtccctt cgtacattgc aagtagcttg   1080

cttcgtccgc tctcagatgt tgctgcagat tctctttcta aattttacta tccaccagtc   1140

gcagcagtgt ccctttctta tcccaaagaa gcaattagac cagaatgctt gattgatgga   1200

gaactaaaag gattcgggca attgcatccc cgcagccagg gtgtggaaac cttgggaaca   1260

atttatagtt catctctttt ccctggtcga gcaccacccg gtaggacctt gatcttgagc   1320

tacattggag gtgctacaaa tcttggcata ttacaaaaga gtgaagatga actcgcggag   1380

acagttgata aggatctcag aaaaattctg ataaatccaa atgcgaaagg cagccgtgtt   1440

ctgggagtga gagtatggcc aaaggcaatc ccccaatttt tagttggtca ctttgatgtg   1500

ctagatgctg caaaagctgg tttggcaaat gctgggctaa aggggttgtt tcttggtggt   1560

aattatgtat caggtgttgc cttggggagg tgtatagagg gtgcttatga ctctgcttct   1620

gaggtagtgg atttcctctc acagtacaaa gataagtag                          1659


<210> SEQ ID NO 24
<211> LENGTH: 552
<212> TYPE: PRT
<213> ORGANISM: Amaranthus tuberculatus

<400> SEQUENCE: 24
```

-continued

```
Met Ser Ala Met Ala Leu Ser Ser Ser Ile Leu Gln Cys Pro Pro His
1               5                   10                  15

Ser Asp Ile Ser Phe Arg Phe Phe Ala His Thr Arg Thr Pro Ser Pro
            20                  25                  30

Ile Phe Phe Gly Arg Thr Arg Lys Leu Ser Tyr Ile His Cys Ser Thr
        35                  40                  45

Ser Ser Ser Ser Thr Ala Asn Tyr Gln Asn Thr Ile Thr Ser Gln Gly
    50                  55                  60

Glu Gly Asp Lys Val Leu Asp Cys Val Ile Val Gly Ala Gly Ile Ser
65                  70                  75                  80

Gly Leu Cys Ile Ala Gln Ala Leu Ser Thr Lys His Ile Gln Ser Asn
                85                  90                  95

Leu Asn Phe Ile Val Thr Glu Ala Lys His Arg Val Gly Gly Asn Ile
            100                 105                 110

Thr Thr Met Glu Ser Asp Gly Tyr Ile Trp Glu Glu Gly Pro Asn Ser
        115                 120                 125

Phe Gln Pro Ser Asp Pro Val Leu Thr Met Ala Val Asp Ser Gly Leu
    130                 135                 140

Lys Asp Asp Leu Val Leu Gly Asp Pro Asn Ala Pro Arg Phe Val Leu
145                 150                 155                 160

Trp Asn Gly Lys Leu Arg Pro Val Pro Ser Lys Pro Thr Asp Leu Pro
                165                 170                 175

Phe Phe Asp Leu Met Ser Phe Pro Gly Lys Ile Arg Ala Gly Leu Gly
            180                 185                 190

Ala Leu Gly Leu Arg Pro Pro Pro Pro Pro Pro Ser Tyr Glu Glu Ser
        195                 200                 205

Val Glu Glu Phe Val Arg Arg Asn Leu Gly Asp Glu Val Phe Glu Arg
    210                 215                 220

Leu Ile Glu Pro Phe Cys Ser Gly Val Tyr Ala Gly Asp Pro Ala Lys
225                 230                 235                 240

Leu Ser Met Lys Ala Ala Phe Gly Lys Val Trp Thr Leu Glu Gln Lys
                245                 250                 255

Gly Gly Ser Ile Ile Ala Gly Thr Leu Lys Thr Ile Gln Glu Arg Lys
            260                 265                 270

Asn Asn Pro Pro Pro Pro Arg Asp Pro Arg Leu Pro Lys Pro Lys Gly
        275                 280                 285

Gln Thr Val Gly Ser Phe Arg Lys Gly Leu Ile Met Leu Pro Thr Ala
    290                 295                 300

Ile Ala Ala Arg Leu Gly Ser Lys Val Lys Leu Ser Trp Thr Leu Ser
305                 310                 315                 320

Asn Ile Asp Lys Ser Leu Asn Gly Glu Tyr Asn Leu Thr Tyr Gln Thr
                325                 330                 335

Pro Asp Gly Pro Val Ser Val Arg Thr Lys Ala Val Val Met Thr Val
            340                 345                 350

Pro Ser Tyr Ile Ala Ser Ser Leu Leu Arg Pro Leu Ser Asp Val Ala
        355                 360                 365

Ala Asp Ser Leu Ser Lys Phe Tyr Tyr Pro Pro Val Ala Ala Val Ser
    370                 375                 380

Leu Ser Tyr Pro Lys Glu Ala Ile Arg Pro Glu Cys Leu Ile Asp Gly
385                 390                 395                 400

Glu Leu Lys Gly Phe Gly Gln Leu His Pro Arg Ser Gln Gly Val Glu
                405                 410                 415
```

-continued

```
Thr Leu Gly Thr Ile Tyr Ser Ser Ser Leu Phe Pro Gly Arg Ala Pro
            420                 425                 430

Pro Gly Arg Thr Leu Ile Leu Ser Tyr Ile Gly Gly Ala Thr Asn Leu
        435                 440                 445

Gly Ile Leu Gln Lys Ser Glu Asp Glu Leu Ala Glu Thr Val Asp Lys
    450                 455                 460

Asp Leu Arg Lys Ile Leu Ile Asn Pro Asn Ala Lys Gly Ser Arg Val
465                 470                 475                 480

Leu Gly Val Arg Val Trp Pro Lys Ala Ile Pro Gln Phe Leu Val Gly
                485                 490                 495

His Phe Asp Val Leu Asp Ala Ala Lys Ala Gly Leu Ala Asn Ala Gly
            500                 505                 510

Leu Lys Gly Leu Phe Leu Gly Gly Asn Tyr Val Ser Gly Val Ala Leu
        515                 520                 525

Gly Arg Cys Ile Glu Gly Ala Tyr Asp Ser Ala Ser Glu Val Val Asp
    530                 535                 540

Phe Leu Ser Gln Tyr Lys Asp Lys
545                 550


<210> SEQ ID NO 25
<211> LENGTH: 1602
<212> TYPE: DNA
<213> ORGANISM: Amaranthus tuberculatus

<400> SEQUENCE: 25

atggtaattc aatccattac ccacctttca ccaaaccttg cattgccatc gccattgtca      60

gtttccacca agaactaccc agtagctgta atgggcaaca tttctgagcg agaagaaccc     120

acttctgcta aaagggttgc tgttgttggt gctggagtta gtggacttgc tgctgcatat     180

aagctaaaat cccatggttt gagtgtgaca ttgtttgaag ctgattctag agctggaggc     240

aaacttaaaa ctgttaaaaa agatggtttt atttgggatg agggggcaaa tactatgaca     300

gaaagtgagg cagaggtctc gagtttgatc gatgatcttg ggcttcgtga gaagcaacag     360

ttgccaattt cacaaaataa aagatacata gctagagacg gtcttcctgt gctactacct     420

tcaaatcccg ctgcactact cacgagcaat atcctttcag caaaatcaaa gctgcaaatt     480

atgttggaac catttctctg gagaaaacac aatgctactg aactttctga tgagcatgtt     540

caggaaagcg ttggtgaatt ttttgagcga cattttggga aagagtttgt tgattatgtt     600

attgaccctt ttgttgcggg tacatgtgga gatcctcaat cgctttccat gcaccataca     660

tttccagaag tatggaatat tgaaaaaagg tttggctctg tgtttgctgg actaattcaa     720

tcaacattgt tatctaagaa ggaaaagggt ggagaaaatg cttctattaa gaagcctcgt     780

gtacgtggtt cattttcatt tcaaggtgga atgcagacac ttgttgacac aatgtgcaaa     840

cagcttggtg aagatgaact caaactccag tgtgaggtgc tgtccttgtc atataaccag     900

aaggggatcc cctcattagg gaattggtca gtctcttcta tgtcaaataa taccagtgaa     960

gatcaatctt atgatgctgt ggttgtcact gctccaattc gcaatgtcaa agaaatgaag    1020

attatgaaat ttggaaatcc attttcactt gactttattc cagaggtgac gtacgtaccc    1080

ctttccgtta tgattactgc attcaaaaag gataaagtga agagacctct tgagggcttc    1140

ggagttctta tcccctctaa agagcaacat aatggactga agactcttgg tactttattt    1200

tcctccatga tgtttcctga tcgtgctcca tctgacatgt gtctctttac tacatttgtc    1260

ggaggaagca gaaatagaaa acttgcaaac gcttcaacgg atgaattgaa gcaaatagtt    1320
```

-continued

```
tcttctgacc ttcagcagct gttgggcact gaggacgaac cttcatttgt caatcatctc   1380

ttttggagca acgcattccc attgtatgga cacaattacg attgtgtttt gagagccata   1440

gacaagatgg aaaaggatct tcctggattt ttttatgcag gtaaccataa gggtggactt   1500

tcagtgggaa aagcgatggc ctccggatgc aaggctgcgg aacttgtaat atcctatctg   1560

gactctcata tatacgtgaa gatggatgag aagaccgcgt aa                      1602


<210> SEQ ID NO 26
<211> LENGTH: 533
<212> TYPE: PRT
<213> ORGANISM: Amaranthus tuberculatus

<400> SEQUENCE: 26

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
```

-continued

```
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Cys Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525

Asp Glu Lys Thr Ala
    530
```

<210> SEQ ID NO 27
<211> LENGTH: 1605
<212> TYPE: DNA
<213> ORGANISM: Amaranthus tuberculatus

<400> SEQUENCE: 27

```
atggtaattc aatccattac ccacctttca ccaaaccttg cattgccatc gccattgtca      60

gtttcaacca agaactaccc agtagctgta atgggcaaca tttctgagcg ggaagaaccc     120

acttctgcta aaagggttgc tgttgttggt gctggagtta gtggacttgc tgctgcatat     180

aagctaaaat cccatggttt gagtgtgaca ttgtttgaag ctgattctag agctggaggc     240

aaacttaaaa ctgttaaaaa agatggtttt atttgggatg agggggcaaa tactatgaca     300

gaaagtgagg cagaggtctc gagtttgatc gatgatcttg ggcttcgtga gaagcaacag     360

ttgccaattt cacaaaataa aagatacata gctagagccg gtcttcctgt gctactacct     420

tcaaatcccg ctgcactact cacgagcaat atcctttcag caaaatcaaa gctgcaaatt     480

atgttggaac catttctctg gagaaaacac aatgctactg aactttctga tgagcatgtt     540

caggaaagcg ttggtgaatt ttttgagcga cattttggga aagagtttgt tgattatgtt     600

attgaccctt ttgttgcggg tacatgtggt ggagatcctc aatcgctttc catgcaccat     660

acatttccag aagtatggaa tattgaaaaa aggtttggct ctgtgtttgc cggactaatt     720

caatcaacat tgttatctaa gaaggaaaag ggtggagaaa atgcttctat taagaagcct     780

cgtgtacgtg gttcattttc atttcaaggt ggaatgcaga cacttgttga cacaatgtgc     840

aaacagcttg gtgaagatga actcaaactc cagtgtgagg tgctgtcctt gtcatataac     900
```

```
cagaaggga tcccctcact agggaattgg tcagtctctt ctatgtcaaa taataccagt    960

gaagatcaat cttatgatgc tgtggttgtc actgctccaa ttcgcaatgt caaagaaatg   1020

aagattatga aatttggaaa tccattttca cttgacttta ttccagaggt gacgtacgta   1080

cccctttccg ttatgattac tgcattcaaa aaggataaag tgaagagacc tcttgagggc   1140

ttcggagttc ttatcccctc taaagagcaa cataatggac tgaagactct tggtacttta   1200

ttttcctcca tgatgtttcc tgatcgtgct ccatctgaca tgtgtctctt tactacattt   1260

gtcggaggaa gcagaaatag aaaacttgca aacgcttcaa cggatgaatt gaagcaaata   1320

gtttcttctg accttcagca gctgttgggc actgaggacg aaccttcatt tgtcaatcat   1380

ctcttttgga gcaacgcatt cccattgtat ggacacaatt acgattctgt tttgagagcc   1440

atagacaaga tggaaaagga tcttcctgga tttttttatg caggtaacca taagggtgga   1500

ctttcagtgg gaaaagcgat ggcctccgga tgcaaggctg cggaacttgt aatatcctat   1560

ctggactctc atatatacgt gaagatggat gagaagaccg cgtaa             1605
```

<210> SEQ ID NO 28
<211> LENGTH: 534
<212> TYPE: PRT
<213> ORGANISM: Amaranthus tuberculatus

<400> SEQUENCE: 28

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Ala Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255
```

-continued

```
Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530


<210> SEQ ID NO 29
<211> LENGTH: 1602
<212> TYPE: DNA
<213> ORGANISM: Amaranthus tuberculatus

<400> SEQUENCE: 29

atggtaattc aatccattac ccacctttca ccaaaccttg cattgccatc gccattgtca      60

gtttccacca agaactaccc agtagctgta atgggcaaca tttctgagcg ggaagaaccc     120

acttctgcta aaagggttgc tgttgttggt gctggagtta gtggacttgc tgctgcatat     180

aagctaaaat cccatggttt gagtgtgaca ttgtttgaag ctaattctag agctggaggc     240

aaacttaaaa ctgttaaaaa agatggtttt atttgggatg agggggcaaa tactatgaca     300

gaaagtgagg cagaggtctc gagtttgatc gatgatcttg ggcttcgtga gaagcaacag     360

ttgccaattt cacaaaataa aagatacata gctagagacg gtcttcctgt gctactacct     420

tcaaatcccg ctgcactact cacgagcaat atcctttcag caaaatcaaa gctgcaaatt     480
```

-continued

```
atgttggaac catttctctg gagaaaacac aatgctactg aactttctga tgagcatgtt    540

caggaaagcg ttggtgaatt ttttgagcga cattttggga aagagtttgt tgattatgtt    600

attgaccctt ttgttgcggg tacatgtgga gatcctcaat cgctttccat gtaccataca    660

tttccagaag tatggaatat tgaaaaaagg tttggctctg tgtttgctgg actaattcaa    720

tcaacattgt tatctaagaa ggaaaagggt ggagaaaatg cttctattaa gaagcctcgt    780

gtacgtggtt cattttcatt tcaaggtgga atgcagacac ttgttgacac aatgtgcaaa    840

cagcttggtg aagatgaact caaactccag tgtgaggtgc tgtccttgtc atataaccag    900

aaggggatcc cctcattagg gaattggtca gtctcttcta tgtcaaataa taccagtgaa    960

gatcaatctt atgatgctgt ggttgtcact gctccaattc gcaatgtcaa agaaatgaag   1020

attatgaaat ttggaaatcc attttcactt gactttattc cagaggtgac gtacgtaccc   1080

ctttccgtta tgattactgc attcaaaaag gataaagtga agagacctct tgagggcttc   1140

ggagttctta tcccctctaa agagcaacat aatggactga agactcttgg tactttattt   1200

tcctccatga tgtttcctga tcgtgctcca tctgacatgt gtctctttac tacatttgtc   1260

ggaggaagca gaaatagaaa acttgcaaac gcttcaacgg atgaattgaa gcaaatagtt   1320

tcttctgacc ttcagcagct gttgggcact gaggacgaac cttcatttgt caatcatctc   1380

ttttggagca acgcattccc attgtatgga cacaattacg attctgtttt gagagccata   1440

gacaagatgg aaaaggatct tcctggattt ttttatgcag gtaaccataa gggtggactt   1500

tcagtgggaa aagcgatggc ctccggatgc aaggctgcgg aacttgtaat atcctatctg   1560

gactctcata tatacgtgaa gatggatgag aagaccgcgt aa                      1602
```

<210> SEQ ID NO 30
<211> LENGTH: 533
<212> TYPE: PRT
<213> ORGANISM: Amaranthus tuberculatus

<400> SEQUENCE: 30

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asn Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175
```

-continued

```
Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met Tyr His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525

Asp Glu Lys Thr Ala
    530
```

<210> SEQ ID NO 31
<211> LENGTH: 4797
<212> TYPE: DNA
<213> ORGANISM: Amaranthus tuberculatus

<400> SEQUENCE: 31

```
aagaattgaa ttggcagatt gagacaaaat tggattcaga atttagcaaa tttaaaccga      60
```

-continued

```
tcgtatggta attcaatcca ttacccacct ttcaccaaac cttgcattgc catcgccatt    120
gtcagtttca accaagaact acccagtagc tgtaatgggc aacatttctg agcgggaaga    180
acccagtaag tcaacctttc ttcacatatc ttaaagcaat ccctttttcaa ctacactttc    240
ttttgatgat ttcacattct gagttttttt tattggggat ttttagcttc tgctaaaagg    300
gttgctgttg ttggtgctgg agttaggtaa attttatgtt tcttttccag aaagattgta    360
aaattttgct ttgattgttc tgaattttga tgggtttttg cataatgatt tgtatttggg    420
atgggcaaat ttttcagtag atcatactac ttttaacttc tattttctgt ataattttat    480
tgatttccta aactgttttt gtggaattgt tctagtggac ttgctgctgc atataagcta    540
aaatcccatg gtttaagtgt gacattgttt gaagctgatt ctagagctgg aggcaaactt    600
aaaactgtta aaaaagatgg ttttatttgg gatgaggggg caaatactat ggtaatgttt    660
atcaacaatg ctggttttct gatttagaac caattacttg ctggattttg ggtcaattct    720
gtggttaaca tgtcactttc tgatatgctt gtagacagaa agtgaggcag aggtctcgag    780
tttgatcgat gatcttgggc ttcgtgagaa gcaacagttg gtaagttttc tgtctaagcc    840
cattcccttt gcttgctaga gtccgtagcg caaaaatacg gtaatagtca tgatcgtggt    900
aatgacatgg tgatgcggtg acaggagtca tgtgatcgtt attccaacta taggtcaaaa    960
acatgatatt ttccttgtga cgccccaaaa tgcagtattt ttacaccttt acattgcggg   1020
gaaaaatagg tttattatgt tgaaaacctt tacaaggcgg ctgatgcgat gcggccttgt   1080
ttttgcatta tgttcttgaa gcaacttatt atatctttga ttaatgtatc atcagcttaa   1140
aacagcctta ttgtacttct taatctagtt ttgacttttg aggttgcttt tacaagatct   1200
ttatatgatt ggttcttctg tcacagccaa tttcacaaaa taaaagatac atagctagag   1260
acggtcttcc tgtgctagta agtcctctgc atttactttt gacctctatg aacttctaac   1320
actggatact aagttgtatt cgaggcaaat tctgtatttt ccaatctgct tattgacagt   1380
tgcttgcaaa ctttgcagct accttcaaat cccgctgcac tactcacgag caatatcctt   1440
tcagcaaaat caaaggttat caatgctaaa atcatgtttg gtatttgatt acttagcttt   1500
tggtgtatgc aataatttgg tttctaaaac taagtgattg acggaaaagg agggacgaag   1560
gacatagaat tgcaatttg tgttcttcat gtatttttac ttttagagta ggtaagtcac   1620
tttcggtccg tttggttaat ggtactagtt ggtggtaata ggaatgattt gtagtgtaaa   1680
ttttcaagat atatatcatg tcattcccat ggtaatgaaa gtttgatcat aaaaaggttt   1740
tttgttcaca attttccatt accacctaat accacatgtt taaatggtaa tgcattggaa   1800
tgagttttgt gaagaaaatg agtttgttga gaaagaataa gcatggtcat taaatttgtc   1860
aagagatatt cctatcaaaa ttacactagc tttccattat catttcacca tttagtaccg   1920
attaccaaat gggccgttta tagtttggga agagcatacg tttgtgtaaa acttttattt   1980
tgaagttgaa agaatttgtt gcaccttttg ttatgattag gttttgatgt ttttagctgc   2040
aataaatttg ttgatgaaaa agccactact tttttctcag ctgcaaatta tgttggaacc   2100
atttctctgg agaaaacaca atgctactga actttctgat gagcatgttc aggaaaggca   2160
agtgccacat actattaagt gttagttgct gagaatatat ttgaatctaa gatgcacgaa   2220
gaccactggt gcccttgctc tatcaattct gatggaaagg attatcgctg aatttacctt   2280
ctactaaaac atcgataaaa tacttcatta ttagcatcaa aagattccct ccatccttct   2340
ggttttgcta gacttgcctt atgaaggtgt tcaaggagta gtttgctacc cttcaagata   2400
gggtagtggt tgccgtctct cataatttca gtcactcgtt ttcctctcct aattcaagcc   2460
```

-continued

```
ataattttta tggttcctcc acacaacact tgctaaattt gaaaagtagc aaagaggaag   2520
tgagcaaaat cagcaggagt aggactgatg agtaagagct tgattaagtg tagaggattt   2580
tcttttgtgt tgaatatgaa tgcatcatgc atgactgtag aattgacata atgatttgtc   2640
tgcagcgttg gtgaattttt tgagcgacat tttgggaaag aggtattgtt gccaattgcc   2700
atgctctatt cattccggtg aattaacaaa tgttgtgctt ctgcttacta ttgcttataa   2760
ttattgtttg ttgcagtttg ttgattatgt tattgaccct tttgttgcgg gtacatgtgg   2820
tggagatcct caatcgcttt ccgtgagtta aatactgtgc ttgctttttt ttttcaacat   2880
tttctggagg ctgtaaataa attatactcc ttcctattct aatcaaatat cctatttccc   2940
cttttggcat attcaaattt agttaaatat tgtgtaaatt atttacacaa ttgccattaa   3000
attttcactt ttcccttact cactcttctc atgtgtccct tccccctttt cttaaaattg   3060
gtgcattatc aaataggaca tttgatttga ataggcggga gtttccaatt gtgcttccaa   3120
aggtagcttg tcactttttc tttttcttta aattttgtac catgccatgc attttgaacc   3180
tcaactcatt tcgccataaa ggaatattat gtttgagaag aacgaggata ctattatctt   3240
atagataaca tataggtttc attatcaatg attgtttgat tttcaactct tcttttcctt   3300
tcatgctcat attgatgtta tttctatttg ttatgaatta tgtccattgt gttaatgtct   3360
ttctttattg tagatgcacc atacatttcc agaagtatgg aatattgaaa aaaggtatga   3420
accttaaagc tttaatttc ttcgaactta atgtttctta attgattctt ttggatcaat   3480
ttccataaga atggaaattt aaaaaaaggt atgaacctta aagatttctt cgaacttata   3540
tgttttgtaa ttcatgcttt tagatgttgc accattttat ctatgtgtct taagtttgtt   3600
gtaatcattt gtagaccaaa agaatgaatg gtctggtttg aaatggttca tcgtgcaaaa   3660
atgcgatttt gcttgtgatt gaggtaacat tcaaggtgat gtgtttgtcg tactgtcaaa   3720
tgtcttccta taccatatga tatatatata agcctaaaat gatatattgt ataccttag   3780
gatgtggata gcaggggttc agtacatatg aaaaatcctt gcaatttgat ctgtacgata   3840
caatgtgatt ttgccttttg ccttttgcct tttgttatat gatgatgatt ccatgtgaaa   3900
ttttgggatt tagaaaattc acttgtttaa gaacatttga atcaaacttt caccaatttc   3960
aaccacattt aattgcggca aagccgaact ttaaaagtca ctcccaatct ttgagatatc   4020
caaactccaa aacttctatt agctttcatg ttttcactaa gtaaagttgg tgcgactcct   4080
taccatttc tttattatgc atttcgttga tgtataatag tatagattgg tgctctcttc   4140
gctctccttc caacatgcat aacttctagt tcttgtcgtt ttcttttcct ccctattttt   4200
atttgacttg tagctatttt tgttcactct tctcgcccaa tccaaaactt gtagctaaag   4260
aaacttgatt tcattgattt tgtaactgat atgcaattca tttttgtttg cttttagttg   4320
ttgattcaaa aacaataatg ctaaagccct aatcctaaca tgtcgggtta gctgttgaaa   4380
caatacttga aattgctata aaaagggatt tttttcgggt acttcagttg ttgagattga   4440
tatggtcaag tataatttgt tttaacacaa tttgtaatga tttaatggct tagtttcata   4500
gctgtttgta ttaataaagg aaggaggact atccgaaatt gcaataggaa agagatttta   4560
gttcggtatt tggttgttta aattgatatg gccaagtaat gttcatttta cacaattggt   4620
aatgttttat tggctcaata gtgtttgtaa gtatgcgact caaatttaat caagtataac   4680
ttattgaaac ataaataaat atccattagg tttggctctg tgtttgctgg actaattcaa   4740
tcaacattgt tatctaagaa ggaaaagggt ggagaaaatg cttcataaga agcctcg      4797
```

-continued

<210> SEQ ID NO 32
<211> LENGTH: 230
<212> TYPE: PRT
<213> ORGANISM: Amaranthus tuberculatus

<400> SEQUENCE: 32

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Gln Ser Leu Ser Met His His Thr Phe Pro Glu
    210                 215                 220

Val Trp Asn Ile Glu Lys
225                 230
```

<210> SEQ ID NO 33
<211> LENGTH: 4785
<212> TYPE: DNA
<213> ORGANISM: Amaranthus tuberculatus

<400> SEQUENCE: 33

```
aagaattgaa ttggcagatt gagacaaaat tggattcaga atttagcaaa tttaaaccga     60

tcgtatggta attcaatcca ttacccacct ttcaccaaac cttgcattgc catcgccatt    120

gtcagtttcc accaagaact acccagtagc tgtaatgggc aacatttctg agcgagaaga    180

acccagtaag tcaacctttc ttcacatatc ttaaagcaat cccttttcaa ctacactttc    240

ttttgatgat ttcacattct gagttttttt tattggggat ttttagcttc tgctaaaagg    300

gttgctgttg ttggtgctgg agttaggtaa attttatgtt tcttttccag aaagattgta    360

aaattttgct ttgattgttc tgaattttga tgggtttttg cataatgatt tgtatttggg    420

atgggcaaat ttttcagtag atcatactac ttttaacttc tattttctgt ataattttat    480

tgatttccta aattgttttt gtggaattgt tctagtggac ttgctgctgc atataagcta    540
```

-continued

```
aaatcccatg gtttgagtgt gacattgttt gaagctgatt ctagagctgg aggcaaactt    600
aaaactgtta aaaaagatgg ttttatttgg gatgaggggg caaatactat ggtaatgttt    660
atcaacaatg ctggttttct gatttagaac caattacttg ctggattttg ggtcaattct    720
gtggttaaca tgtcactttc tgatatgctt gtagacagaa agtgaggcag aggtctcgag    780
tttgatcgat gatcttgggc ttcgtgagaa gcaacagttg gtaagttttc tgtctaagcc    840
cattcccttt gcttgctaga gtccgtagcg caaaaatacg gtaatagtca tgatcgtggt    900
aatgacatgg tgatgcggtg acaggagtca tgtgatcgtt attccaacta taggtcaaaa    960
acatgatatt ttccttgtga cgccccaaaa tgcggtattt ttacaccttt acattgcggg   1020
gaaaaatagg tttattatgt tgaaaacctt tacaaggcgg ctgatgcgat gcggccttgt   1080
ttttgcatta tgttctagaa gcaacttatt atatctttga ttaatgtatc atcagcttaa   1140
aacagcctta ttgtacttct taatctagtt ttgacttttg aggttgcttt tacaagatct   1200
ttatatgatt ggttcttctg tcacagccaa tttcacaaaa taaaagatac atagctagag   1260
acggtcttcc tgtgctagta agtcctctgc atttactttt gacctctatg aacttctaac   1320
actggatact aagttgtatt cgaggcaaat tctgtatttt ccaatctgct tattgacagt   1380
tgcttgcata ctttgcagct accttcaaat cccgctgcac tactcacgag caatatcctt   1440
tcagcaaaat caaaggttat caatgctaaa atcatgtttg gtatttgatt acttagcttt   1500
tggtgtatgc aataatttgg tttctaaaac taagtgattg acggaaaagg agggacgaag   1560
gacatagaat tgcaattttg tgttcttcat gtatttttac ttttagagta ggtaagtcac   1620
tttcggtccg tttggttaat ggtactagtt ggtggtaata ggaatgattt gtagtgtaaa   1680
ttttcaagat atatatcatg tcattcccat ggtaatgaaa gtttgatcat aaaaaggttt   1740
tttgttcaca attttccatt accacctaat accacatgtt taaatggtaa tgcattggaa   1800
tgagttttgt gaagaaaatg agtttgttga gaaagaataa gcatggtcat taaatttgtc   1860
aagagatatt cctatcaaaa ttacactagc tttccattat catttcacca tttagtaccg   1920
attaccaaat gggccgttta tagtttggga agagcatacg tttgtgtaaa acttttattt   1980
tgaagttgaa agaatttgtt gcaccttttg ttatgattaa gttttgatgt ttttagctgc   2040
aataatttgt tgatgaaaaa gccactactt ttttctcagc tgcaaattat gttggaacca   2100
tttctctgga gaaaacacaa tgctactgaa ctttctgatg agcatgttca ggaaaggcaa   2160
gtgccacata ctattaagtg ttagttgctg agaatatatt tgaatctaag atgcacgaag   2220
accactggtg cccttgctct atcaattctg atggaaagga ttatcgctga atttaccttc   2280
tactaaaaca tcgataaaat acttcattat tagcatcaaa agattccctc catccttctg   2340
gttttgctag acttgcctta tgaaggtgtt caaggagtag tttgctaccc ttcaagatag   2400
ggtagtggtt gccgtctctc ataatttcag tcactcgttt tcctctccta attcaagcca   2460
taatttttat ggttcctcca cacaacactt gctaaatttg aaaagtagca aagaggaagt   2520
gagcaaaatc agcaggagta ggactgatga gtaagagctt gattaagtgt agaggatttt   2580
cttttgtgtt gaatatgaat gcatcatgca tgactgtaga attgacataa tgatttgtct   2640
gcagcgttgg tgaatttttt gagcgacatt ttgggaaaga ggtattgttg ccaattgcca   2700
tgctctattc attccggtga attaacaaat gttgtgcttc tgcttactat tgcttataat   2760
tattgtttgt tgcagtttgt tgattatgtt attgaccctt ttgttgcggg tacatgtgga   2820
gatcctcaat cgctttccgt gagttaaata ctgtgcttgc tttttttttt caacattttc   2880
tggaggctgt aaataaatta tactccttcc tattctaatc aaatatccta tttccccttt   2940
```

-continued

```
tggcatattc aaatttagtt aaatattgtg taaattattt acacaattgc cattaaattt   3000

tcacttttcc cttactcttc tcatgtgtcc cttcccccctt ttcttaaaat tggtgcatta   3060

tcaaatagga catttgattt gaataggcgg gagtttccaa ttgtgcttcc aaaggtagct   3120

tgtcactttt tctttttctt taaattttgt accatgccat gcattttgaa cctcaactca   3180

tttcgccata aaggaatatt atgtttgaga agaacgagga tactattatc ttatagataa   3240

catataggtt tcattatcaa tgattgtttg attttcaact cttcttttcc tttcatgctc   3300

atattgatgt tatttctatt tgttatgaat tatgtccatt gtgttaatgt ctttctttat   3360

tgtagatgca ccatacattt ccagaagtat ggaatattga aaaaaggtat gaaccttaaa   3420

gctttaattt tcttcgaact taatgtttct taattgattc ttttggatca atttccataa   3480

gaatggaaat ttaaaaaagg gtatgaacct taaagatttc ttcgaactta tatgttttgt   3540

aattcatgct tttagatgct gcaccatttt atctatgtgt cttaagtttg ttgtaatcat   3600

ttgtagacca aaagaatgaa tggtctggtt tgaaatggtt catcgtgcaa aaatgcgatt   3660

ttgcttgtga ttgaggtaac attcaaggtg gtgtgtttgt cgtactgtca aatgtcttcc   3720

tataccatgt gatatatata agcctaaaat gatatattgt acacctttag gatgtggata   3780

gcaggggttc agtacatatg aaaaatcctt gcaatttgat ctgtacgatc aatgtgattt   3840

tgccttttgc cttttgcctt ttgttatatg atgatgattc catgtgaaat tttgggattt   3900

agaaaattca cttgtttaag aacatttgaa tcaaactttc accaatttca accacattta   3960

attgcggcaa agccgaactt taaaagtcac tcccaatctt tgagatatcc aaactccaaa   4020

acttctatta gctttcatgt tttcactaag taaagttggt gcgactcctt accattttct   4080

ttattatgca tttcgttgat gtataatagt atagattggt gctctcttcg ctctccttcc   4140

aacatgcata acttctagtt cttgtcgttt tcttttcctc cctattttta tttgacttgt   4200

agctattttt gttcactctt ctcgcccaat ccatagctaa agaaacttga tttcattgat   4260

tttgtaactg atatgcaatt catttttgtt tgcttttagt tgttgattca aaaacaataa   4320

tgctaaagcc ctaatcctaa catgtcgggt tagctgttga aacaatactt gaaattgcta   4380

taaaaaggga ttttttttcgg gtacttcagt tgttgagatt gatatggtca agtataaattt   4440

gttttaacac aatttgtaat gatttaatgg cttagtttca tagctgtttg tattaataaa   4500

ggaaggagga ctatctgaaa ttgcaatagg aaagagattt tagttcggta tttggttgtt   4560

taaattgata tggccaagta atgttcattt tacacaattg gtaatgtttt attggctcaa   4620

tagtgtttgt aagtatgcga ctcaaattta atcaagtata acttattgaa acataaataa   4680

atatccatta ggtttggctc tgtgtttgct ggactaattc aatcaacatt gttatctaag   4740

aaggaaaagg gtggagaaaa tgcttcataa gaagcctcgg acgtc                    4785
```

<210> SEQ ID NO 34
<211> LENGTH: 229
<212> TYPE: PRT
<213> ORGANISM: Amaranthus tuberculatus

<400> SEQUENCE: 34

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45
```

-continued

```
Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
    210                 215                 220

Trp Asn Ile Glu Lys
225


<210> SEQ ID NO 35
<211> LENGTH: 1602
<212> TYPE: DNA
<213> ORGANISM: Amaranthus tuberculatus

<400> SEQUENCE: 35

atggtaattc aatccattac ccacctttca ccaaaccttg cattgccatc gccattgtca     60

gtttcaacca agaactaccc agtagctgta atgggcaaca tttctgagcg ggaagaaccc    120

acttctgcta aaagggttgc tgttgttggt gctggagtta gtggacttgc tgctgcatat    180

aagctaaaat cccatggttt gagtgtgaca ttgtttgaag ctgattctag agctggaggc    240

aaacttaaaa ctgttaaaaa agatggtttt atttgggatg agggggcaaa tactatgaca    300

gaaagtgagg cagaggtctc gagtttgatc gatgatcttg ggcttcgtga gaagcaacag    360

ttgccaattt cacaaaataa aagatacata gctagagacg gtcttcctgt gctactacct    420

tcaaatcccg ctgcactact cacgagcaat atcctttcag caaaatcaaa gctgcaaatt    480

atgttggaac catttctctg gagaaaacac aatgctactg aactttctga tgagcatgtt    540

caggaaagcg ttggtgaatt ttttgagcga cattttggga aagagtttgt tgattatgtt    600

atcgaccctt ttgttgcggg tacatgtgga gatcctcaat cgctttccat gcaccataca    660

tttccagaag tatggaatat tgaaaaaagg tttggctctg tgtttgctgg actaattcaa    720

tcaacattgt tatctaagaa ggaaaagggt ggagaaaatg cttctattaa gaagcctcgt    780

gtacgtggtt cattttcatt tcaaggtgga atgcagacac ttgttgacac aatgtgcaaa    840

cagcttggtg aagatgaact caaactccag tgtgaggtgc tgtccttgtc atataaccag    900

aaggggatcc cctcattagg gaattggtca gtctcttcta tgtcaaataa taccagtgaa    960

gatcaatctt atgatgctgt ggttgtcact gctccaattc gcaatgtcaa agaaatgaag   1020
```

-continued

```
attatgaaat ttggaaatcc attttcactt gactttattc cagaggtgac gtacgtaccc   1080

ctttccgtta tgattactgc attcaaaaag gataaagtga agagacctct tgagggcttc   1140

ggagttctta tcccctctaa agagcaacat aatggactga agactcttgg tactttattt   1200

tcctccatga tgtttcctga tcgtgctcca tctgacatgt gtctctttac tacatttgtc   1260

ggaggaagca gaaatagaaa acttgcaaac gcttcaacgg atgaattgaa gcaaatagtt   1320

tcttctgacc ttcagcagct gttgggcact gaggacgaac cttcatttgt caatcatctc   1380

ttttggagca acgcattccc attgtatgga cacaattacg attctgtttt gagagccata   1440

gacaagatgg aaaaggatct tcctggattt ttttatgcag gtaaccataa gggtggactt   1500

tcagtgggaa aagcgatggc ctccggatgc aaggctgcgg aacttgtaat atcctatctg   1560

gactctcata tatatgtgaa gatggatgag aagaccgcgt aa                      1602


<210> SEQ ID NO 36
<211> LENGTH: 24
<212> TYPE: DNA
<213> ORGANISM: Artificial
<220> FEATURE:
<223> OTHER INFORMATION: Synthetic:  oligonucleotide useful as primer

<400> SEQUENCE: 36

ggagcagtga caaccacagc atca                                            24


<210> SEQ ID NO 37
<211> LENGTH: 22
<212> TYPE: DNA
<213> ORGANISM: Artificial
<220> FEATURE:
<223> OTHER INFORMATION: Synthetic:  oligonucleotide useful as primer

<400> SEQUENCE: 37

atcgatgatc ttgggcttcg tg                                              22


<210> SEQ ID NO 38
<211> LENGTH: 22
<212> TYPE: DNA
<213> ORGANISM: Artificial
<220> FEATURE:
<223> OTHER INFORMATION: Synthetic:  oligonucleotide useful as primer

<400> SEQUENCE: 38

aatggtaagg agtcgcacca ac                                              22


<210> SEQ ID NO 39
<211> LENGTH: 20
<212> TYPE: DNA
<213> ORGANISM: Artificial
<220> FEATURE:
<223> OTHER INFORMATION: Synthetic:  oligonucleotide useful as primer

<400> SEQUENCE: 39

cttcaaatcc cgctgcacta                                                 20


<210> SEQ ID NO 40
<211> LENGTH: 19
<212> TYPE: DNA
<213> ORGANISM: Artificial
<220> FEATURE:
<223> OTHER INFORMATION: Synthetic:  oligonucleotide useful as primer

<400> SEQUENCE: 40

tacttctgga aatgtatgg                                                  19
```

-continued

<210> SEQ ID NO 41
<211> LENGTH: 22
<212> TYPE: DNA
<213> ORGANISM: Artificial
<220> FEATURE:
<223> OTHER INFORMATION: Synthetic: oligonucleotide useful as primer

<400> SEQUENCE: 41
gagaaaacac aatgctactg aa 22

<210> SEQ ID NO 42
<211> LENGTH: 20
<212> TYPE: DNA
<213> ORGANISM: Artificial
<220> FEATURE:
<223> OTHER INFORMATION: Synthetic: oligonucleotide useful as primer

<400> SEQUENCE: 42
acagcctcca gaaaatgttg 20

<210> SEQ ID NO 43
<211> LENGTH: 66
<212> TYPE: DNA
<213> ORGANISM: Artificial
<220> FEATURE:
<223> OTHER INFORMATION: Synthetic: partial coding sequence characteristic of herbicide sensitive PPX2L of Amaranthus tuberculatus

<400> SEQUENCE: 43
tttgttgatt atgttattga cccttttgtt gcgggtacat gtggtggaga tcctcaatcg 60
ccttcc 66

<210> SEQ ID NO 44
<211> LENGTH: 63
<212> TYPE: DNA
<213> ORGANISM: Artificial
<220> FEATURE:
<223> OTHER INFORMATION: Synthetic: partial coding sequence characteristic of herbicide resistant PPXL2 of Amaranthus tuberculatus

<400> SEQUENCE: 44
tttgttgatt atgttattga cccttttgtt gcgggtacat gtggagatcc tcaatcgcct 60
tcc 63

<210> SEQ ID NO 45
<211> LENGTH: 1602
<212> TYPE: DNA
<213> ORGANISM: Artificial
<220> FEATURE:
<223> OTHER INFORMATION: Synthetic construct: chimeric, herbicide resistant PPX2L coding sequence
<220> FEATURE:
<221> NAME/KEY: CDS
<222> LOCATION: (1)..(1599)

<400> SEQUENCE: 45

```
atg gta att caa tcc att acc cac ctt tca cca aac ctt gca ttg cca       48
Met Val Ile Gln Ser Ile Thr His Leu Ser Pro Asn Leu Ala Leu Pro
1               5                   10                  15

tcg cca ttg tca gtt tca acc aag aac tac cca gta gct gta atg ggc       96
Ser Pro Leu Ser Val Ser Thr Lys Asn Tyr Pro Val Ala Val Met Gly
            20                  25                  30
```

-continued

```
aac att tct gag cgg gaa gaa ccc act tct gct aaa agg gtt gct gtt      144
Asn Ile Ser Glu Arg Glu Glu Pro Thr Ser Ala Lys Arg Val Ala Val
        35                  40                  45

gtt ggt gct gga gtt agt gga ctt gct gct gca tat aag cta aaa tcc      192
Val Gly Ala Gly Val Ser Gly Leu Ala Ala Ala Tyr Lys Leu Lys Ser
    50                  55                  60

cat ggt ttg agt gtg aca ttg ttt gaa gct gat tct aga gct gga ggc      240
His Gly Leu Ser Val Thr Leu Phe Glu Ala Asp Ser Arg Ala Gly Gly
65                  70                  75                  80

aaa ctt aaa act gtt aaa aaa gat ggt ttt att tgg gat gag ggg gca      288
Lys Leu Lys Thr Val Lys Lys Asp Gly Phe Ile Trp Asp Glu Gly Ala
                85                  90                  95

aat act atg aca gaa agt gag gca gag gtc tcg agt ttg atc gat gat      336
Asn Thr Met Thr Glu Ser Glu Ala Glu Val Ser Ser Leu Ile Asp Asp
            100                 105                 110

ctt ggg ctt cgt gag aag caa cag ttg cca att tca caa aat aaa aga      384
Leu Gly Leu Arg Glu Lys Gln Gln Leu Pro Ile Ser Gln Asn Lys Arg
        115                 120                 125

tac ata gct aga gac ggt ctt cct gtg cta cta cct tca aat ccc gct      432
Tyr Ile Ala Arg Asp Gly Leu Pro Val Leu Leu Pro Ser Asn Pro Ala
    130                 135                 140

gca cta ctc acg agc aat atc ctt tca gca aaa tca aag ctg caa att      480
Ala Leu Leu Thr Ser Asn Ile Leu Ser Ala Lys Ser Lys Leu Gln Ile
145                 150                 155                 160

atg ttg gaa cca ttt ctc tgg aga aaa cac aat gct act gaa ctt tct      528
Met Leu Glu Pro Phe Leu Trp Arg Lys His Asn Ala Thr Glu Leu Ser
                165                 170                 175

gat gag cat gtt cag gaa agc gtt ggt gaa ttt ttt gag cga cat ttt      576
Asp Glu His Val Gln Glu Ser Val Gly Glu Phe Phe Glu Arg His Phe
            180                 185                 190

ggg aaa gag ttt gtt gat tat gtt att gac cct ttt gtt gcg ggt aca      624
Gly Lys Glu Phe Val Asp Tyr Val Ile Asp Pro Phe Val Ala Gly Thr
        195                 200                 205

tgt gga gat cct caa tcg ctt tcc atg cac cat aca ttt cca gaa gta      672
Cys Gly Asp Pro Gln Ser Leu Ser Met His His Thr Phe Pro Glu Val
    210                 215                 220

tgg aat att gaa aaa agg ttt ggc tct gtg ttt gct gga cta att caa      720
Trp Asn Ile Glu Lys Arg Phe Gly Ser Val Phe Ala Gly Leu Ile Gln
225                 230                 235                 240

tca aca ttg tta tct aag aag gaa aag ggt gga gaa aat gct tct att      768
Ser Thr Leu Leu Ser Lys Lys Glu Lys Gly Gly Glu Asn Ala Ser Ile
                245                 250                 255

aag aag cct cgt gta cgt ggt tca ttt tca ttt caa ggt gga atg cag      816
Lys Lys Pro Arg Val Arg Gly Ser Phe Ser Phe Gln Gly Gly Met Gln
            260                 265                 270

aca ctt gtt gac aca atg tgc aaa cag ctt ggt gaa gat gaa ctc aaa      864
Thr Leu Val Asp Thr Met Cys Lys Gln Leu Gly Glu Asp Glu Leu Lys
        275                 280                 285

ctc cag tgt gag gtg ctg tcc ttg tca tat aac cag aag ggg atc ccc      912
Leu Gln Cys Glu Val Leu Ser Leu Ser Tyr Asn Gln Lys Gly Ile Pro
    290                 295                 300

tca tta ggg aat tgg tca gtc tct tct atg tca aat aat acc agt gaa      960
Ser Leu Gly Asn Trp Ser Val Ser Ser Met Ser Asn Asn Thr Ser Glu
305                 310                 315                 320

gat caa tct tat gat gct gtg gtt gtc act gct cca att cgc aat gtc     1008
Asp Gln Ser Tyr Asp Ala Val Val Val Thr Ala Pro Ile Arg Asn Val
                325                 330                 335

aaa gaa atg aag att atg aaa ttt gga aat cca ttt tca ctt gac ttt     1056
Lys Glu Met Lys Ile Met Lys Phe Gly Asn Pro Phe Ser Leu Asp Phe
            340                 345                 350
```

-continued

```
att cca gag gtg acg tac gta ccc ctt tcc gtt atg att act gca ttc     1104
Ile Pro Glu Val Thr Tyr Val Pro Leu Ser Val Met Ile Thr Ala Phe
        355                 360                 365

aaa aag gat aaa gtg aag aga cct ctt gag ggc ttc gga gtt ctt atc     1152
Lys Lys Asp Lys Val Lys Arg Pro Leu Glu Gly Phe Gly Val Leu Ile
    370                 375                 380

ccc tct aaa gag caa cat aat gga ctg aag act ctt ggt act tta ttt     1200
Pro Ser Lys Glu Gln His Asn Gly Leu Lys Thr Leu Gly Thr Leu Phe
385                 390                 395                 400

tcc tcc atg atg ttt cct gat cgt gct cca tct gac atg tgt ctc ttt     1248
Ser Ser Met Met Phe Pro Asp Arg Ala Pro Ser Asp Met Cys Leu Phe
                405                 410                 415

act aca ttt gtc gga gga agc aga aat aga aaa ctt gca aac gct tca     1296
Thr Thr Phe Val Gly Gly Ser Arg Asn Arg Lys Leu Ala Asn Ala Ser
            420                 425                 430

acg gat gaa ttg aag caa ata gtt tct tct gac ctt cag cag ctg ttg     1344
Thr Asp Glu Leu Lys Gln Ile Val Ser Ser Asp Leu Gln Gln Leu Leu
        435                 440                 445

ggc act gag gac gaa cct tca ttt gtc aat cat ctc ttt tgg agc aac     1392
Gly Thr Glu Asp Glu Pro Ser Phe Val Asn His Leu Phe Trp Ser Asn
    450                 455                 460

gca ttc cca ttg tat gga cac aat tac gat tct gtt ttg aga gcc ata     1440
Ala Phe Pro Leu Tyr Gly His Asn Tyr Asp Ser Val Leu Arg Ala Ile
465                 470                 475                 480

gac aag atg gaa aag gat ctt cct gga ttt ttt tat gca ggt aac cat     1488
Asp Lys Met Glu Lys Asp Leu Pro Gly Phe Phe Tyr Ala Gly Asn His
                485                 490                 495

aag ggt gga ctt tca gtg gga aaa gcg atg gcc tcc gga tgc aag gct     1536
Lys Gly Gly Leu Ser Val Gly Lys Ala Met Ala Ser Gly Cys Lys Ala
            500                 505                 510

gcg gaa ctt gta ata tcc tat ctg gac tct cat ata tac gtg aag atg     1584
Ala Glu Leu Val Ile Ser Tyr Leu Asp Ser His Ile Tyr Val Lys Met
        515                 520                 525

gat gag aag acc gcg taa                                             1602
Asp Glu Lys Thr Ala
    530


<210> SEQ ID NO 46
<211> LENGTH: 533
<212> TYPE: PRT
<213> ORGANISM: Artificial
<220> FEATURE:
<223> OTHER INFORMATION: Synthetic Construct

<400> SEQUENCE: 46

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110
```

-continued

```
Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
    210                 215                 220

Trp Asn Ile Glu Lys Arg Phe Gly Ser Val Phe Ala Gly Leu Ile Gln
225                 230                 235                 240

Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
        355                 360                 365

Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
        435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Ser Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525
```

-continued

```
Asp Glu Lys Thr Ala
    530


<210> SEQ ID NO 47
<211> LENGTH: 1605
<212> TYPE: DNA
<213> ORGANISM: Amaranthus tuberculatus
<220> FEATURE:
<221> NAME/KEY: CDS
<222> LOCATION: (1)..(1605)

<400> SEQUENCE: 47

atg gta att caa tcc att acc cac ctt tca cca aac ctt gca ttg cca       48
Met Val Ile Gln Ser Ile Thr His Leu Ser Pro Asn Leu Ala Leu Pro
1               5                   10                  15

tcg cca ttg tca gtt tca acc aag aac tac cca gta gct gta atg ggc       96
Ser Pro Leu Ser Val Ser Thr Lys Asn Tyr Pro Val Ala Val Met Gly
            20                  25                  30

aac att tct gag cgg gaa gaa ccc act tct gct aaa agg gtt gct gtt      144
Asn Ile Ser Glu Arg Glu Glu Pro Thr Ser Ala Lys Arg Val Ala Val
        35                  40                  45

gtt ggt gct gga gtt agt gga ctt gct gct gca tat aag cta aaa tcc      192
Val Gly Ala Gly Val Ser Gly Leu Ala Ala Ala Tyr Lys Leu Lys Ser
    50                  55                  60

cat ggt ttg agt gtg aca ttg ttt gaa gct gat tct aga gct gga ggc      240
His Gly Leu Ser Val Thr Leu Phe Glu Ala Asp Ser Arg Ala Gly Gly
65                  70                  75                  80

aaa ctt aaa act gtt aaa aaa gat ggt ttt att tgg gat gag ggg gca      288
Lys Leu Lys Thr Val Lys Lys Asp Gly Phe Ile Trp Asp Glu Gly Ala
                85                  90                  95

aat act atg aca gaa agt gag gca gag gtc tcg agt ttg atc gat gat      336
Asn Thr Met Thr Glu Ser Glu Ala Glu Val Ser Ser Leu Ile Asp Asp
            100                 105                 110

ctt ggg ctt cgt gag aag caa cag ttg cca att tca caa aat aaa aga      384
Leu Gly Leu Arg Glu Lys Gln Gln Leu Pro Ile Ser Gln Asn Lys Arg
        115                 120                 125

tac ata gct aga gac ggt ctt cct gtg cta cta cct tca aat ccc gct      432
Tyr Ile Ala Arg Asp Gly Leu Pro Val Leu Leu Pro Ser Asn Pro Ala
    130                 135                 140

gca cta ctc acg agc aat atc ctt tca gca aaa tca aag ctg caa att      480
Ala Leu Leu Thr Ser Asn Ile Leu Ser Ala Lys Ser Lys Leu Gln Ile
145                 150                 155                 160

atg ttg gaa cca ttt ctc tgg aga aaa cac aat gct act gaa ctt tct      528
Met Leu Glu Pro Phe Leu Trp Arg Lys His Asn Ala Thr Glu Leu Ser
                165                 170                 175

gat gag cat gtt cag gaa agc gtt ggt gaa ttt ttt gag cga cat ttt      576
Asp Glu His Val Gln Glu Ser Val Gly Glu Phe Phe Glu Arg His Phe
            180                 185                 190

ggg aaa gag ttt gtt gat tat gtt atc gac cct ttt gtt gcg ggt aca      624
Gly Lys Glu Phe Val Asp Tyr Val Ile Asp Pro Phe Val Ala Gly Thr
        195                 200                 205

tgt ggt gga gat cct cga tcg ctt tcc atg cac cat aca ttt cca gaa      672
Cys Gly Gly Asp Pro Arg Ser Leu Ser Met His His Thr Phe Pro Glu
    210                 215                 220

gta tgg aat att gaa aaa agg ttt ggc tct gtg ttt gct gga cta att      720
Val Trp Asn Ile Glu Lys Arg Phe Gly Ser Val Phe Ala Gly Leu Ile
225                 230                 235                 240

caa tca aca ttg tta tct aag aag gaa aag ggt gga gaa aat gct tct      768
Gln Ser Thr Leu Leu Ser Lys Lys Glu Lys Gly Gly Glu Asn Ala Ser
                245                 250                 255

att aag aag cct cgt gta cgt ggt tca ttt tca ttt caa ggt gga atg      816
```

-continued

```
Ile Lys Lys Pro Arg Val Arg Gly Ser Phe Ser Phe Gln Gly Gly Met
            260                 265                 270

cag aca ctt gtt gac aca atg tgc aaa cag ctt ggt gaa gat gaa ctc      864
Gln Thr Leu Val Asp Thr Met Cys Lys Gln Leu Gly Glu Asp Glu Leu
        275                 280                 285

aaa ctc cag tgt gag gtg ctg tcc ttg tca tat aac cag aag ggg atc      912
Lys Leu Gln Cys Glu Val Leu Ser Leu Ser Tyr Asn Gln Lys Gly Ile
    290                 295                 300

ccc tca tta ggg aat tgg tca gtc tct tct atg tca aat aat acc agt      960
Pro Ser Leu Gly Asn Trp Ser Val Ser Ser Met Ser Asn Asn Thr Ser
305                 310                 315                 320

gaa gat caa tct tat gat gct gtg gtt gtc act gct cca att cgc aat     1008
Glu Asp Gln Ser Tyr Asp Ala Val Val Val Thr Ala Pro Ile Arg Asn
                325                 330                 335

gtc aaa gaa atg aag att atg aaa ttt gga aat cca ttt tca ctt gac     1056
Val Lys Glu Met Lys Ile Met Lys Phe Gly Asn Pro Phe Ser Leu Asp
            340                 345                 350

ttt att cca gag gtg acg tac gta ccc ctt tcc gtt atg att act gca     1104
Phe Ile Pro Glu Val Thr Tyr Val Pro Leu Ser Val Met Ile Thr Ala
        355                 360                 365

ttc aaa aag gat aaa gtg aag aga cct ctt gag ggc ttc gga gtt ctt     1152
Phe Lys Lys Asp Lys Val Lys Arg Pro Leu Glu Gly Phe Gly Val Leu
    370                 375                 380

atc ccc tct aaa gag caa cat aat gga ctg aag act ctt ggt act tta     1200
Ile Pro Ser Lys Glu Gln His Asn Gly Leu Lys Thr Leu Gly Thr Leu
385                 390                 395                 400

ttt tcc tcc atg atg ttt cct gat cgt gct cca tct gac atg tgt ctc     1248
Phe Ser Ser Met Met Phe Pro Asp Arg Ala Pro Ser Asp Met Cys Leu
                405                 410                 415

ttt act aca ttt gtc gga gga agc aga aat aga aaa ctt gca aac gct     1296
Phe Thr Thr Phe Val Gly Gly Ser Arg Asn Arg Lys Leu Ala Asn Ala
            420                 425                 430

tca acg gat gaa ttg aag caa ata gtt tct tct gac ctt cag cag ctg     1344
Ser Thr Asp Glu Leu Lys Gln Ile Val Ser Ser Asp Leu Gln Gln Leu
        435                 440                 445

ttg ggc act gag gac gaa cct tca ttt gtc aat cat ctc ttt tgg agc     1392
Leu Gly Thr Glu Asp Glu Pro Ser Phe Val Asn His Leu Phe Trp Ser
    450                 455                 460

aac gca ttc cca ttg tat gga cac aat tac gat tct gtt ttg aga gcc     1440
Asn Ala Phe Pro Leu Tyr Gly His Asn Tyr Asp Ser Val Leu Arg Ala
465                 470                 475                 480

ata gac aag atg gaa aag gat ctt cct gga ttt ttt tat gca ggt aac     1488
Ile Asp Lys Met Glu Lys Asp Leu Pro Gly Phe Phe Tyr Ala Gly Asn
                485                 490                 495

cat aag ggt gga ctt tca gtg gga aaa gcg atg gcc tcc gga tgc aag     1536
His Lys Gly Gly Leu Ser Val Gly Lys Ala Met Ala Ser Gly Cys Lys
            500                 505                 510

gct gcg gaa ctt gta ata tcc tat ctg gac tct cat ata tac gtg aag     1584
Ala Ala Glu Leu Val Ile Ser Tyr Leu Asp Ser His Ile Tyr Val Lys
        515                 520                 525

atg gat gag aag acc gcg taa                                         1605
Met Asp Glu Lys Thr Ala
    530

<210> SEQ ID NO 48
<211> LENGTH: 534
<212> TYPE: PRT
<213> ORGANISM: Amaranthus tuberculatus

<400> SEQUENCE: 48
```

-continued

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45

Val Gly Ala Gly Val Ser Gly Leu Ala Ala Ala Tyr Lys Leu Lys Ser
    50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
            100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
    130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
            180                 185                 190

Gly Lys Glu Phe Val Asp Tyr Val Ile Asp Pro Phe Val Ala Gly Thr
        195                 200                 205

Cys Gly Gly Asp Pro Arg Ser Leu Ser Met His His Thr Phe Pro Glu
    210                 215                 220

Val Trp Asn Ile Glu Lys Arg Phe Gly Ser Val Phe Ala Gly Leu Ile
225                 230                 235                 240

Gln Ser Thr Leu Leu Ser Lys Lys Glu Lys Gly Gly Glu Asn Ala Ser
                245                 250                 255

Ile Lys Lys Pro Arg Val Arg Gly Ser Phe Ser Phe Gln Gly Gly Met
            260                 265                 270

Gln Thr Leu Val Asp Thr Met Cys Lys Gln Leu Gly Glu Asp Glu Leu
        275                 280                 285

Lys Leu Gln Cys Glu Val Leu Ser Leu Ser Tyr Asn Gln Lys Gly Ile
    290                 295                 300

Pro Ser Leu Gly Asn Trp Ser Val Ser Ser Met Ser Asn Asn Thr Ser
305                 310                 315                 320

Glu Asp Gln Ser Tyr Asp Ala Val Val Val Thr Ala Pro Ile Arg Asn
                325                 330                 335

Val Lys Glu Met Lys Ile Met Lys Phe Gly Asn Pro Phe Ser Leu Asp
            340                 345                 350

Phe Ile Pro Glu Val Thr Tyr Val Pro Leu Ser Val Met Ile Thr Ala
        355                 360                 365

Phe Lys Lys Asp Lys Val Lys Arg Pro Leu Glu Gly Phe Gly Val Leu
    370                 375                 380

Ile Pro Ser Lys Glu Gln His Asn Gly Leu Lys Thr Leu Gly Thr Leu
385                 390                 395                 400

Phe Ser Ser Met Met Phe Pro Asp Arg Ala Pro Ser Asp Met Cys Leu
                405                 410                 415

Phe Thr Thr Phe Val Gly Gly Ser Arg Asn Arg Lys Leu Ala Asn Ala
```

-continued

```
            420                 425                 430

Ser Thr Asp Glu Leu Lys Gln Ile Val Ser Ser Asp Leu Gln Gln Leu
        435                 440                 445

Leu Gly Thr Glu Asp Glu Pro Ser Phe Val Asn His Leu Phe Trp Ser
    450                 455                 460

Asn Ala Phe Pro Leu Tyr Gly His Asn Tyr Asp Ser Val Leu Arg Ala
465                 470                 475                 480

Ile Asp Lys Met Glu Lys Asp Leu Pro Gly Phe Phe Tyr Ala Gly Asn
                485                 490                 495

His Lys Gly Gly Leu Ser Val Gly Lys Ala Met Ala Ser Gly Cys Lys
            500                 505                 510

Ala Ala Glu Leu Val Ile Ser Tyr Leu Asp Ser His Ile Tyr Val Lys
        515                 520                 525

Met Asp Glu Lys Thr Ala
    530


<210> SEQ ID NO 49
<211> LENGTH: 30
<212> TYPE: DNA
<213> ORGANISM: Artificial
<220> FEATURE:
<223> OTHER INFORMATION: Synthetic:  oligonucleotide useful as primer

<400> SEQUENCE: 49

ttgctcttcc atggtaattc aatccattac                                    30


<210> SEQ ID NO 50
<211> LENGTH: 32
<212> TYPE: DNA
<213> ORGANISM: Artificial
<220> FEATURE:
<223> OTHER INFORMATION: Synthetic:  oligonucleotide useful as primer

<400> SEQUENCE: 50

ttgctcttcg ttacgcggtc ttctcatcca tc                                 32


<210> SEQ ID NO 51
<211> LENGTH: 34
<212> TYPE: DNA
<213> ORGANISM: Artificial
<220> FEATURE:
<223> OTHER INFORMATION: Synthetic:  oligonucleotide useful as primer

<400> SEQUENCE: 51

catcgatcaa actcgagacc tctgcctcac tttc                               34


<210> SEQ ID NO 52
<211> LENGTH: 34
<212> TYPE: DNA
<213> ORGANISM: Artificial
<220> FEATURE:
<223> OTHER INFORMATION: Synthetic:  oligonucleotide useful as primer

<400> SEQUENCE: 52

gaggcagagg tctcgagttt gatcgatgat cttg                               34


<210> SEQ ID NO 53
<211> LENGTH: 38
<212> TYPE: DNA
<213> ORGANISM: Artificial
<220> FEATURE:
<223> OTHER INFORMATION: Synthetic:  oligonucleotide useful as primer
```

-continued

```
<400> SEQUENCE: 53

ttcaccaagc tgtttgcaca ttgtgtcaac aagtgtct                              38


<210> SEQ ID NO 54
<211> LENGTH: 38
<212> TYPE: DNA
<213> ORGANISM: Artificial
<220> FEATURE:
<223> OTHER INFORMATION: Synthetic:  oligonucleotide useful as primer

<400> SEQUENCE: 54

agacacttgt tgacacaatg tgcaaacagc ttggtgaa                              38
```

HERBICIDE RESISTANCE GENE, COMPOSITIONS AND METHODS

CROSS-REFERENCE TO RELATED APPLICATIONS

This application claims benefit of U.S. Provisional Application 60/807,780 filed Jul. 19, 2006 and of U.S. Provisional Application 60/711,204 filed Aug. 25, 2005; both of said applications are incorporated by reference herein to the extent there is no inconsistency with the present disclosure.

ACKNOWLEDGEMENT OF FEDERAL RESEARCH SUPPORT

Not applicable

BACKGROUND OF THE INVENTION

The field of the present invention is plant molecular biology, especially as related to genetically modified plants with resistance to herbicide. Specifically, the present invention relates to transgenic plants in which herbicide resistance is achieved by introducing a coding sequence which determines an herbicide resistance protoporphyrinogen oxidase (PPO) which is expressed in chloroplasts and mitochondria. Such transgenic crop plants are useful in fields where it is desired to spray herbicide to improve crop yield.

A major concern with the use of herbicides for weed control is the selection of resistant populations. To date, over 300 different herbicide-resistant weed biotypes have been identified worldwide (see weedscience.com on the internet). Numerous factors influence the likelihood of herbicide-resistance evolution in a weed population, and certain herbicides are more prone to resistance evolution than are others. For example, populations of 95 weed species have been reported with resistance to herbicides that inhibit acetolactate synthase (ALS), whereas evolved resistance to herbicides that inhibit protoporphyrinogen oxidase (PPO) has been reported for only three weeds (weedscience.com website), even though these herbicides were first commercialized in the 1960s (1). The first weed to evolve resistance to PPO inhibitors was *Amaranthus tuberculatus* (waterhemp), an increasingly problematic weed of agronomic production systems throughout the Midwestern United States.

The biosynthetic pathways which lead to the production of chlorophyll and heme share a number of common steps. Chlorophyll is a light harvesting pigment present in all green photosynthetic organisms. Heme is a cofactor of hemoglobin, cytochromes, P450 mixed-function oxygenases, peroxidases, and catalases (see, eg. Lehninger, 1975, Biochemistry. Worth Publishers, New York), and is therefore a necessary component for all aerobic organisms. The last common step in chlorophyll and heme biosynthesis is the oxidation of protoporphyrinogen IX to protoporphyrin IX. Protoporphyrinogen oxidase (referred to herein as PPO or protox) is the enzyme which catalyzes this last oxidation step (Matringe et al. 1989. Biochem. J. 260: 231).

An approach that has been used to isolate biosynthetic genes in metabolic pathways from organisms including the higher eukaryotes is the complementation of microbial (auxotrophic) mutants deficient in the activity of interest. For this approach, a library of cDNAs from the higher eukaryote is cloned in a vector that can direct expression of the cDNA in the microbial host. The vector is then transformed or otherwise introduced into the mutant, and colonies are selected that no longer require the nutritional supplementation of interest. Microbial mutants believed defective in PPO activity have been described (e.g. *E. coli* (Sasarman et al. 1979. J. Gen. Microbiol. 113: 297), *Salmonella typhimurium* (Xu et al. 1992. J. Bacteriol. 174: 3953), and *Saccharomyces cerevisiae* (Camadro et al. 1982. Biochem. Biophys. Res. Comm. 106: 724.

The use of herbicides to control undesirable vegetation such as weeds or plants in crops has become common, with the relevant market exceeding a billion dollars a year. Despite extensive herbicide use, weed control remains a significant and costly problem for farmers. Since various weed species are resistant to herbicides, the production of effective herbicides becomes increasingly important, as is the development of agronomically important plants which are resistant to one or more herbicides.

The PPO enzyme is the target of a variety of herbicides. PPO-inhibiting herbicides include many different structural classes of molecules (Duke et al. 1991. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70). These herbicidal compounds include the diphenylethers {e.g. lactofen, (±)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. Many of these compounds competitively inhibit the normal reaction catalyzed by the enzyme, apparently acting as substrate analogs.

Additional herbicides of interest include 3-Phenyluracils of formula I (I)

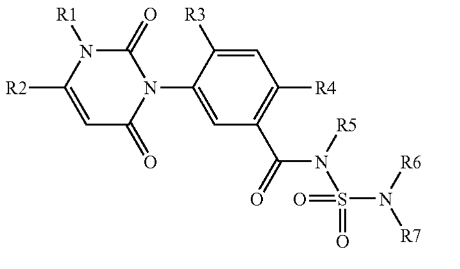

wherein $R^1$ is methyl or $NH_2$; $R^2$ is $C_1$-$C_2$-haloalkyl; $R^3$ is hydrogen or halogen; $R^4$ is halogen or cyano; $R^5$ is hydrogen, cyano, $C_1$-$C_6$-alkyl, $C_1$-$C_6$-alkoxy, $C_1$-$C_4$-alkoxy-$C_1$-$C_4$-alkyl, $C_3$-$C_7$-cycloalkyl, $C_3$-$C_6$-alkenyl, $C_3$-$C_6$-alkynyl or benzyl which is unsubstituted or substituted by halogen or alkyl; and $R^6$, $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_7$-cycloalkyl, $C_3$-$C_7$-cycloalkenyl, phenyl or benzyl, where each of the 8 abovementioned substituents is unsubstituted or may be substituted by 1 to 6 halogen atoms and/or by one, two or three groups selected from: OH, $NH_2$, CN, $CONH_2$, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylamino, di($C_1$-$C_4$-alkyl)amino, formyl, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, $C_3$-$C_7$-cycloalkyl, phenyl and benzyl; or $R^6$, $R^7$ together with the nitrogen atom form a 3-, 4-, 5-, 6- or 7-membered saturated or unsaturated nitrogen heterocycle which may be substituted by 1 to 6 methyl groups and which may contain 1 or 2 further heteroatoms selected from the group consisting of nitrogen, oxygen and sulfur as ring members, and their agriculturally acceptable salts (as described in the patent application PCT/EP 01/04850.

Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death (Lee et al. 1993. Plant Physiol. 102: 881).

Not all PPO enzymes are sensitive to herbicides which inhibit plant PPO enzymes. Both the *Escherichia coli* and *Bacillus subtilis* PPO enzymes (Sasarmen et al. 1993. Can. J. Microbiol. 39: 1155; Dailey et al. 1994. J. Biol. Chem. 269: 813) are resistant to these herbicidal inhibitors. Mutants of the unicellular alga *Chlamydomonas reinhardtii* resistant to the phenylimide herbicide S-23142 have been reported (Kataoka et al. 1990. J. Pesticide Sci. 15: 449; Shibata et al. 1992. In Research in Photosynthesis, Vol. III, N. Murata, ed. Kluwer: Netherlands. pp. 567-570). At least one of these mutants appears to have an altered PPO activity that is resistant not only to the herbicidal inhibitor on which the mutant was selected, but also to other classes of protox inhibitors (Oshio et al. 1993. Z. Naturforsch. 48c: 339; Sato et al. 1994. In ACS Symposium on Porphyric Pesticides, S. Duke, ed. ACS Press: Washington, D.C.). A mutant tobacco cell line has also been reported that is resistant to the inhibitor S-21432 (Che et al. 1993. Z. Naturforsch. 48c: 350). Auxotrophic *E. coli* mutants have been used to confirm the herbicide resistance of cloned plant PPOs.

There is a need in the art for effective and efficient herbicide resistance genes in plants, especially crop plants, so that application of herbicide to cultivated fields results in good growth of the desired crop plants and eradication (or significant reduction) in pest plants.

SUMMARY OF THE INVENTION

The present invention provides a DNA construct comprising coding sequence for an herbicide resistant protoporphyrinogen oxidase (PPO) enzyme operably linked to a transcription regulatory sequence, especially one from a plant, and advantageously, a strong constitutive transcription regulatory sequence from a plant. A consensus sequence of an herbicide resistant PPO coding sequence is derived from *Amaranthus tuberculatus* and is presented in SEQ ID NO:13, and the consensus amino acid sequence is given in SEQ ID NO:14. Specifically exemplified sequences isolated from herbicide resistant *A. tuberculatus* are disclosed herein; see also SEQ ID NOs:13 and 14, 25 and 26, 29 and 30, and 45 and 46. The wild type (herbicide sensitive) *A. tuberculatus* coding and protein sequences are shown in SEQ ID NO:15 and SEQ ID NO:16; other herbicide-sensitive PPXL2 sequences are given in SEQ ID NOs: 21-22 and 27-28. Also within the scope of this invention are isolated nucleic acid molecules and vectors (plasmid or virus) comprising the herbicide resistant PPO coding sequences of the present invention, advantageously operably linked to transcription regulatory sequences. The critical feature of an herbicide resistant PPO enzyme of the present invention is a deletion of a glycine residue at amino acid 210 or 211, with reference to SEQ ID NO:16. See also FIG. 10B for various amino acid sequence polymorphisms that can be present in the Glycine 210 deleted PPO, without loss of either enzymatic function or herbicide resistance. It is understood that there can be limited sequence variation from the specifically exemplified herbicide resistant sequences or consensus sequences, provided that the glycine deletion at a position corresponding to or aligned with position 210 or 211 of SEQ ID NO:16 is maintained, especially where there is are from one to five amino acid substitutions, deletions or insertions and where the enzymatic activity of the enzyme is not eliminated.

Plants expressing the herbicide resistant PPX2L proteins of the present invention are believed to be significantly improved in resistance over certain prior art herbicide resistant PPX2L proteins. In contrast to the corresponding wild type PPO, the resistant PPO of the present invention exhibits reduced sensitivity to PPO-inhibiting herbicides including lactofen, acifluorfen, flumiclorac, fomesafen, flumioxazin, and sulfentrazone. All synonymous sequences encoding the resistant PPO described herein are encompassed by the present invention.

The present invention further provides recombinant plant cells, recombinant plant tissue, transgenic plants and transgenic plant seed which contain the DNA constructs of the present invention. Transgenic plants which contain the DNA construct are resistant to killing and/or growth inhibition by protoporphyrinogen-IX oxidase-inhibiting herbicides including, but not limited to, lactofen, acifluorfen, flumiclorac, fomesafen, flumioxazin, sulfentrazone, bifenox, chlomethoxyfen, chlornitrofen, ethoxyfen, fluorodifen, fluoroglycofen, fluoronitrofen, furyloxyfen, halosafen, nitrofen, nitrofluorfen, oxyfluorfen, fluazolate, pyraflufen, cinidon-ethyl, flumipropyn, fluthiacet, thidiazimin, oxadiazon, oxadiargyl, azafenidin, carfentrazone, pentoxazone, benzfendizone, butafenacil, pyraclonil, profluazol, flufenpyr, flupropacil, nipyraclofen and etnipromid, as well as other herbicides discussed herein, including 3-phenyluracils of Formula I given herein above.

Also within the scope of the present invention are methods for rendering a plant of interest resistant to PPO-inhibiting herbicides. The method of the present invention comprises the steps of introducing a vector comprising a DNA construct containing a constitutive transcriptional regulatory sequence (active in a plant) operably linked to a coding sequence for an herbicide resistant PPO of the present invention into a plant cell or tissue to produce a transgenic plant cell or transgenic plant tissue which is resistant to PPO-inhibiting herbicides including, but not limited to, lactofen, acifluorfen, flumiclorac, fomesafen, flumioxazin, bifenox, chlomethoxyfen, chlornitrofen, ethoxyfen, fluorodifen, sulfentrazone, fluoroglycofen, fluoronitrofen, furyloxyfen, halosafen, lactofen, nitrofen, nitrofluorfen, oxyfluorfen, fluazolate, pyraflufen, cinidon-ethyl, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid and to the herbicidal 3-phenyluracils disclosed herein above.

In addition, the present invention provides methods for selecting or screening for a genetic modification event, for example transformation, via the expression of the PPO-inhibiting herbicide resistant coding sequence of the present invention after introduction into a cell or tissue of interest the coding sequence operably linked to transcription control sequences functional in that cell or tissue.

The present invention further encompasses transgenic plants expressing an herbicide resistant PPX2L coding sequence as disclosed herein. For the specifically exemplified coding sequences, see SEQ ID NOs: 13, 25, 29 and 45. Specifically exemplified herbicide-resistant PPO enzymes of the present invention include those of SEQ ID NOs: 14, 26 and 30.

Also within the scope of the present invention are cultivated *Amaranthus* species (including, but not limited to, *A. hypochondriacus, A. cruentus, A. caudatus, A. dubius*, and *A. tricolor*) into which the herbicide resistant PPO gene from the weed *A. tuberculatus* has been introduced by conventional plant breeding and selection techniques. Other crops of interest into which a herbicide resistant PPO gene of the present invention can be introduced include, without limitation, cotton, corn, wheat, rice, oats, barley, vegetables including crucifers (cabbage, Brussels sprouts, kale, kohl rabi, broccoli and the like), tomatoes, potatoes, sunflowers, peppers, eggplants, stone fruits, berries, grapes, apples, pears, and ornamental plants including roses, shrubs, turf and grasses.

Additional embodiments of the invention relate to transformed seeds and transgenic progeny plants of the parent transgenic plant of the invention and the use of said plants, seeds, and plant parts in the agro-industry and/or in the production of food, feed, industrial products, oil, nutrients, and other valuable products. Preferably, these other embodiment of the invention relates to transformed seed of such a plant, method for breeding other plants using said plant, use of said plant in breeding or agriculture, and use of said plant to produce chemicals, food or feed products.

Also within the scope of the present invention are methods for controlling the growth of unwanted plants amongst crop or other plants containing and expressing a PPO-inhibiting herbicide resistant PPX2L coding sequence of the present invention, where the crop or other plants are cultivated and sprayed with a PPO-inhibiting herbicide, with the result that the unwanted plants, which are naturally sensitive to a PPO-inhibiting herbicide, are killed or retarded in growth. Thus, the crop or other plants of interest grow with greater efficiency and with less competition for nutrients, sunlight and water from unwanted species.

BRIEF DESCRIPTION OF THE DRAWINGS

FIG. 7 provides translated PPX2L amino acid sequences from *A. tuberculatus*. Amino acid differences are indicated by "*". Amino acid position 210 (black boxes) is the only difference that correlates with R or S responses to lactofen (GenBank accessions DQ386114, DQ386117, DQ386116, and DQ386118 and SEQ ID NO:22, 28, 26 and 30, respectively).

FIGS. 10-10B provides a summary of positions within the *A. tuberculatus* PPX2L coding sequence which can be varied without either loss of function and without affecting herbicide resistance. In FIG. 10A the reference sequence is SEQ ID NO:15 (herbicide sensitive PPX2L), and in FIG. 10B, SEQ ID NO:13 (herbicide resistant PPX2L) Such varied sequences represent polymorphisms.

DETAILED DESCRIPTION OF THE INVENTION

Figure 1:
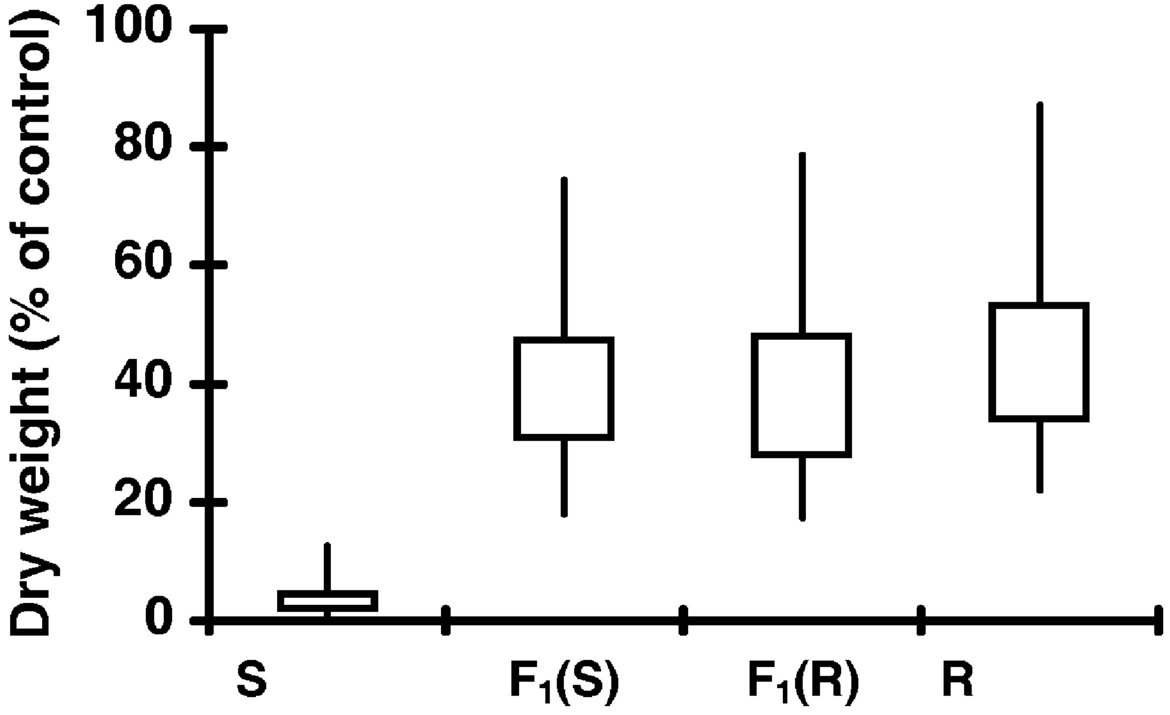
FIG. 1 shows Lactofen responses of the protoporphyrinogen oxidase inhibitor-susceptible parent (S), -resistant parent (R), hybrid where the maternal parent was R {$F_1$(R)}, or hybrid where the maternal parent was S {$F_1$(S)}. Waterhemp plants were harvested 15 days after treatment with lactofen at 110 g ai $ha^{-1}$ plus 1% (by vol) Crop Oil Concentrate (COC). Boxes represent the $25^{th}$ to $75^{th}$ percentile of responses, while whiskers include the remaining quartiles (n=100).

Despite being used to control weeds in agricultural crops for the past 30 years, the mode-of-action of herbicides inhibiting protoporphyrinogen oxidase (PPO) was mostly unknown for the first 20 years of their use. Multiple chemical structures inhibit PPO, with the diphenylethers, triazolinones, and N-phenyl-phthalimides being the major families used in crop production.

PPO is the last common enzyme in the tetrapyrrole biosynthetic pathway that produces heme and chlorophyll (Beale and Weinstein 1990). In plants, chlorophyll biosynthesis takes place exclusively in chloroplasts, while heme is produced in both plastids and mitochondria (Smith et al. 1993;

Chow et al. 1997). The tetrapyrrole biosynthetic pathway in plants begins with the formation of 5-aminolevulinic acid (ALA) from the C5-skeleton of glutamate. Eight molecules of ALA are combined to form protoporphyrinogen IX (protogen IX) (Papenbrock and Grimm 2001). Protogen IX is converted to protoporphyrin IX (proto IX) in both chloroplasts and mitochondria by the activity of PPO (Jacobs and Jacobs 1984). Studies conducted by Matringe et al. (1992) provided evidence that two constitutive PPO activities are found in chloroplasts: one associated with envelope membranes and another with thylakoid membranes. In mitochondria, PPO is associated exclusively with the envelope membranes (Deybach et al. 1985).

The genes that encode either plastid PPO (PPX1) or mitochondrial PPO (PPX2) have recently been cloned and sequenced from several plant species (Lermontova et al. 1997; Watanabe et al. 2001). Both PPX1 and PPX2 are nuclear encoded genes whose translation products must be imported into plastids or mitochondria, respectively. Interestingly, the translated product of PPX2 from spinach has been identified in two isoforms of different length due to the existence of dual in-frame initiation codons (Watanabe et al. 2001). The longer version of PPX2 includes a sequence encoding a chloroplast transit peptide, while the shorter version encodes a targeting sequence for import into the mitochondria.

When susceptible plants are treated with PPO inhibitors, the substrate of PPO, protogen IX, accumulates and is exported from the plastid to the cytoplasm (Kojima et al. 1991; Jacobs and Jacobs 1993) where herbicidally insensitive peroxidase-like enzymes in the plasma membrane convert it to proto IX (Lee et al. 1993; Lee and Duke 1994; Retzlaff and Böger 1996). Proto IX accumulates in the cytoplasm, and in the presence of light, induces the formation of singlet oxygen (Cox and Whitten 1983) that is damaging to cell membranes. Symptomatology following PPO inhibitor treatment occurs rapidly in the presence of light, with water soaked lesions and tissue necrosis appearing within hours after treatment (Dayan and Duke 1997).

Plants or plant cells resistant to PPO inhibitors have been generated by tissue culture selection (Horikoshi and Hirooka 1999; Pornprom et al. 1994; Wantanabe et al. 1998) and genetic engineering (Choi et al. 1998; Lee et al. 2000; Lermontova and Grimm 2000). Acifluorfen-resistant mutants of *Arabidopsis thaliana* have also been reported (Duke et al. 1997); however, no characterization related to resistance has been reported. Considerable effort has been devoted to the development of PPO inhibitor-resistant crops (Reviewed by Li and Nicholl 2005), but none have been commercialized.

PPO inhibitor resistance in waterhemp was first documented in Kansas during the summer of 2000 (Shoup et al. 2003). In Illinois, a waterhemp biotype resistant to PPO inhibitors was first identified during the summer of 2001 (Patzoldt et al. 2005). According to Dayan and Duke (1997), resistance to PPO-inhibiting herbicides can be achieved by one of six predicted methods: 1) reduced herbicide uptake, 2) enhanced herbicide metabolism before reaching its site of action, 3) altered herbicide site of action, 4) removal or degradation of protogen 1× from the cytoplasm before it can be converted to proto IX, 5) inactivated extraplastidic PPO-like enzymes, and 6) sequestration of singlet oxygen and other toxic species. Other mechanisms of PPO inhibitor resistance might also be: 7) over-expression of the plastid form of PPO (Lermontova and Grimm 2000) and 8) over-expression of the mitochondrial form of PPO (Watanabe et al. 1998). Numerous structurally diverse compounds inhibit PPO, indicating that this herbicide target site is highly variable, similar to the target sites of herbicides that inhibit ALS or acetyl-CoA carboxylase (ACCase) (Duke et al. 1997). Currently, at least 18 amino acid substitutions have been identified within PPO that confer resistance to PPO-inhibiting herbicides (Volrath et al. 1999).

Waterhemp is the first weed species to have been selected for resistance to PPO inhibitors; thus it provides a unique opportunity for characterization of herbicide resistance mechanisms in plants. Therefore, the objectives of this study related to PPO inhibitor resistance were determine the inheritance, calculate the degree of dominance, and determine the mechanism of resistance in waterhemp.

As used herein, an herbicide resistant plant is one which germinates from a seed and grows in the concentration of pesticide where the comparison wild-type plant does not grow and/or does not germinate. The germination and growth of the resistant plant is similar in the presence or absence of the relevant PPO-inhibiting herbicide.

For recombinant production of the enzyme in a host organism, the PPO coding sequence is inserted into an expression cassette designed for the chosen host and introduced into the host where it is recombinantly produced. The choice of specific regulatory sequences such as promoter, signal sequence, 5' and 3' untranslated sequences, and enhancer, is within the level of skill of the one ordinarily skilled in the art. The resultant molecule, containing the individual elements linked in proper orientation and reading frame, may be inserted into a vector capable of being transformed into the host cell. Suitable expression vectors and methods for recombinant production of proteins are well known for host organisms such as *E. coli* (see, e.g. Studier and Moffatt. 1986. J. Mol. Biol. 189: 113; Brosius. 1989. DNA 8: 759), yeast (see, e.g., Schneider and Guarente. 1991. Meth. Enzymol. 194: 373) and insect cells (see, e.g. Luckow and Summers. 1988. Bio/Technol. 6: 47). Specific examples include plasmids such as pBluescript (Stratagene, La Jolla, Calif.), PFLAG (International Biotechnologies, Inc., New Haven, Conn.), pTrcHis (Invitrogen, Carlsbad, Calif.), and baculovirus expression vectors, e.g., those derived from the genome of *Autographica californía* nuclear polyhedrosis virus (AcMNPV). A preferred baculovirus/insect system is pV111392/Sf21 cells (Invitrogen, Carlsbad, Calif.).

A recombinantly produced herbicide resistant PPO of the present invention is useful for a variety of purposes, including, but not limited to, in an in vitro assay to screen known herbicidal compounds to determine if they inhibit this PPO, in an in vitro general screening assay to identify chemicals which do or do not inhibit the mutant PPO, or to characterize its association with known inhibitors in order to rationally design new inhibitory herbicides as well as herbicide tolerant forms of the enzyme.

The inhibitory effect on PPO can be determined by measuring fluorescence at about 622 to 635 nm, after excitation at about 395 to 410 nM (see, e.g. Jacobs and Jacobs. 1982. Enyzme 28: 206; Sherman et al. 1991. Plant Physiol. 97. 280). Protoporphyrin IX is a fluorescent pigment; protoporphyrinogen IX is not fluorescent. Protein extracts are prepared from selected subcellular fractions, e.g. etioplasts, mitochondria, microsomes, or plasma membrane, by differential centrifugation (see, e.g. Lee et al. 1993. Plant Physiol. 102:881; Prado et al. 1979. Plant Physiol. 65: 956; Jackson and Moore, in Plant Organelles, Reid, ed., pp. 1-12; Jacobs and Jacobs. 1993. Plant Physiol. 101: 1181). Protoporphyrinogen is prepared by reduction of protoporphyrin with a sodium amalgam as described by Jacobs and Jacobs (1982). Reactions mixtures typically consist of 100 mM Hepes (pH 7.5), 5 mM EDTA, 2 mM DTT, about 2 μM protoporphyrinogen IX, and about 1 mg/mL protein extract. Inhibitor solutions in various concentrations, e.g. 1 mM, 100 μM, 10 μM, 1 μM, 100 nM, 10 nM, 1 nM, 100 pM, are added to the enzyme extract prior to the initiation of the enzyme reaction. Once the protein extract is added, fluorescence is monitored for several minutes, and the slope of the slope (reaction rate) is calculated from a region of linearity. $IC_{50}$ is determined by comparing the slope of the inhibited reaction to a control reaction, and $IC_{50}$ is the concentration of herbicide at which the reaction rate of the wild type enzyme is reduced by 50%.

Herbicides that inhibit wild type PPO enzymes include many different structural classes of molecules (Duke et al. 9119. Weed Sci. 39: 465; Nandihalli et al. 1992. Pesticide Biochem. Physiol. 43: 193; Matringe et al. 1989. FEBS Lett. 245: 35; Yanase and Andoh. 1989. Pesticide Biochem. Physiol. 35: 70), including the diphenylethers (e.g. acifluorifen, 5-{2-chloro-4-(trifluoromethyl)phenoxy}-2-nitrobezoic acid; its methyl ester; or oxyfluorfen, 2-chloro-1-(3-ethoxy-4-nitrophenoxy)-4-(trifluorobenzene)), oxidiazoles (e.g. oxidiazon, 3-{2,4-dichloro-5-(1-methylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), and phenopylate and its O-phenylpyrrolidino- and piperidinocarbamate analogs. The herbicidal activity of the above compounds is described in the Proceedings of the 1991 Brighton Crop Protection Conference, Weeds (British Crop Protection Council), Proceedings of the 1993 Brighton Crop Protection Conference, Weeds (British Crop Protection Council), U.S. Pat. Nos. 4,746,352 and 1993 Abstracts of the Weed Science Society of America vol. 33, pg. 9.

The imide herbicides include those classified as aryluracils and having the general formula wherein R signifies the group ($C_{2-6}$-alkenyloxy)carbonyl-$C_{1-4}$-alkyl, as disclosed in U.S. Pat. No. 5,183,492. See also WO 94/08999, WO 93/10100, and U.S. Pat. No. 5,405,829 assigned to Schering; N-phenylpyrazoles, 3-substituted-2-aryl-4,5,6,7-tetrahydroindazoles (Lyga et al. 1994. Pesticide Sci. 42:29-36).

Additional herbicides for which resistant crops and resistant ornamental plants are needed include those listed in Paragraph [0008] the 3-phenyl uracils, such as those of Formula I as defined herein above.

Effective application rates of herbicide which normally are inhibitory to the activity of PPO are known in the art, for example, 0.0001 to 10 kg/ha, preferably from 0.005 to 2 kg/ha. Rates depend, at least in part, on external factors such as environment, time and method of application. This dosage rate or concentration of herbicide depends on the desired action and particular compound used, and can be determined by methods known in the art.

The present invention is further directed to transgenic plants, transgenic progeny plants, transgenic seeds, transgenic cells and transgenic plant tissue resistant to herbicides that inhibit the naturally occurring PPO activity in these plants, wherein the tolerance is conferred by an herbicide resistant PPO enzyme of the present invention. Representative plants include any plants to which these herbicides are applied for their normally intended purpose, especially agronomically important angiosperms and gymnosperms, including but not limited to, cotton, soya, rape, sugar beet, maize, rice, wheat, barley, oats, rye, sorghum, millet, forage, turf grasses, berries, vegetables, stone fruits, grapevines, apples, pears, ornamental plants, tree species and the like.

In the context of the present invention, an "herbicide resistant PPO" is a PPO activity different from that which occurs in a wild-type (herbicide-sensitive). Such a resistant PPO is one which is not inhibited significantly (more than 90%) by a "PPO-inhibiting" herbicide set forth herein.

Plants expressing the herbicide resistant PPO can be obtained by stably transforming an herbicide resistant PPO coding sequence of the present invention into a plant cell such that it is expressed in the above-ground plant tissues, and preferably in all plant tissues, and it stably maintained in the plant. Herbicide resistant PPO coding sequences can be obtained or identified by complementing a bacterial or yeast auxotrophic mutant with a cDNA expression library from the target plant. Alternatively, an herbicide sensitive PPX2L coding sequence can be converted to encode the resistant phenotype by site-directed mutagenesis to delete one of the two contiguous glycine codons for amino acid residues 210-211 of SEQ ID NO:16 or a functional equivalent thereof.

The herbicide resistant PPO sequence of the present invention was obtained by cloning a PPO gene from a plant that was naturally resistant to PPO-inhibiting herbicides including lactofen, acifluorfen, flumiclorac, fomesafen, flumioxazin, and sulfentrazone. Specifically, a population of waterhemp was identified that was no longer effectively controlled by PPO-inhibiting herbicides.

Examples of constitutive promoters which function in plant cells include the cauliflower mosaic virus (CaMV) 19S or 35S promoters, CaMV 35S double or enhanced promoters, the 35S promoter and an enhanced or double 35S promoter such as that described in Kay et al., Science 236: 1299-1302 (1987); nopaline synthase promoter; pathogenesis-related (PR) protein promoters, the rice actin promoter (McElroy et al. 1991. Mol. Gen. Genet. 231: 150), maize ubiquitin promoter (EP 0 342 926; Taylor et al. 1993. Plant Cell Rep. 12: 491), and the Pr-1 promoter from tobacco, *Arabidopsis*, or maize (see U.S. Pat. No. 5,614,395), the peanut chlorotic streak caulimovirus (PCISV) promoter (U.S. Pat. No. 5,850,019), the 35S promoter from cauliflower mosaic virus (CaMV) (Odell et al. 1985. Nature 313:810-812), promoters of Chlorella virus methyltransferase genes (U.S. Pat. No. 5,563,328), the full-length transcript promoter from figwort mosaic virus (FMV) (U.S. Pat. No. 5,378,619); the promoters from such genes as rice actin (McElroy et al. 1990. Plant Cell 2:163-171), ubiquitin (Christensen et al. 1989. Plant Mol. Biol. 12:619-632) and Christensen et al. 1992. Plant Mol. Biol. 18:675-689), PEMU (Last et al. 1991. Theor. Appl. Genet. 81:581-588), MAS (Velten et al. 1984. EMBO J. 3:2723-2730), maize H3 histone (Lepetit et al. 1992. Mol. Gen. Genet. 231:276-285 and Atanassova et al. 1992. Plant Journal 2(3):291-300), *Brassica napus* ALS3 (WO 97/41228); and promoters of various *Agrobacterium* genes (see, e.g., U.S. Pat. Nos. 4,771,002, 5,102,796, 5,182,200 and 5,428,147). Light-regulated promoters suitable for expression in above-ground tissues include the small subunit of ribulose bisphosphate carboxylase (ssuRUBISCO) promoter and the like. The promoters themselves may be modified to manipulate promoter strength to increase herbicide resistant PPO expression, in accordance with art-recognized procedures.

Guidance for the design of promoters is provided by studies of promoter structure, such as that of Harley and Reynolds. 1987. Nucleic Acids Res. 15:2343-2361). Also, the location of the promoter relative to the transcription start may be optimized. See, e.g., Roberts, et al. 1979. Proc. Natl. Acad. Sci. USA 76:760-4. Many suitable promoters for use in plants are well known in the art.

Suitable inducible promoters for use in plants include: the promoter from the ACE1 system which responds to copper (Mett et al. 1993. PNAS 90:4567-4571); the promoter of the maize In2 gene which responds to benzenesulfonamide herbicide safeners (Hershey et al. 1991. Mol. Gen. Genetics 227:229-237) and Gatz et al. 1994. Mol. Gen. Genetics 243: 32-38), and the promoter of the Tet repressor gene from Tn10 (Gatz et al. 1991. Mol. Gen. Genet. 227:229-237). A particularly preferred inducible promoter for use in plants is one that responds to an inducing agent to which plants do not normally respond. An exemplary inducible promoter of this type is the inducible promoter from a steroid hormone gene, the transcriptional activity of which is induced by a glucocorticosteroid hormone (Schena et al. 1991. Proc. Natl. Acad. Sci. USA 88:10421) or the recent application of a chimeric transcription activator, XVE, for use in an estrogen receptor-based inducible plant expression system activated by estradiol (Zuo et al. 2000. The Plant Journal 24:265-273). Other inducible promoters for use in plants are described in, e.g., EP 332104, PCT WO 93/21334 and PCT WO 97/06269. Plant promoters composed of portions of other promoters and partially or totally synthetic promoters can also be used; see, e.g., Ni et al. 1995. Plant J. 7:661-676; WO 95/14098.

The promoter may include or be modified to include one or more enhancer elements. Promoters with enhancer elements provide for higher levels of transcription as compared to promoters without them. Suitable enhancer elements for use in plants include the PCISV enhancer element (U.S. Pat. No. 5,850,019), the CaMV 35S enhancer element (U.S. Pat. Nos. 5,106,739 and 5,164,316) and the FMV enhancer element (Maiti et al. 1997. Transgenic Res. 6:143-156). See also WO 96/23898 and Enhancers and Eukaryotic Expression (Cold Spring Harbor Press, Cold Spring Harbor, N.Y., 1983).

A 5' untranslated sequence is also employed. The 5' untranslated sequence is the portion of an mRNA which extends from the 5' CAP site to the translation initiation codon. This region of the mRNA is necessary for translation initiation in plants and plays a role in the regulation of gene expression. Suitable 5' untranslated regions for use in plants include those of alfalfa mosaic virus, cucumber mosaic virus coat protein gene, and tobacco mosaic virus.

For efficient expression, the coding sequences are preferably also operatively linked to a 3' untranslated sequence. The 3' untranslated sequence will include a transcription termination sequence and a polyadenylation sequence. The 3' untranslated region can be obtained from the flanking regions of genes from *Agrobacterium*, plant viruses, plants or other eukaryotes. Suitable 3' untranslated sequences for use in plants include those of the cauliflower mosaic virus 35S gene, the phaseolin seed storage protein gene, the pea ribulose biphosphate carboxylase small subunit E9 gene, the soybean 7S storage protein genes, the octopine synthase gene, and the nopaline synthase gene.

The PPO gene of the present invention contains both chloroplast and mitochondrial transit peptides. Others known to the art can be substituted, if deemed advantageous.

The chimeric DNA construct(s) (non-naturally occurring nucleic acid molecules) of the invention may contain multiple copies of a promoter or multiple copies of the herbicide resistant PPO coding sequence of the present invention. In addition, the construct(s) may include coding sequences for selectable or detectable markers, each in proper reading frame with the other functional elements in the DNA molecule. The preparation of such constructs is within the ordinary level of skill in the art.

The DNA construct may be a vector. The vector may contain one or more replication systems which allow it to replicate in host cells. Self-replicating vectors include plasmids, cosmids and viral vectors. Alternatively, the vector may be an integrating vector which allows the integration into the host cell's chromosome of the DNA sequence encoding the herbicide resistant PPO. The vector desirably also has unique restriction sites for the insertion of DNA sequences. If a vector does not have unique restriction sites, it may be modified to introduce or eliminate restriction sites to make it more suitable for further manipulations.

The DNA constructs of the invention can be used to transform any type of plant cells (see below). A genetic marker must be used for selecting transformed plant cells (a selection marker). Selection markers typically allow transformed cells to be recovered by negative selection (i.e., inhibiting growth of cells that do not contain the selection marker) or by screening for a product encoded by the selection marker.

The most commonly used selectable marker gene for plant transformation is the neomycin phosphotransferase II (nptII) gene, isolated from Tn5, which, when placed under the control of plant expression control signals, confers resistance to kanamycin (Fraley et al. 1983. Proc. Natl. Acad. Sci. USA 80:4803). Another commonly used selectable marker gene is the hygromycin phosphotransferase gene which confers resistance to the antibiotic hygromycin. Vanden Elzen et al. 1995. Plant Mol. Biol. 5:299). Additional selectable marker genes of bacterial origin that confer resistance to antibiotics include gentamicin acetyl transferase, streptomycin phosphotransferase, aminoglycoside-3'-adenyl transferase, and the bleomycin resistance determinant (Hayford et al. 1988. Plant Physiol. 86:1216; Jones et al. 1987. Mol. Gen. Genet. 210:86; Svab et al. 1990. Plant Mol. Biol. 14:197; Hille et al. 1986. Plant Mol. Biol. 7:171). Other selectable marker genes confer resistance to herbicides such as glyphosate, glufosinate or bromoxynil (Comai et al. 1985. Nature 317:741-744; Stalker et al. 1988. Science 242:419-423; Hinchee et al. 1988. Bio/Technology 6:915-922; Stalker et al. 1988. J. Biol. Chem. 263:6310-6314; Gordon-Kamm et al. 1990. Plant Cell 2:603-618).

Other selectable markers useful for plant transformation include, without limitation, mouse dihydrofolate reductase, plant 5-enolpyruvylshikimate-3-phosphate synthase, and plant acetolactate synthase (Eichholtz et al. 1987. Somatic Cell Mol. Genet. 13:67; Shah et al. 1986. Science 233:478; Charest et al. 1990. Plant Cell Rep. 8:643; EP 154,204), and herbicide resistance markers including, or other than, the PPO derivatives of the present invention.

Commonly used genes for screening presumptively transformed cells include but are not limited to β-glucuronidase (GUS), β-galactosidase, luciferase, and chloramphenicol acetyltransferase (Jefferson, R. A. 1987. Plant Mol. Biol. Rep. 5:387; Teeri et al. 1989. EMBO J. 8:343; Koncz et al. 1987. Proc. Natl. Acad. Sci. USA 84:131; De Block et al. 1984. EMBO J. 3:1681), green fluorescent protein (GFP) (Chalfie et al. 1994. Science 263:802; Haseloff et al. 1995. TIG 11:328-329 and PCT application WO 97/41228). Another approach to the identification of relatively rare transformation events has been use of a gene that encodes a dominant constitutive regulator of the *Zea mays* anthocyanin pigmentation pathway (Ludwig et al. 1990. Science 247:449).

The level of resistance of a particular resistant PPO can be tested using transgenic plant cells, transgenic plant tissue (such as callus, for example) or transgenic plant. Resistance can also be confirmed using direct selection in plants. For example, the effect of an herbicide such those as described above, on the growth inhibition of plants such as wild-type *Arabidopsis*, soybean, or maize may be determined by plating seeds sterilized by art-recognized methods on plates on a simple minimal salts medium containing increasing concentrations of the inhibitor. Such concentrations are in the range of 0.001, 0.003, 0.01, 0.03, 0.1, 0.3, 1, 3, 10, 30, 110, 300, 1000 and 3000 parts per million (ppm). The lowest dose at which significant growth inhibition can be reproducibly detected is used for subsequent experiments with transgenic plants, cells, etc. Alternatively, heme auxotrophic *E. coli* expressing the PPO can be used in testing.

Two approaches can be taken to confirm that the genetic basis of the resistance of a transgenic plant is a PPO of the present invention. First, alleles of the PPO gene from plants exhibiting resistance to the inhibitor can be isolated using PCR with primers based either upon the mutant region(s) in the resistant cDNA sequence shown in SEQ ID NO:13, or a functionally equivalent sequence. The herbicide resistant enzyme of the present invention can be expressed in a plant of interest after incorporation into a pCambia vector under the transcriptional control of the CaMV 35S promoter, the *Arabidopsis* actin-2 promoter or the native waterhemp PPO promoter, among others well known in the art). Many gene expression systems for plants are well known and readily accessible to the art.

Figure 2:
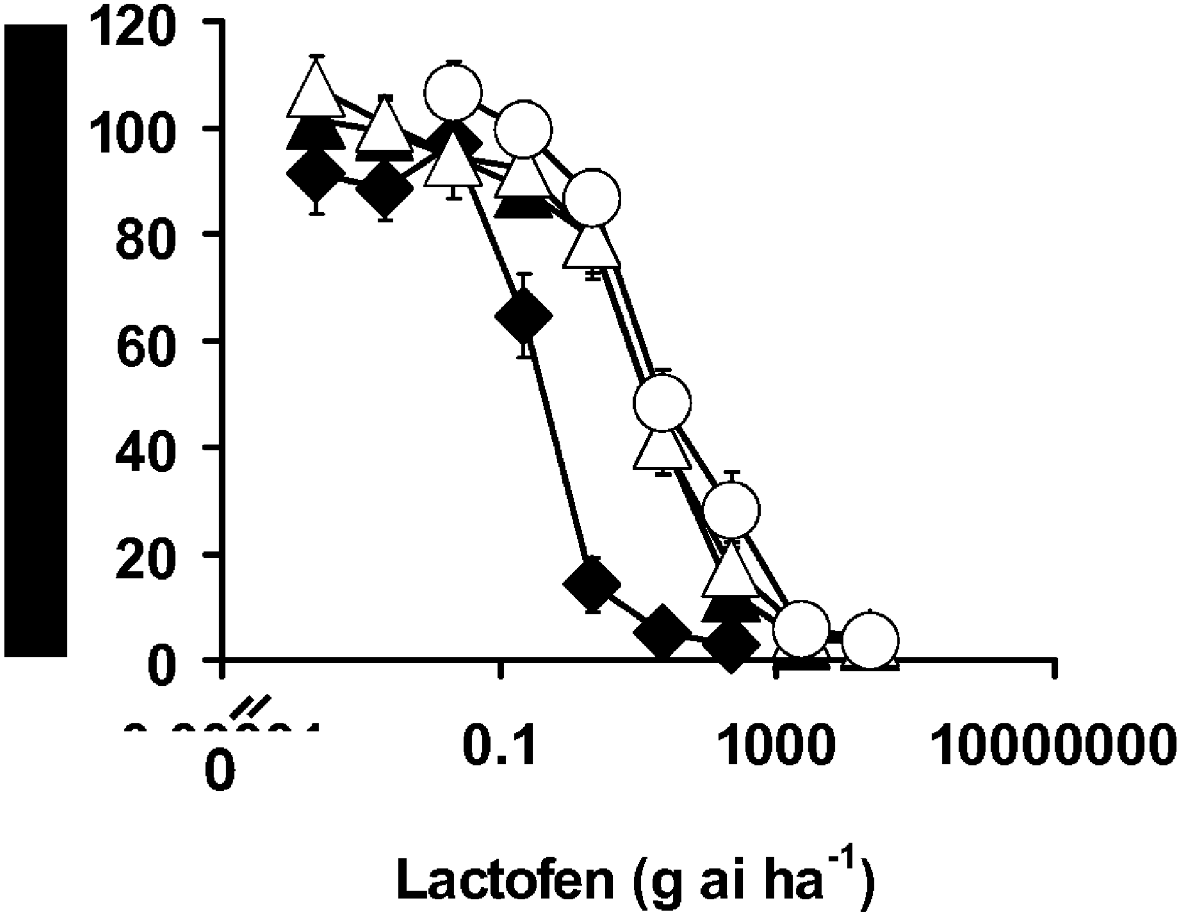
FIG. 2 provides the Lactofen dose-response curves of the protoporphyrinogen oxidase inhibitor-susceptible parent (S=♦), -resistant parent (R=○), hybrid where the maternal parent was R {$F_1$(R)=Δ}, or hybrid where the maternal parent was S {$F_1$(S)=▲}. Waterhemp plants were harvest 15 days after treatment. Vertical bars represent +/−the standard error of the mean (n=12).

To characterize the resistance mechanism in wild waterhemp, plants from a PPO inhibitor-resistant (R) *A. tuberculatus* biotype were reciprocally crossed with wild type (herbicide-susceptible, S) plants to create $F_1$ lines, followed by subsequent crossing to generate $F_2$ and backcross (BC) lines. In response to the PPO inhibitor, lactofen, the resultant *A. tuberculatus* lines segregated for resistance in ratios similar to those expected for a single genetic unit of inheritance (Table 1). Furthermore, plants from lines that were homozygous or heterozygous for resistance survived 53-fold or 31-fold higher doses of lactofen, respectively, when compared with S plants (FIG. 2; Table 2). Thus, resistance to lactofen was inherited as a single, incompletely dominant gene.

$F_2$ lines derived from the same male (half-sib lines) were not significantly different; therefore, the data from lines were combined. Results of $F_2$ progenies treated with lactofen segregated as expected if resistance were inherited as a single gene, with a segregation of 3:1 (R:S) (Table 1). Similarly, $BC_S$ or $BC_R$ lines responded as expected, with a 1:1 or 1:0 segregation for R:S lactofen responses, respectively (Table 1). Because there was no difference in lactofen resistance when it was inherited from the maternal or paternal parent, resistance to lactofen is assumed to be nuclear encoded. The results of these experiments suggest that PPO inhibitor resistance in the R waterhemp biotype is inherited as a single, nuclear encoded gene.

Figure 3A:
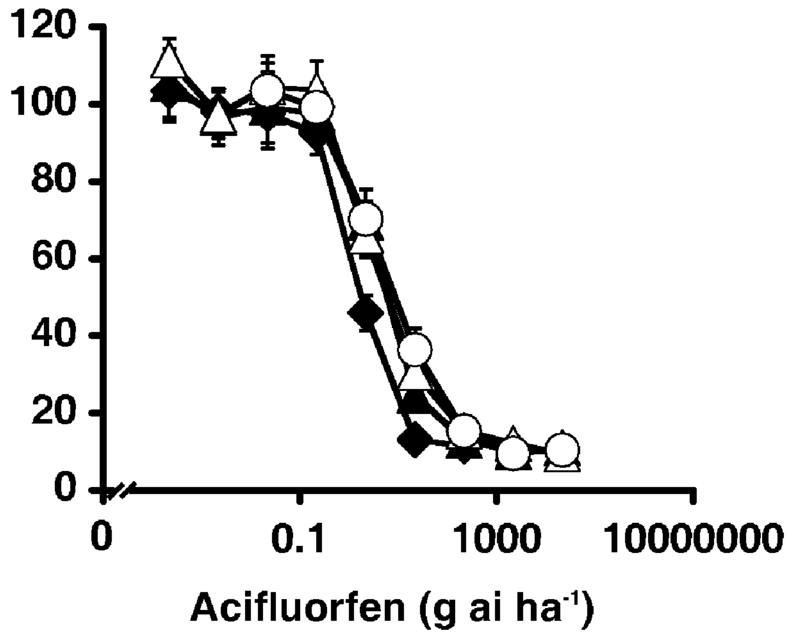
FIGS. 3A-3B show protoporphyrinogen oxidase inhibitor dose-response curves of the susceptible parent (S=♦), resistant parent (R=○), hybrid where the maternal parent was R {$F_1$(R)=Δ}, or hybrid where the maternal parent was S {$F_1$(S)=▲} with two PPO-inhibiting herbicides. Waterhemp plants were harvested 10 days after treatment. Vertical bars represent +/−the standard error of the mean (n=12).
Figure 3B:
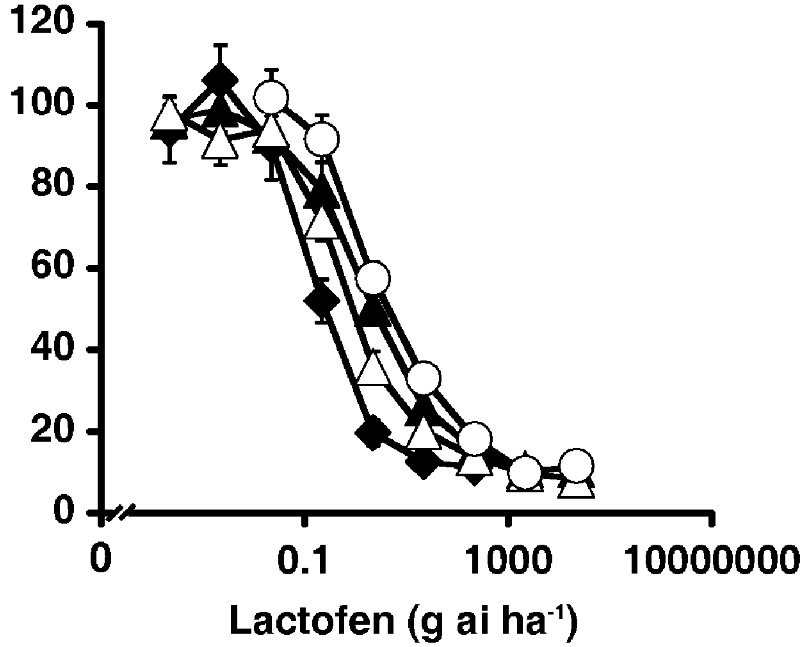

Herbicide dose-response experiments were conducted on the S parent, R parent, or $F_1$ lines to determine the dominance of PPO inhibitor resistance using the methods of Stone (1968) based on the calculation of $GR_{50}$ values. When waterhemp plants were harvested 15 days after lactofen treatment, dominance values of 0.72 or 0.76 were estimated using $F_1$(R) or $F_1$(S) lines, respectively (where 0 to 1=dominant, 0=partially dominant, or 0 to −1=recessive) (Table 2, FIG. 2). However, a potential problem with these results was that waterhemp plants might have been past their linear phase of growth, thus leading to an overestimate of dominance. Therefore, waterhemp plants used in subsequent dose-response experiments were harvested 10 DAT, and were challenged with lactofen or acifluorfen. Dominance values of −0.06 or 0.56 were estimated using $F_1$(R) or $F_1$(S) lines, respectively, in response to lactofen 10 DAT (Table 2, FIG. 3). In response to acifluorfen calculated 10 DAT, dominance values of 0.34 or 0.46 were estimated using $F_1$(R) or $F_1$(S) lines, respectively (Table 2, FIGS. 3A-3B). Results from all dominance experiments suggest that PPO inhibitor resistance in the R biotype is incompletely dominant because nearly all estimated dominance values ranged between 0 and 1.

Figure 9:
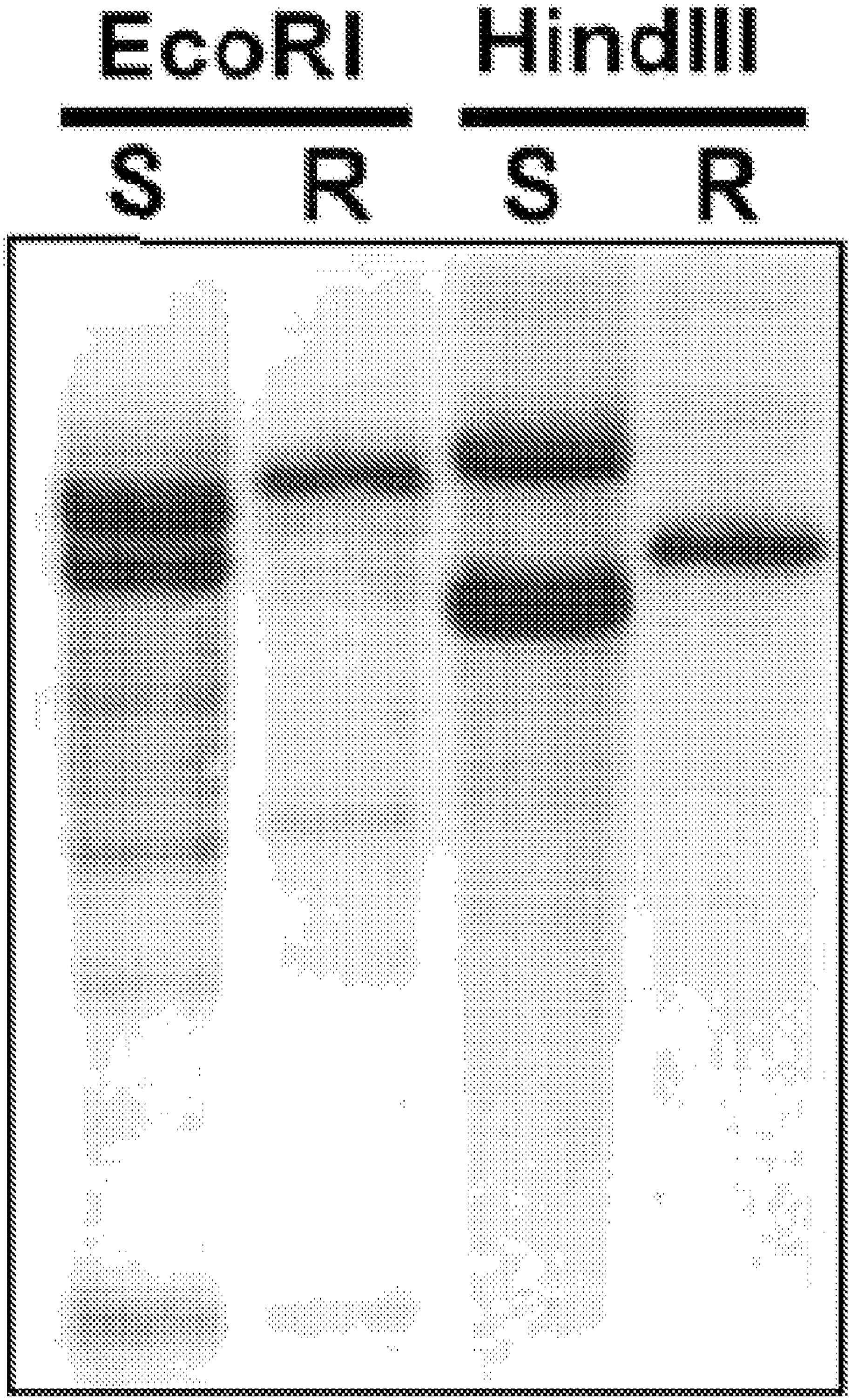
FIG. 9 shows the results of Southern blot analysis of *A. tuberculatus* genomic DNA probed with a fragment of PPX2L. DNA was isolated from plants that were derived from the R or S biotype and digested with EcoRI or HindIII.

To carry out molecular characterization of PPXgenes from waterhemp, complementary DNA (cDNA) sequences that encode PPO isozymes were obtained from R and S *A. tuberculatus* plants, but with unexpected results. From S plants, cDNA sequences for PPX1, PPX2, and a longer version of PPX2, PPX2L, were identified and amino acid sequences encoded were deduced; See SEQ ID NOs: 17-18, 19-20 and 21-22; GenBank accessions DQ386112, DQ386113, and DQ386114. It is noted that PPO1, PPO2 and PPO2L refer to the proteins encoded by the genes PPX1, PPX2 and PPX2L, respectively. In this application where PPO is recited, it is synonymous with PPX2L unless otherwise obvious from context. Comparison of translated sequences of PPX2 and PPX2L indicated that they shared 98% amino acid identity, with the exception of a 30 amino acid extension in the 5' end that was unique to PPX2L. This extension is predicted to encode a signaling sequence for plastid import (Emmanuelson, 2000). Thus, the PPX2L gene isolated from *A. tuberculatus* likely encodes both plastid- and mitochondria-targeted PPO isoforms due to the presence of alternate in-frame initiation codons, a phenomenon that was reported previously for *Spinacia oleracea* (spinach) PPX2 (Watanabe, 2001). In comparison, PPX1 shared 26% and 25% amino acid identity with PPX2 and PPX2L, respectively, and thus is an evolutionarily distinct isozyme. From R plants, only PPX1 and PPX2L genes (See SEQ ID NOs:23-24 and 25-26; GenBank accessions DQ386115 and DQ386116, respectively) were identified based on cDNA sequencing. To confirm the lack of PPX2 identification in R plants, Southern blot analysis was performed using genomic DNA probed with a fragment of PPX2L. Probing with the fragment of PPX2L identified two major bands (presumably PPX2 and PPX2L loci) from S plants, but only a single major band (presumably the PPX2L locus) from R plants, thus confirming the results obtained from sequencing efforts (FIG. 9). Without wishing to be bound by theory, it is believed that the PPX1 from the lactofen resistant waterhemp does not contribute to the resistant phenotype.

Figure 4:
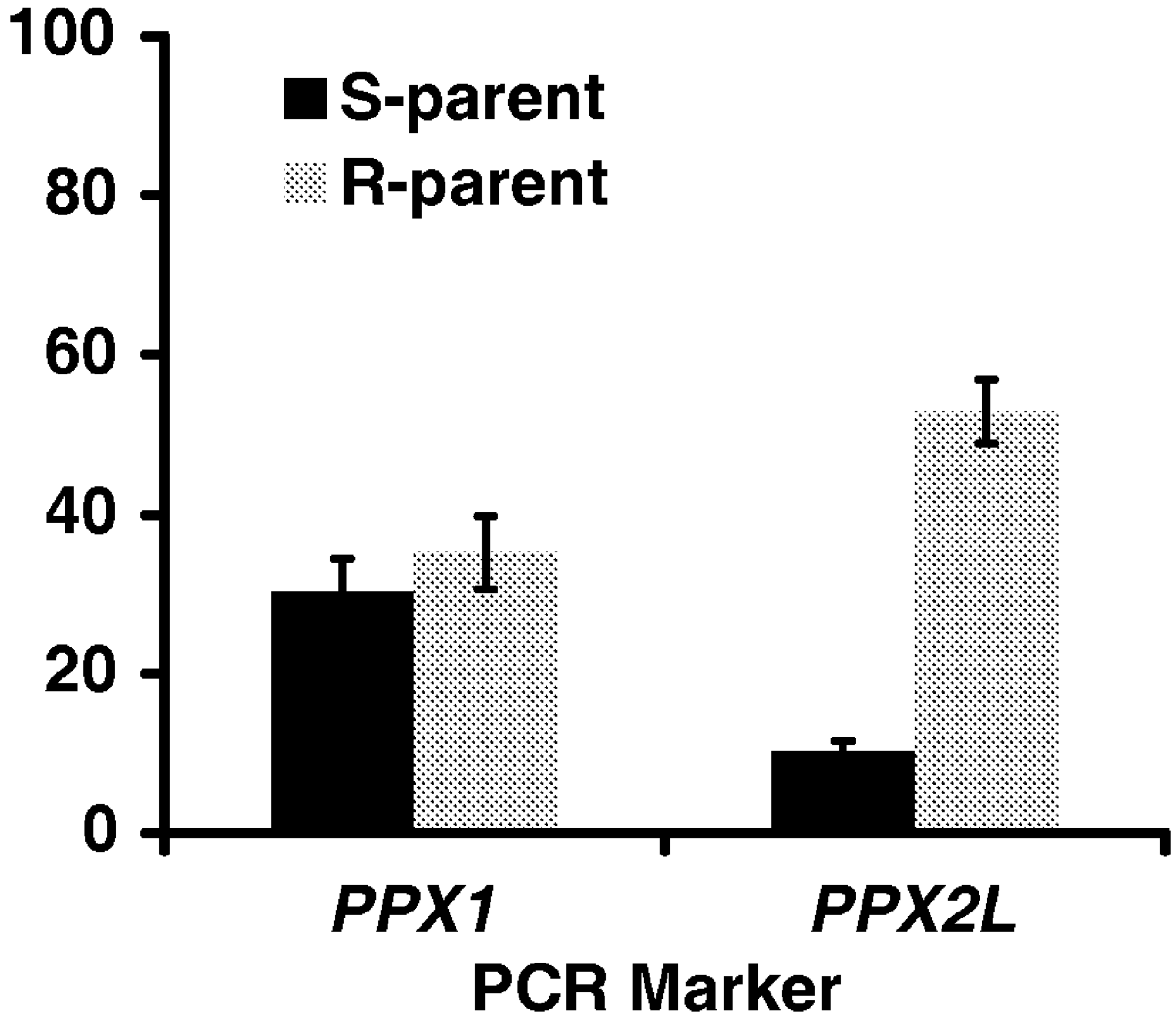
FIG. 4 shows the results of PCR-based molecular marker analysis of PPX1 or PPX2L alleles. *A. tuberculatus* plants used in the study were derived from $F_1$ hybrids backcrossed to the S parent ($BC_S$). Markers were used to determine if the $F_1$-derived pollen carried the S or R parental allele. $BC_S$ plants were treated with lactofen at 110 g ai $ha^{-1}$ plus 1% (by vol) COC and harvested 15 days after treatment. Vertical bars represent +/−the standard error of the mean (PPX1, n=42 or 40 for S or R parental alleles, respectively; PPX2L, n=39 or 49 for S or R parental alleles, respectively)

To determine whether PPX1 or PPX2L mediated PPO inhibitor resistance, polymerase chain reaction (PCR)-based molecular markers were used to follow the inheritance of alleles of these two genes in *A. tuberculatus* lines segregating 1:1 for R or S responses to lactofen. The molecular marker for PPX2L was significantly correlated with lactofen responses ($P<0.0001$), while the marker for PPX1 was not ($P=0.4278$) (FIG. 4). In other words, plants were resistant to lactofen only if they inherited the PPX2L allele from the R parent. Results of molecular markers studies focused further efforts toward differences among PPX2L alleles.

Figure 8:
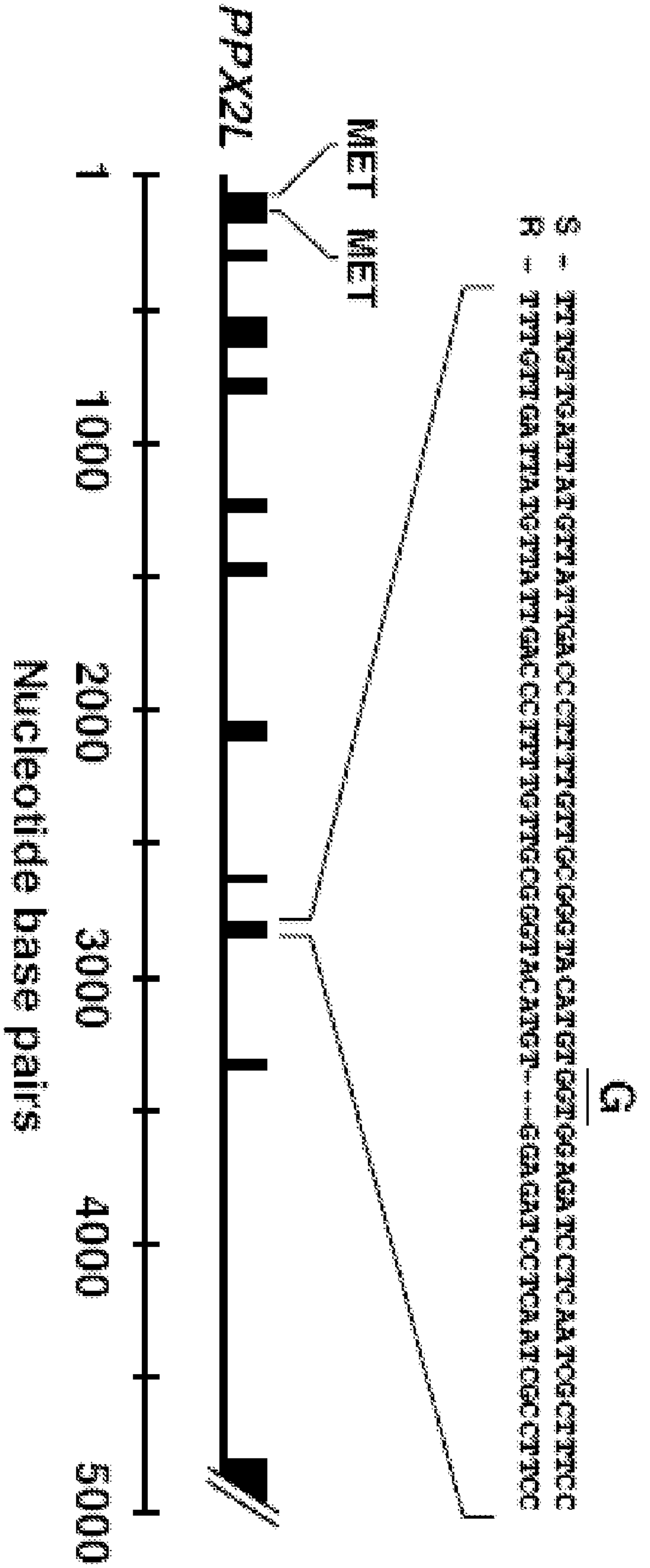
FIG. 8 shows partial coding regions of the 5' end of PPX2L from *A. tuberculatus*. The three-bp deletion leading to a G210 deletion in PPX2L from R plants was identified within the ninth exon starting from the 5' end (see also SEQ ID NO:43 and 44 for the sequences from the sensitive and resistant genes, respectively).

Inspection of the inferred amino acid sequences of PPX2L among S and R plants revealed two amino acid polymorphisms that were correlated with resistance. In an attempt to identify only a single amino acid polymorphism, additional R and S plants were sequenced from independently identified *A. tuberculatus* biotypes (See SEQ ID NOs:27-28 and 29-30; GenBank accessions DQ386117 and DQ386118). Sequencing results and subsequent comparisons identified three additional amino acid polymorphisms (five total); however, only one, a glycine deletion at position 210 (ΔG210), was consistently polymorphic between all R and S plants analyzed (FIG. 7). PPX2L also was sequenced using genomic DNA (gDNA)

as a template (See SEQ ID NOs:31-32 and 33-34; GenBank accessions DQ394875 and DQ394876 for S and R plants, respectively) to further confirm the existence of the three-bp deletion corresponding to the G210 codon. Alignment of gDNA and cDNA sequences of PPX2L identified the codon corresponding to the G210 residue in the ninth exon when starting from the 5' end (FIG. 8). The three-bp deletion was also identified in PPX2L gDNA sequences of R plants, therefore indicating that the ΔG210 mutation in PPO2L was not the result of an error introduced during mRNA processing.

Figure 5:
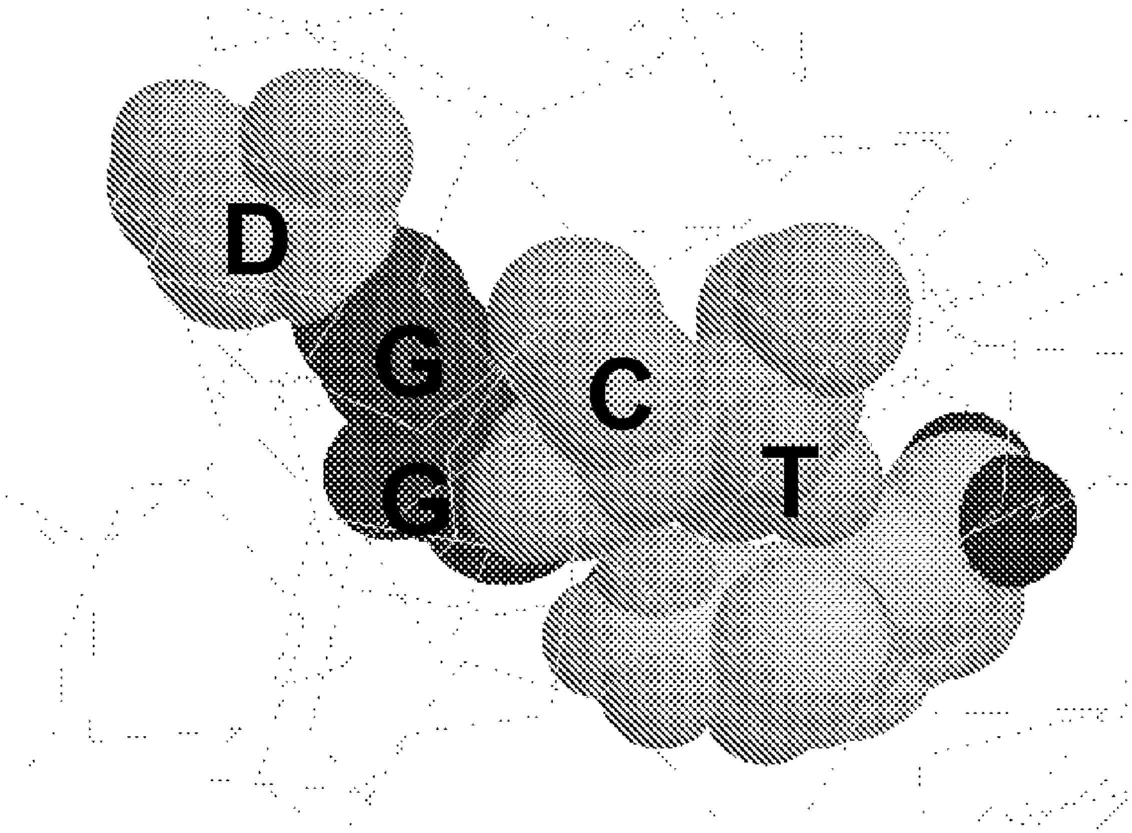
FIG. 5 shows selected amino acid residues of *N. tabacum* PPO2 in proximity to the herbicide-binding site. *A. tuberculatus* plants resistant to PPO inhibitors are missing a glycine residue equivalent to G178 of *N. tabacum*. This amino acid deletion is predicted to hinder PPO inhibitor binding. Letter abbreviations are: amino acid residues, D=aspartic acid, G=glycine, C=cysteine, T=threonine; PPO-inhibiting herbicide, Flz=fluazolate.

The ΔG210 mutation was also assessed using the resolved protein structure of PPO2 from *Nicotiana tabacum* (tobacco) as a reference (Koch, 2004; Martz, 2002). The equivalent amino acid to G210 of *A. tuberculatus* PPO2L (G178 of *N. tabacum*PPO) was located near the herbicide-binding site, thus supporting the prediction that the G210 deletion was responsible for herbicide resistance (FIG. 5). It is understood that a G211 deletion is equivalent in function to the G210 deletion mutant enzymes described herein, and either a G210 or a G211 deletion can be combined with any of the polymorphisms set forth in FIGS. 10A-10B.

Figure 6:
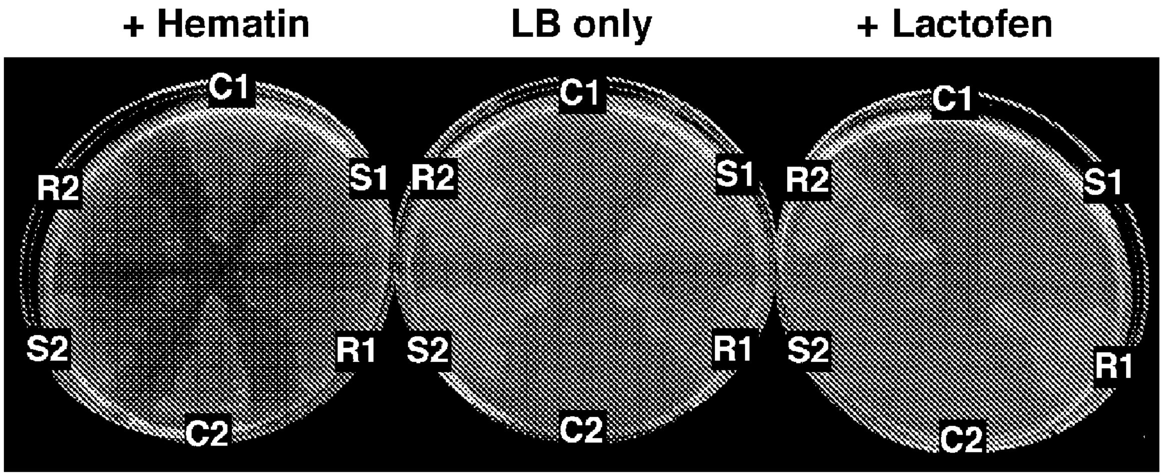
FIG. 6 illustrates PPO expression in a hemG mutant strain of *E. coli. E. coli* cells were grown on LB medium alone or supplemented with hematin (20 μg $ml^{-1}$) or lactofen (100 nM). *E. coli* isolates were: C1 and C2, non-transformed controls; S1 and S2, transformed with vector encoding *A. tuberculatus*-derived PPO2L with glycine at position 210; R1 and R2, transformed with vector encoding identical PPO2L with the exception of a deletion of glycine at position 210.

Complementation assays utilized a hemG (PPO) mutant strain of *E. coli*, SASX38 (Sasarman, 1979), to access the effect of the G210 deletion toward herbicide responses. The SASX38 strain grows very slowly unless supplied with exogenous heme or rescued with an alternative source of PPO. Furthermore, since wild type *E. coli* is naturally tolerant to PPO inhibitors, use of the SASX38 strain enabled a relatively direct assay for herbicide sensitivity of the S and R PPO2Ls from *A. tuberculatus* (Li, 2003; Sasarman, 1993). The SASX38 *E. coli* strain was transformed with plasmid constructs encoding PPO2L proteins differing only in the presence/absence of G210. Both constructs were able to rescue growth of the SASX38 *E. coli* strain, thus indicating both PPX2L genes encoded functional proteins (FIG. 6). However, supplementation of the growth medium with lactofen dramatically inhibited growth of *E. coli* transformed with the wild type PPX2L, but not *E. coli* transformed with the ΔG210 PPX2L (FIG. 6). Thus, the three-bp deletion in PPX2L resulting in deletion of a glycine at position 210 of PPO2L was sufficient to confer resistance to lactofen.

TABLE 1

Inheritance of resistance to the PPO inhibitor, lactofen, in *A. tuberculatus*. $F_1$ plants were obtained from reciprocal crosses between a resistant (R) and sensitive (S) biotype ($F_1$(R): female parent was R; $F_1$(S): female parent was S). Plants from $F_2$ and backcross lines were treated with lactofen at 110 g ai $ha^{-1}$ plus 1% (by vol) COC, and scored as R or S 15 days after treatment. The expected segregation ratio of R to S responses assumes a single genetic unit of inheritance.

| Male parent | Female parent | N | Observed numbers R | Observed numbers S | Expected ratio (R:S) | $\chi^2$ | P-value |
|---|---|---|---|---|---|---|---|
| $F_1$ (R) | $F_1$ (R) | 400 | 297 | 103 | 3:1 | 0.120 | 0.7290 |
| | S | 200 | 98 | 102 | 1:1 | 0.080 | 0.7772 |
| | R | 200 | 200 | 0 | 1:0 | 0 | 1 |
| $F_1$ (S) | $F_1$ (S) | 400 | 304 | 96 | 3:1 | 0.213 | 0.6441 |
| | S | 200 | 109 | 91 | 1:1 | 1.620 | 0.2030 |
| | R | 200 | 200 | 0 | 1:0 | 0 | 1 |

TABLE 2

$GR_{50}$ (growth reduction by 50%) and degree of dominance[b] estimates for PPO inhibitor-resistance in *A. tuberculatus*. Plants from R, S, $F_1$(R), or $F_1$(S) lines were treated with lactofen or acifluorfen, and data collected either 10 or 15 days after treatment (DAT). Dominance estimates are interpreted as: 0 to 1 = dominant; 0 = partially dominant; 0 to −1 = recessive.

| DAT | Herbicide | $GR_{50}$ R | $GR_{50}$ $F_1$(R) (g ai $ha^{-1}$) | $GR_{50}$ $F_1$(S) | $GR_{50}$ S | Dominance $F_1$(R) | Dominance $F_1$(S) |
|---|---|---|---|---|---|---|---|
| 15 | Lactofen | 21 | 12 | 13 | 0.4 | 0.72 | 0.76 |
| 10 | Acifluorfen | 5.8 | 3.8 | 4.1 | 1.6 | 0.34 | 0.46 |
| | Lactofen | 2.9 | 0.7 | 1.6 | 0.2 | −0.06 | 0.56 |

[a] $GR_{50}$ estimates were calculated using PROC NLIN in SAS as described by Seefeldt et al. (1995).
[b]The degree of dominance (D) = $(2W_3 - W_2 - W_1)/(W_2 - W_1)$, where $W_1$ = log($GR_{50}$) of the S-parent, W2 = log($GR_{50}$) or the R-parent, and $W_3$ = log ($GR_{50}$) of the $F_1$ lines (0 to 1 = dominant; 0 = partially dominant; 0 to −1 = recessive) (Stone 1968).

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selectable markers used routinely in transformation include the nptII gene which confers resistance to kanamycin and related antibiotics (Messing and Vierra. 1982. Gene 19: 259-268; Bevan et al. 1983. Nature 304:184-187), the bar gene which confers resistance to the herbicide phosphinothricin (White et al. 1990. Nucl Acids Res 18: 1062; Spencer et al. 1990. Theor Appl Genet 79: 625-631), the hph gene which confers resistance to the antibiotic hygromycin (Blochinger and Diggelmann. 1984. Mol Cell Biol 4: 2929-2931), and the dhfr gene, which confers resistance to methotrexate (Bourouis et al. 1983. EMBO J. 2(7): 1099-1104).

Many vectors are available for transformation using *A. tumefaciens*. These typically carry at least one T-DNA border sequence and include vectors such as pBIN19 (Bevan. 1984. Nucl. Acids Res.). Below the construction of two typical vectors is described. pCAMBIA vectors are well known to the art as well.

The exemplary binary vector pCIB10 contains a gene encoding kanamycin resistance for selection in plants, T-DNA right and left border sequences and incorporates sequences from the wide host-range plasmid pRK252 allowing it to replicate in both *E. coli* and *Agrobacterium*. Its construction is described by Rothstein et al. 1987. Gene 53: 153-161. Various derivatives of pCIB10 have been constructed which incorporate the gene for hygromycin B phosphotransferase described by Gritz et al. 1983. Gene 25: 179-188). These derivatives enable selection of transgenic plant cells on hygromycin only (pCIB743), or hygromycin and kanamycin (pCIB715, pCIB717). See, e.g., Rogers et al., Methods for Plant Molecular Biology, Weissbach and Weissbach, eds, Academic Press, San Diego, Calif., 1988, for a description of a kanamycin resistance marker. Other selective agents for use in plants include bleomycin, gentamicin and certain herbicide resistance markers (not via the PPX2L of the present invention).

Transformation without the use of *A. tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g. PEG and electroporation) and microinjection. The choice of vector depends largely on the preferred selection for the species being transformed.

Gene sequences intended for expression in transgenic plants are first assembled in expression cassettes behind a suitable promoter and upstream of a suitable transcription terminator. These expression cassettes can then be easily transferred to the plant transformation vectors of choice.

The selection of a promoter used in expression cassettes determines the spatial and temporal expression pattern of the transgene in the transgenic plant. Selected promoters express transgenes in specific cell types (such as leaf epidermal cells, mesophyll cells, root cortex cells) or in specific tissues or organs (roots, leaves or flowers, for example), and this selection reflects the desired location of expression of the transgene. Alternatively, the selected promoter may drive expression of the gene under a light-induced or other temporally regulated promoter.

A variety of transcriptional terminators are available for use in expression cassettes. These are responsible for the termination of transcription beyond the transgene and its correct polyadenylation. Appropriate transcriptional terminators and those which are known to function in plants and include the CaMV 35S terminator, the tml terminator, the nopaline synthase (nos) terminator, the pea rbcS E9 terminator. These can be used in both monocotyledonous and dicotyledonous plants.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene significantly enhance the expression of the wild-type gene under its cognate promoter when introduced into maize cells. Intron 1 enhances expression in fusion constructs with the chloramphenicol acetyltransferase gene (Callis et al. 1987. Genes Develop. 1: 1183-1200). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses also enhance expression, especially in dicotyledonous cells. Leader sequences from Tobacco Mosaic Virus (TMV, the "W-sequence"), Maize Chlorotic Mottle Virus (MCMV), and Alfalfa Mosaic Virus (AMV) have been shown to enhance expression (e.g. Gallie et al. 1987. Nucl. Acids Res. 15: 8693-8711; Skuzeski et al. 1990. Plant Molec. Biol. 15:65-79).

While the herbicide resistant PPO of the present invention contains targeting sequences for chloroplast and mitochondria, various mechanisms for targeting gene products are known in plants; the sequences controlling the functioning of these mechanisms have been studied. Targeting of gene products to the chloroplast is controlled by a signal sequence at the N-terminus a protein; it is cleaved during chloroplast import to yield the mature protein (e.g. Comai et al. 1988. J. Biol. Chem. 263: 15104-15109). These signal sequences can be fused to heterologous gene products (lacking such sequences) to effect the import of heterologous products into the chloroplast (van den Broeck et al. 1985. Nature 313: 358-363). DNA encoding for appropriate signal sequences can be isolated from the 5' end of the cDNAs encoding the RUBISCO protein, the CAB protein, the EPSP synthase enzyme, the GS2 protein and many other chloroplast-localized proteins.

Other gene products are localized to other organelles such as the mitochondrion and the peroxisome (e.g. Unger et al. 1989. Plant Molec. Biol. 13: 411-418). Sequences encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al. 1985. Proc. Natl. Acad. Sci. USA 82: 6512-6516).

In addition, sequences are known which target gene products to other cell compartments. N-terminal sequences are responsible for targeting to the ER, the apoplast, and extracellular secretion from aleurone cells (Koehler and Ho. 1990. Plant Cell 2: 769-783). Additionally, N-terminal sequences, in conjunction with C-terminal sequences, are responsible for vacuolar targeting (Shinshi et al. 1990. Plant Molec. Biol. 14: 357-368).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier, pp 1081-1091,1982; Wasmann et al. 1986. Mol. Gen. Genet. 205: 446-453). These construction techniques are well known in the art and are equally applicable to mitochondria and peroxisomes. The choice of targeting which may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized not only in conjunction with their cognate promoters, but also in conjunction with heterologous promoters so as to effect a specific targeting goal (where the heterologous promoter has an expression pattern different to that of the promoter from which the targeting signal is derived).

*Agrobacterium*-mediated transformation is a preferred technique for transformation of dicots because of the high efficiency of transformation and success with many different species. The many crop species which are routinely transformable by *Agrobacterium* include tobacco, tomato, sunflower, cotton, oilseed rape, potato, soybean, alfalfa and poplar (EP 317 511, cotton; EP 0 249 432, tomato, to Calgene; WO 87/07299, *Brassica*, to Calgene; U.S. Pat. No. 4,795,855, poplar). *Agrobacterium* transformation typically involves the transfer of the binary vector carrying the foreign DNA of interest to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. 1993. Plant Cell 5: 159-169). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen and Willmitzer. 1988. Nucl. Acids Res. 16: 9877).

Once an expression construct or expression vector of the invention has been established, it can be transformed into a plant cell. A variety of methods for introducing nucleic acid sequences (e.g., vectors) into the genome of plants and for the regeneration of plants from plant tissues or plant cells are known (Plant Molecular Biology and Biotechnology (CRC Press, Boca Raton, Fla., pp. 71-119 (1993); White FF. 1993. Vectors for Gene Transfer in Higher Plants; in: Transgenic Plants, vol. 1, Engineering and Utilization, Ed.: Kung and Wu R, Academic Press, 15-38; Jenes et al. 1993. Techniques for Gene Transfer, in: Transgenic Plants, vol. 1, Engineering and Utilization, Ed.: Kung and R. Wu, Academic Press, pp. 128-143; Potrykus et al. 1991. Annu. Rev. Plant Physiol. Plant Molec. Biol. 42:205-225; Halford and Shewry. 2000. Br. Med. Bull. 56:62-73).

Transformation methods may include direct and indirect methods of transformation. Suitable direct methods include polyethylene glycol induced DNA uptake, liposome-mediated transformation (U.S. Pat. No. 4,536,475), biolistic methods using the gene gun (particle bombardment; Fromm et al. 1990. Bio/Technology. 8:833-9; Gordon-Kamm et al. 1990. Plant Cell 2:603), electroporation, incubation of dry embryos in DNA-comprising solution, and microinjection. In the case of these direct transformation methods, the plasmid used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 116,718), viral infection by means of viral vectors (EP 067,553; U.S. Pat. No. 4,407,956; WO 95/34668; WO 93/03161) or by means of pollen (EP 270,356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. 1985. Science 225:1229f. The *Agrobacterium*-mediated transformation is best suited to dicotyledonous plants but has also been adapted to monocotyledonous plants. The transformation of plants by *Agrobacteria* is described, for example, in White F F, Vectors for Gene Transfer in Higher Plants; in Transgenic Plants, Vol. 1, Engineering and Utilization, edited by S. D. Kung and R. Wu, Academic Press, 1993, pp. 15-38; Jenes B et al. 1993. Techniques for Gene Transfer, in: Transgenic Plants, Vol. 1, Engineering and Utilization, edited by S. D. Kung and R. Wu, Academic Press, pp. 128-143; Potrykus 1991. Annu Rev Plant Physiol Plant Molec Biol 42:205-225).

Transformation may result in transient or stable transformation and expression; stable transformation is preferred in the practice of the present invention. Although a nucleotide sequence of the present invention can be inserted into any plant and plant cell, it is particularly useful in crop plant cells.

Various tissues are suitable as starting material (explant) for the *Agrobacterium*-mediated transformation process including but not limited to callus (U.S. Pat. No. 5,591,616; EP 604 662), immature embryos (EP 672 752), pollen (U.S. Pat. No. 5,929,300), shoot apex (U.S. Pat. No. 5,164,310), or in planta transformation (U.S. Pat. No. 5,994,624). The method and material described herein can be combined with virtually all *Agrobacterium* mediated transformation methods known in the art. Preferred combinations include, but are not limited, to the following starting materials and methods:

| Variety | Material/Citation |
|---|---|
| Monocotyledonous plants: | Immature embryos (EP-A1 672 752)<br>Callus (EP-A1 604 662)<br>Embryogenic callus (U.S. Pat. No. 6,074,877)<br>Inflorescence (U.S. Pat. No. 6,037,522)<br>Flower (in planta) (WO 01/12828) |
| Banana | U.S. Pat. No. 5,792,935; EP 731 632; U.S. Pat. No. 6,133,035 |
| Barley | WO 99/04618 |
| Maize | U.S. Pat. No. 5,177,010; U.S. Pat. No. 5,987,840 |
| Pineapple | U.S. Pat. No. 5,952,543; WO 01/33943 |
| Rice | EP 897 013; U.S. Pat. No. 6,215,051; WO 01/12828 |
| Wheat | AU 738 153; EP 856 060 |
| Beans | U.S. Pat. No. 5,169,770; EP 397 687 |
| *Brassica* | U.S. Pat. No. 5,188,958; EP 270 615; EP-A1 1,009,845 |
| *Cacao* | U.S. Pat. No. 6,150,587 |
| *Citrus* | U.S. Pat. No. 6,103,955 |
| Coffee | AU 729 635 |
| Cotton | U.S. Pat. No. 5,004,863; EP-A1 270 355; U.S. Pat. No. 5,846,797; EP-A1 1,183,377; EP-A1 1,050,334; EP-A1 1,197,579; EP-A1 1,159,436 Pollen transformation (U.S. Pat. No. 5,929,300 In planta transformation (U.S. Pat. No. 5,994,624) |
| Pea | U.S. Pat. No. 5,286,635 |
| Pepper | U.S. Pat. No. 5,262,316 |
| Poplar | U.S. Pat. No. 4,795,855 |
| Soybean | cotyledonary node of germinated soybean seedlings shoot apex (U.S. Pat. No. 5,164,310) axillary meristematic tissue of primary, or higher leaf node of about 7 days germinated soybean seedlings organogenic callus cultures dehydrated embryo axes U.S. Pat. No. 5,376,543; EP 397 687; U.S. Pat. No. 5,416,011 U.S. Pat. No. 5,968,830; U.S. Pat. No. 5,563,055; U.S. Pat. No. 5,959,179; EP 652 965; EP 1,141,346 |
| Sugarbeet | EP 517 833; WO 01/42480 |
| Tomato | U.S. Pat. No. 5,565,347 |

In another embodiment, a nucleotide sequence of the present invention is directly transformed into the plastid genome. Plastid expression, in which genes are inserted by homologous recombination into the several thousand copies of the circular plastid genome present in each plant cell, takes advantage of the enormous copy number advantage over nuclear-expressed genes to permit high expression levels. In a preferred embodiment, the nucleotide sequence is inserted into a plastid targeting vector and transformed into the plastid genome of a desired plant host. Plants homoplasmic for plastid genomes containing the nucleotide sequence are obtained, and are preferentially capable of high expression of the nucleotide sequence.

Plastid transformation technology is, for example, extensively described in U.S. Pat. Nos. 5,451,513; 5,545,817; 5,545,818; and 5,877,462; in WO 95/16783 and WO 97/32977; and in McBride et al. 1994. Proc. Natl. Acad. Sci. USA 91: 7301-7305, all incorporated herein by reference in their entireties. The basic technique for plastid transformation involves introducing regions of cloned plastid DNA flanking a selectable marker together with the nucleotide sequence into a suitable target tissue, e.g., using biolistic or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. 1990 Proc. Natl. Acad. Sci. USA 87: 8526-8530; Staub et al. (1992) Plant Cell 4, 39-45). The presence of cloning sites between these markers allowed creation of a plastid targeting vector for introduction of foreign genes (Staub et al. 1993. EMBO J. 12: 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab et al. 1993. Proc. Natl. Acad. Sc. USA 90: 913-917). Other selectable markers useful for plastid transformation are known in the art and encompassed within the scope of the invention. However, in the context of the present invention, the use of nuclear herbicide resistance gene is preferred, especially when expression is achieved in plastids as well as cytoplasm, and if a marker is used which confers herbicide resistance, there should be no cross resistance between that marker and the herbicide resistant PPO of the present invention.

For using the methods according to the invention, the skilled worker has available well-known tools, such as expression vectors with promoters which are suitable for plants, and methods for the transformation and regeneration of plants.

To select cells which have successfully undergone transformation, it is preferred to introduce a selectable marker which confers, to the cells which have successfully undergone transformation, a resistance to a biocide (for example a herbicide), a metabolism inhibitor such as 2-deoxyglucose-6-phosphate (WO 98/45456) or an antibiotic. The selection marker permits the transformed cells to be selected from untransformed cells (McCormick et al. 1986. Plant Cell Reports 5:81-84). Suitable selection markers are described above and includes antibiotic resistance markers, among others.

Transgenic plants can be regenerated in the known manner from the transformed cells. The resulting plantlets can be planted and grown in the customary manner. Preferably, two or more generations should be cultured to ensure that the genomic integration is stable and hereditary. Suitable methods are described (Fennell et al. 1992. Plant Cell Rep. 11: 567-570; Stoeger et al. 1995. Plant Cell Rep. 14:273-278; Jahne et al. 1994. Theor Appl Genet 89:525-533).

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (ie. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. 1986. Biotechnology 4: 1093-1096). EP 0 292 435, EP 0 392 225 and WO 93107278 describe techniques for the preparation of callus and protoplasts from an elite inbred line of maize, transformation of protoplasts using PEG or electroporation, and the regeneration of maize plants from transformed protoplasts. Gordon-Kamm et al. 1990. Plant Cell 2: 603-618 and Fromm et al. 1990. Biotechnology 8: 833-839 have published techniques for transformation of A188-derived maize line using particle bombardment. Furthermore, WO 93/07278 and Koziel et al. 1993. Biotechnology 11: 194-200 describe techniques for the transformation of elite inbred lines of maize by particle bombardment. This technique utilizes immature maize embryos of 1.5-2.5 mm length excised from a maize ear 14-15 days after pollination and a biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. 1988. Plant Cell Rep 7: 379-384; Shimamoto et al. 1989. Nature 338: 274-277; Datta et al. 1990. Biotechnology 8: 736-740). Both types are also routinely transformable using particle bombardment (Christou et al. 1991. Biotechnology 9: 957-962).

EP 332 581 describes techniques for the generation, transformation and regeneration of Pooideae protoplasts. These techniques allow the transformation of *Dactylis* and wheat. Furthermore, wheat transformation was been described by Vasil et al. 1992. Biotechnology 10: 667-674) using particle bombardment into cells of type C long-term regenerable callus, and also by Vasil et al. 1993. Biotechnology 11: 1553-1558 and Weeks et al. 1993. Plant Physiol. 102: 1077-1084 using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige and Skoog. 1962. Physiologia Plantarum 15: 473497) and 3 mg/l 2,4-D for induction of somatic embryos which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics, helium device using a burst pressure of about 1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contained half-strength MS, 2% sucrose, and the same concentration of selection agent. U.S. patent application Ser. No. 08/147,161 describes methods for wheat transformation.

Resistant mutant plasmids, selected for resistance against a single herbicide, are tested against a spectrum of other protox-inhibiting compounds. A strain containing the wild-type plasmid is plated on a range of concentrations of each compound to determine the lethal concentration for each one. Resistant mutant plasmids in the same genetic background are plated and scored for the ability to survive on a concentration of each compound which is at least 10 fold higher than the concentration that is lethal to the strain containing the wild-type plasmid.

The herbicide resistant PPO isolated from waterhemp confers the resistant phenotype to transformed *E. coli*, and it likewise confers the resistant phenotype to transgenic plants into which it has been introduced. Table 4 gives the consensus amino acid sequence derived from at least three specific examples of a PPX2L sequence. Unlike various herbicide resistant mutants previously described (see, e.g., U.S. Pat. Nos. 6,282,837; 5,939,602; and 6,808,904), the present resistant mutants have undergone a spontaneous deletion mutation such that where there was Gly-Gly, there is now only one Gly residue (wild type Gly-Gly at amino acids 210-211 of SEQ ID NO:16). The PPO mutant coding sequence in Table 4 only varies from the wild type in the deletion of a Gly codon; the PPO amino acid sequence depicted in Table 4 et seq. further contain an amino acid substitution at residue Gln for Arg at position 182 and Cys for Ser at position 448. See also FIG. 10A-10B for additional poilymorphisms. Without wishing to be bound by any particular theory, the present inventors believe that the Gly deletion alone is sufficient to confer the herbicide resistant phenotype. Thus the wild type sequence can be modified only to effect the Gly-Gly to Gly mutation, or it can include one or the other of the substitutions in addition to the Gly deletion, with the result of conferring resistant to herbicides, as described herein. Expression of any of these Gly-deleted enzymes in a transgenic plant results in a plant with robust resistance to herbicides.

As an alternative to genetic modification of a crop of interest, the herbicide resistant PPO gene of the present invention can be introduced into cultivated amaranth species by conventional plant breeding (crossing the resistant weed with the crop, selecting for herbicide resistant progeny with the desired crop characteristics, and then backcrossing for three to ten cycles progeny plants to the crop species, selecting for herbicide resistance and crop characteristics) to produce the resistant crop. *Amaranthus* species which are cultivated as crops include, but are not limited to, *A. hypochondriacus, A. cruentus, A. caudatus, A. dubius*, and *A. tricolor.*

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, lie, Isoleucine; K, Lys, Lysine; L, Leu, Leucine; M, Met, Methionine; N, Asn, Asparagine; P, Pro, Proline; Q, GIn, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from or produced in a host cell in which it is recombinantly produced. It can be purified or it can simply be free of other proteins and biological materials with which it is associated in nature.

A transgenic plant is one which contains and expresses a gene (or transgene) which it does not contain and express in nature. The transgene can be a gene found in the particular plant but altered in the laboratory to be covalently attached to sequences which it does not occur in nature, the gene can have been altered in the laboratory to have a particular sequence of interest or to have a particular function that it did not previously, or the gene can have been isolated from a mutant plant of the same species and introduced into the genome of a plant of that species, which plant had not had that particular gene or sequence. Progeny transgenic plants are offspring (and succeeding generations of offspring which contain and express a copy of the transgene of interest. Transgenic seed are those produced by a transgenic plant or progeny transgenic plant which contain the transgene of interest.

Expression directed by a particular sequence means there is transcription and translation of an associated downstream sequence. With reference to tissue-specific regulation of expression of a PPO sequence of interest operably linked to the plant-expressible transcription regulatory sequence, expression may be advantageously determined by a strong constitutive promoter such as the Cauliflower Mosaic Virus 19S or 35 S promoter, a tandem repeat 35S promoter, the actin 2 promoter from *Arabidopsis thaliana*, among others.

A transcription regulatory sequence includes a promoter sequence and the cis-active sequences necessary for regulated expression of the operably linked sequence in the desired plant tissues. A promoter includes sequences sufficient to cause transcription of an associated (downstream, operably linked) sequence. The promoter is desirably constitutive, or it may be regulated, e.g., inducible, the transcription regulatory sequences cause expression of the operably linked coding sequence in response to an environmental signal (light, chemical, cold, heat, etc).

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a polynucleotide which is substantially separated from other polynucleotide sequences which naturally accompany a native herbicide resistant PPO coding sequence. This coding sequence may be operably linked to its native transcription regulatory sequences or another native transcription regulatory sequence functional in a plant cell. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in the same reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other PPO coding sequences or other transcriptional regulatory sequences. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially *Escherichia coli*, wherein protein expression is desired or in a PPO-deficient strain of *Escherichia coli* when testing of PPO activity and/or herbicide resistance is desired. Commonly used prokaryotic hosts include strains of *Escherichia coli*, although other prokaryotes, such as *Bacillus subtilis* or a pseudomonad, may also be used. Eukaryotic host cells can include various plant species such as *Arabidopsis thaliana, Nicotiana tabacum, Glycine max, Zea mays, Medicago*, yeast, filamentous fungi, plant, insect, amphibian and avian species.

The polynucleotides of interest may also be produced by chemical synthesis, e.g., by the phosphoramidite method described by Beaucage and Caruthers (1981) Tetra. Letts. 22: 1859-1862 or the triester method according to Matteuci et al. (1981) J. Am. Chem. Soc. 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1999) Short Protocols in Molecular Biology, fourth edition, Wiley and Sons, New York; and Metzger et al. (1988) Nature, 334: 31-36. Many useful vectors for expression in bacteria, yeast, fungal, mammalian, insect, plant or other cells are well known in the art and may be obtained such vendors as Clontech, Invitrogen, Stratagene, New England Biolabs, Promega and others. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, N.Y. (1983). While such expression vectors may replicate autonomously, they may less preferably replicate by being inserted into the genome of the host cell.

Expression and cloning vectors likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning or expression vector. Only those host cells into which the marker gene has been introduced will survive and/or grow under selective conditions. Typical selection genes encode proteins that confer resistance to antibiotics or other toxic substances, e.g., ampicillin, neomycin, methotrexate, etc.; complement auxotrophic deficiencies; or supply critical nutrients not available from complex media. The choice of the proper selectable marker depends on the host cell; appropriate markers for different hosts are known in the art.

Recombinant host cells, in the present context, are those which have been genetically modified to contain and express an isolated DNA molecule of the instant invention. The DNA can be introduced by any means known to the art which is appropriate for the particular type of cell, including without limitation, transformation, lipofection, microinjection, Agroinfection, electroporation or particle bombardment.

It is recognized by those skilled in the art that the DNA sequences may vary due to the degeneracy of the genetic code and codon usage. All DNA sequences which code for the specifically exemplified herbicide resistant PPO having the particular glycine deletion taught herein are included in this invention, including the DNA sequence as given in Table 3, as well as functional equivalents thereto including or lacking substitution mutations as further taught herein.

Additionally, it is recognized by those skilled in the art that allelic variations occur in the DNA sequences which do not significantly change activities of the proteins they encode. All synonymous and functionally equivalent DNA sequences are included within the scope of this invention. The skilled artisan understands that the sequence of the exemplified herbicide resistant PPO sequences can be used to identify and isolate additional, nonexemplified nucleotide sequences which are functionally equivalent to the sequences given in SEQ ID NO:13, 25, 29 and 45, including naturally occurring variations in PPX2L sequences.

Hybridization and/or polymerase chain reaction procedures are useful for identifying polynucleotides with sufficient homology to the subject regulatory sequences to be useful as taught herein. The particular hybridization technique is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary, if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in WO 93/16094.

Various degrees of stringency of hybridization can be employed. The more stringent the conditions, the greater the complementarity required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak (1987) DNA Probes, Stockton Press, New York, N.Y., pp. 169-170.

As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5× Denhardt's solution/0.1% SDS, and washing in 0.2×SSC/0.1% SDS at room temperature. An example of conditions of moderate stringency are hybridizing at 68° C. in 5×SSC/5× Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) Current Protocols in Molecular Biology, John Wiley & Sons, NY, N.Y., for further guidance on hybridization conditions.

Specifically, hybridization of immobilized DNA in Southern blots with $^{32}P$-labeled gene specific probes was performed by standard methods (Maniatis et al.) In general, hybridization and subsequent washes were carried out under moderate to high stringency conditions that allowed for detection of target sequences with homology to the exemplified PPO sequences. For double-stranded DNA gene probes, hybridization can be carried out overnight at 20-25° C. below the melting temperature (Tm) of the DNA hybrid in 6×SSPE 5× Denhardt's solution, 0.1% SDS, 0.1 mg/ml denatured DNA. The melting temperature is described by the following formula (Beltz, G. A et al. (1983) Meth. Enzymol. R. Wu, et al. (eds.) Academic Press, New York 100:266-285).

Tm=81.5° C.+16.6 Log(Na+)+0.41(+G+C)-0.61(% formamide)−600/length of duplex in base pairs.

Washes are typically carried out as follows: twice at room temperature for 15 minutes in 1×SSPE, 0.1% SDS (low stringency wash), and once at TM-20° C. for 15 minutes in 0.2× SSPE, 0.1% SDS (moderate stringency wash).

For oligonucleotide probes, hybridization was carried out overnight at 10-20° C. below the melting temperature (Tm) of the hybrid 6×SSPE, 5× Denhardt's solution, 0.1% SDS, 0.1 mg/ml denatured DNA. Tm for oligonucleotide probes was determined by the following formula: TM(° C.)=2(number T/A base pairs +4(number G/C base pairs) (Suggs, S. V. et al. (1981) ICB-UCLA Symp. Dev. Biol. Using Purified Genes, D. D. Brown (ed.), Academic Press, New York, 23:683-693).

Washes were typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan.

Polymerase Chain Reaction (PCR) is a repetitive, enzymatic, primed synthesis and amplification of a nucleic acid sequence. This procedure is well known and commonly used by those skilled in this art (see, e.g., Mullis, U.S. Pat. Nos. 4,683,195, 4,683,202, and 4,800,159; Saiki et al. 1985. Science 230:1350-1354). Kits and reagents are readily available from commercial sources. The skilled artisan can routinely produce deletion-, insertion-, or substitution-type mutations and identify those resulting mutants which contain the desired characteristics of the specifically exemplified sequences, i.e., those which retain herbicide resistance and PPX2L activity, although other means for making mutations in a particular sequence are known to the art. Methods for confirming herbicide resistance and PPO activity are known in the art.

DNA sequences having at least 85, 90, 95%, and all integers from 85 to 99%, identity to the recited DNA sequences of Tables 3 and 5 and functioning to encode an herbicide resistant PPO are considered the most preferred equivalents to these sequences. Such functional equivalents are included in the definition of an herbicide resistant PPO coding sequence. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Karlin and Altschul. 1990. Proc. Natl. Acad. Sci. USA 87:2264-2268, modified as in Karlin and Altschul. 1993. Proc. Natl. Acad. Sci. USA 90:5873-5877. Such an algorithm is incorporated into the NBLAST and XBLAST programs of Altschul et al. 1990. J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. 1997. Nucl. Acids. Res. 25:3389-3402. When utilizing BLAST and Gapped BLAST programs, the default parameters of the respective programs (NBLAST and XBLAST) are used. See the National Center for Biotechnology Information website.

The choice of vector in which the DNA of interest is inserted depends, as is well known in the art, on the functional properties desired, e.g., replication, protein expression, and the host cell to be transformed. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells; others are well known.

Those vectors that include a prokaryotic replicon also typically include convenient restriction sites for insertion of a recombinant DNA molecule of the present invention; such vectors include pUC8, pUC9, pBR322, and pBR329. Vectors are available from BioRad Laboratories (Richmond, Calif.), Pharmacia (Piscataway, N.J.), Stratagene (La Jolla, Calif.), Promega Corporation, Madison, Wis., and many other commercial sources. The vector may also be a Lambda phage vector; see.e.g. *Molecular Cloning: A Laboratory Manual, Second Edition*, Maniatis et al., eds., Cold Spring Harbor Press (1989) and commercial sources. Other exemplary vectors include PCMU (Nilsson et al. (1989) *Cell* 58:707) and derivatives.

Typical expression vectors capable of expressing a recombinant nucleic acid sequence in plant cells and capable of directing stable integration within the host plant cell include vectors derived from the tumor-inducing (Ti) plasmid of *A. tumefaciens* described by Rogers et al. 1987. Meth. Enzymol. 153:253-277, and several other expression vector systems known to function in plants. See for example, WO87/00551; Cocking and Davey. 1987. Science 236:1259-1262.

A transgenic plant can be produced by any means known to the art, including but not limited to *A. tumefaciens*-mediated DNA transfer, *Agrobacterium rhizogenes*mediated DNA transfer, both preferably with a disarmed T-DNA vector, electroporation, direct DNA transfer, liposomes, diffusion, microinjection, virus vectors, calcium phosphate, and particle bombardment. Techniques are well-known to the art for the introduction of DNA into monocots as well as dicots, as are the techniques for culturing such plant tissues and regenerating those tissues.

Many of the procedures useful for practicing the present invention, whether or not described herein in detail, are well known to those skilled in the art of plant molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Glover (ed.) (1985) DNA Cloning Vol. I and II, IRL Press, Oxford, UK; Hames and Higgins (eds.) (1985) Nucleic Acid Hybridization, IRL Press, Oxford, UK; Kaufman (1987) in Genetic Engineering Principles and Methods, J. K. Setlow, ed., Plenum Press, NY, pp. 155-198; Fitchen et al. 1993. Annu. Rev. Microbiol. 47:739-764; Tolstoshev et al. (1993) in Genomic Research in Molecular Medicine and Virology, Academic Press. Abbreviations and nomenclature are standard in the field and commonly used in professional journals as cited herein.

All references and patent documents cited herein reflect the level of skill in the relevant arts and are incorporated by reference in their entireties to the extent there is no inconsistency with the present disclosure.

Where features or aspects of the invention are described in terms of Markush groups or other groupings of alternatives, those skilled in the art recognize that the invention is intended to relate to any individual member or subgroup of members of the Markush group or other group.

TABLE 3

| DNA Sequence encoding Herbicide resistant Waterhemp PPX2L (SEQ ID NO:13), derived from analysis of multiple cloning events |
|---|
| ATGGTAATTCAATCCATTACCCACCTTTCACCAAACCTTGCATTGCCATC<br>GCCATTGTCAGTTTCAACCAAGAACTACCCAGTAGCTGTAATGGGCAACA<br>TTTCTGAGCGGGAAGAACCCACTTCTGCTAAAAGGGTTGCTGTTGTTGGT<br>GCTGGAGTTAGTGGACTTGCTGCTGCATATAAGCTAAAATCCCATGGTTT<br>GAGTGTGACATTGTTTGAAGCTGATTCTAGAGCTGGAGGCAAACTTAAAA<br>CTGTTAAAAAAGATGGTTTTATTTGGGATGAGGGGGCAAATACTATGACA<br>GAAAGTGAGGCAGAGGTCTCGAGTTTGATCGATGATCTTGGGCTTCGTGA<br>GAAGCAACAGTTGCCAATTTCACAAAATAAAAGATACATAGCTAGAGACG<br>GTCTTCCTGTGCTACTACCTTCAAATCCCGCTGCACTACTCACGAGCAAT<br>ATCCTTTCAGCAAAATCAAAGCTGCAAATTATGTTGGAACCATTTCTCTG<br>GAGAAAACACAATGCTACTGAACTTTCTGATGAGCATGTTCAGGAAAGCG<br>TTGGTGAATTTTTTGAGCGACATTTTGGGAAAGAGTTTGTTGATTATGTT<br>ATCGACCCTTTTGTTGCGGGTACATGTGGAGATCCTCAATCGCTTTCCAT<br>GCACCATACATTTCCAGAAGTATGGAATATTGAAAAAAGGTTTGGCTCTG<br>TGTTTGCTGGACTAATTCAATCAACATTGTTATCTAAGAAGGAAAAGGGT<br>GGAGAAAATGCTTCTATTAAGAAGCCTCGTGTACGTGGTTCATTTTCATT<br>TCAAGGTGGAATGCAGACACTTGTTGACACAATGTGCAAACAGCTTGGTG<br>AAGATGAACTCAAACTCCAGTGTGAGGTGCTGTCCTTGTCATATAACCAG<br>AAGGGGATCCCCTCATTAGGGAATTGGTCAGTCTCTTCTATGTCAAATAA<br>TACCAGTGAAGATCAATCTTATGATGCTGTGGTTGTCACTGCTCCAATTC<br>GCAATGTCAAAGAAATGAAGATTATGAAATTTGGAAATCCATTTTCACTT<br>GACTTTATTCCAGAGGTGACGTACGTACCCCTTTCCGTTATGATTACTGC<br>ATTCAAAAAGGATAAAGTGAAGAGACCTCTTGAGGGCTTCGGAGTTCTTA<br>TCCCCTCTAAAGAGCAACATAATGGACTGAAGACTCTTGGTACTTTATTT<br>TCCTCCATGATGTTTCCTGATCGTGCTCCATCTGACATGTGTCTCTTTAC<br>TACATTTGTCGGAGGAAGCAGAAATAGAAAACTTGCAAACGCTTCAACGG<br>ATGAATTGAAGCAAATAGTTTCTTCTGACCTTCAGCAGCTGTTGGGCACT<br>GAGGACGAACCTTCATTTGTCAATCATCTCTTTTGGAGCAACGCATTCCC<br>ATTGTATGGACACAATTACGATTCTGTTTTGAGAGCCATAGACAAGATGG<br>AAAAGGATCTTCCTGGATTTTTTTATGCAGGTAACCATAAGGGTGGACTT<br>TCAGTGGGAAAAGCGATGGCCTCCGGATGCAAGGCTGCGGAACTTGTAAT<br>ATCCTATCTGGACTCTCATATATATGTGAAGATGGATGAGAAGACCGCGT<br>AA |

TABLE 4

| Herbicide-resistant PPO2 Protein Sequence (SEQ ID NO:14), derived from analysis of multiple cloning events. Bolded G corresponds to single glycine residue where sensitive protein has double glycine residue. |
|---|
| MVIQSITHLSPNLALPSPLSVSTKNYPVAVMGNISEREEPTSAKRVAVVG |
| AGVSGLAAAYKLKSHGLSVTLFEADSRAGGKLKTVKKDGFIWDEGANTMT |
| ESEAEVSSLIDDLGLREKQQLPISQNKRYIARDGLPVLLPSNPAALLTSN |
| ILSAKSKLQIMLEPFLWRKHNATELSDEHVQESVGEFFERHFGKEFVDYV |
| IDPFVAGTC**G**DPQSLSMHHTFPEVWNIEKRFGSVFAGLIQSTLLSKKEKG |
| GENASIKKPRVRGSFSFQGGMQTLVDTMCKQLGEDELKLQCEVLSLSYNQ |
| KGIPSLGNWSVSSMSNNTSEDQSYDAVVVTAPIRNVKEMKIMKFGNPFSL |
| DFIPEVTYVPLSVMITAFKKDKVKRPLEGFGVLIPSKEQHNGLKTLGTLF |
| SSMMFPDRAPSDMCLFTTFVGGSRNRKLANASTDELKQIVSSDLQQLLGT |
| EDEPSFVNHLFWSNAFPLYGHNYDSVLRAIDKMEKDLPGFFYAGNHKGGL |
| SVGKAMASGCKAAELVISYLDSHIYVKMDEKTA |

TABLE 5

| DNA Sequence Encoding Wild type (Herbicide-sensitive) Waterhemp PPO (SEQ ID NO:15), derived from analysis of multiple cloning events |
|---|
| ATGGTAATTCAATCCATTACCCACCTTTCACCAAACCTTGCATTGCCATC |
| GCCATTGTCAGTTTCAACCAAGAACTACCCAGTAGCTGTAATGGGCAACA |
| TTTCTGAGCGGGAAGAACCCACTTCTGCTAAAAGGGTTGCTGTTGTTGGT |
| GCTGGAGTTAGTGGACTTGCTGCTGCATATAAGCTAAAATCCCATGGTTT |
| GAGTGTGACATTGTTTGAAGCTGATTCTAGAGCTGGAGGCAAACTTAAAA |
| CTGTTAAAAAAGATGGTTTTATTTGGGATGAGGGGGCAAATACTATGACA |
| GAAAGTGAGGCAGAGGTCTCGAGTTTGATCGATGATCTTGGGCTTCGTGA |
| GAAGCAACAGTTGCCAATTTCACAAAATAAAAGATACATAGCTAGAGACG |
| GTCTTCCTGTGCTACTACCTTCAAATCCCGCTGCACTACTCACGAGCAAT |
| ATCCTTTCAGCAAAATCAAAGCTGCAAATTATGTTGGAACCATTTCTCTG |
| GAGAAAACACAATGCTACTGAACTTTCTGATGAGCATGTTCAGGAAAGCG |
| TTGGTGAATTTTTTGAGCGACATTTTGGGAAAGAGTTTGTTGATTATGTT |
| ATCGACCCTTTTGTTGCGGGTACATGTGGTGGAGATCCTCAATCGCTTTC |
| CATGCACCATACATTTCCAGAAGTATGGAATATTGAAAAAAGGTTTGGCT |
| CTGTGTTTGCTGGACTAATTCAATCAACATTGTTATCTAAGAAGGAAAAG |
| GGTGGAGAAAATGCTTCTATTAAGAAGCCTCGTGTACGTGGTTCATTTTC |

TABLE 5-continued

| DNA Sequence Encoding Wild type (Herbicide-sensitive) Waterhemp PPO (SEQ ID NO:15), derived from analysis of multiple cloning events |
|---|
| ATTTCAAGGTGGAATGCAGACACTTGTTGACACAATGTGCAAACAGCTTG |
| GTGAAGATGAACTCAAACTCCAGTGTGAGGTGCTGTCCTTGTCATATAAC |
| CAGAAGGGGATCCCCTCATTAGGGAATTGGTCAGTCTCTTCTATGTCAAA |
| TAATACCAGTGAAGATCAATCTTATGATGCTGTGGTTGTCACTGCTCCAA |
| TTCGCAATGTCAAAGAAATGAAGATTATGAAATTTGGAAATCCATTTTCA |
| CTTGACTTTATTCCAGAGGTGACGTACGTACCCCTTTCCGTTATGATTAC |
| TGCATTCAAAAAGGATAAAGTGAAGAGACCTCTTGAGGGCTTCGGAGTTC |
| TTATCCCCTCTAAAGAGCAACATAATGGACTGAAGACTCTTGGTACTTTA |
| TTTTCCTCCATGATGTTTCCTGATCGTGCTCCATCTGACATGTGTCTCTT |
| TACTACATTTGTCGGAGGAAGCAGAAATAGAAAACTTGCAAACGCTTCAA |
| CGGATGAATTGAAGCAAATAGTTTCTTCTGACCTTCAGCAGCTGTTGGGC |
| ACTGAGGACGAACCTTCATTTGTCAATCATCTCTTTTGGAGCAACGCATT |
| CCCATTGTATGGACACAATTACGATTCTGTTTTGAGAGCCATAGACAAGA |
| TGGAAAAGGATCTTCCTGGATTTTTTTATGCAGGTAACCATAAGGGTGGA |
| CTTTCAGTGGGAAAAGCGATGGCCTCCGGATGCAAGGCTGCGGAACTTGT |
| AATATCCTATCTGGACTCTCATATATATGTGAAGATGGATGAGAAGACCG |
| CGTAA |

TABLE 6

| Wild type Waterhemp PPO Amino Acid Sequence (SEQ ID NO:16), derived from analysis of multiple cloning events |
|---|
| MVIQSITHLSPNLALPSPLSVSTKNYPVAVMGNISEREEPTSAKRVAVVG |
| AGVSGLAAAYKLKSHGLSVTLFEADSRAGGKLKTVKKDGFIWDEGANTMT |
| ESEAEVSSLIDDLGLREKQQLPISQNKRYIARDGLPVLLPSNPAALLTSN |
| ILSAKSKLQIMLEPFLWRKHNATELSDEHVQESVGEFFERHFGKEFVDYV |
| IDPFVAGTCGGDPQSLSMHHTFPEVWNIEKRFGSVFAGLIQSTLLSKKEK |
| GGENASIKKPRVRGSFSFQGGMQTLVDTMCKQLGEDELKLQCEVLSLSYN |
| QKGIPSLGNWSVSSMSNNTSEDQSYDAVVVTAPIRNVKEMKIMKFGNPFS |
| LDFIPEVTYVPLSVMITAFKKDKVKRPLEGFGVLIPSKEQHNGLKTLGTL |
| FSSMMFPDRAPSDMCLFTTFVGGSRNRKLANASTDELKQIVSSDLQQLLG |
| TEDEPSFVNHLFWSNAFPLYGHNYDSVLRAIDKMEKDLPGFFYAGNHKGG |
| LSVGKAMASGCKAAELVISYLDSHIYVKMDEKTA |

TABLE 7

| Amino acid and cDNA sequences of herbicide-susceptible *Amaranthus tuberculatus* biotype WC plastid protoporphyrinogen oxidase (PPX1) mRNA, complete cds; nuclear gene for plastid product, corresponding to NCBI ACCESSION DQ386112; SEQ ID NO:17 (cDNA) and NO:18 (amino acid) |
|---|
| MSAMALSSSILQCPPHSDISFRFFAHTRTQPPIFFGRPRKLSYIHCSTSSSSTANYQNTITSQGEGDKVL |
| DCVIVGAGISGLCIAQALSTKHIQSNLNFIVTEAKHRVGGNITTMESDGYIWEEGPNSFQPSDPVLTMAV |
| DSGLKDDLVLGDPNAPRFVLWNGKLRPVPSKPTDLPFFDLMSFPGKIRAGLGALGLRPPPPSYEESVEEF |
| VRRNLGDEVFERLIEPFCSGVYAGDPAKLSMKAAFGKVWTLEQKGGSIIAGTLKTIQERKNNPPPRDPR |
| LPKPKGQTVGSFRKGLIMLPTAIAARLGSKVKLSWTLSNIDKSLNGEYNLTYQTPDGPVSVRTKAVVMTV |
| PSYIASSLLRPLSDVAADSLSKFYYPPVAAVSLSYPKEAIRPECLIDGELKGFGQLHPRSQGVETLGTIY |
| SSSLFPGRAPPGRTLILSYIGGATNLGILQKSEDELAETVDKDLRKILINPNAKGSRVLGVRVWPKAIPQ |
| FLVGHFDVLDAAKAGLANAGQKGLFLGGNYVSGVALGRCIEGAYDSASEVVDFLSQYKDK |
| 1 atgagtgcga tggcgttatc gagcagcatt ctacaatgtc cgccgcactc cgacatctcg |
| 61 ttccgctttt ttgctcatac acgaacccaa ccccccatct tcttcggaag accacgaaaa |
| 121 ttatcatata tccattgttc cacaagctca agctcaactg ccaattacca gaacaccatt |
| 181 acgagccaag gagaaggaga taaagtatta gattgtgtaa ttgttggagc tggtatcagt |
| 241 ggactttgca ttgctcaggc tctttctacc aaacacattc aatccaatct caatttcatt |
| 301 gtcactgaag ctaaacatcg tgttggaggt aatatcacta ccatggagtc cgatggctat |
| 361 atctgggaag agggtcctaa tagtttccaa ccctccgatc ctgtgcttac tatggcggtt |
| 421 gacagtggat tgaaagacga tttggtcttg ggagatccta atgcccctcg tttcgtgctc |
| 481 tggaatggta aattaaggcc tgttccttcc aaacctacgg accttccctt ttttgatctc |

TABLE 7-continued

Amino acid and cDNA sequences of herbicide-susceptible *Amaranthus tuberculatus* biotype WC plastid protoporphyrinogen oxidase (PPX1) mRNA, complete cds; nuclear gene for plastid product, corresponding to NCBI ACCESSION DQ386112; SEQ ID NO:17 (cDNA) and NO:18 (amino acid)

541 atgagctttc ctggtaagat tagggctggt cttggtgcac ttggtcttcg tcctcctcct 601 ccttcttatg aggaatctgt tgaagaattt gtgcgccgta atctcggcga tgaggtcttc 661 gaacgcttga tcgaaccctt ttgttctggt gtctatgctg gtgatcctgc aaagttgagt 721 atgaaagctg catttggaaa ggtctggacc ttagagcaaa agggtggtag tatcatagcc 781 ggtacactca aaactattca ggaaaggaaa aataatcctc cacccccctcg agaccccccgc 841 cttcctaaac ctaagggcca gactgttgga tcctttagga aagggctcat tatgttacct 901 accgccattg ctgctaggct tggcagtaaa gtcaaactat cgtggacact ttctaatatt 961 gataagtcgc tcaatggaga atacaatctc acttatcaaa cacccgatgg accggtttct 1021 gttaggacca aagcggttgt catgaccgtc ccttcgtaca ttgcaagtag cttgcttcgt 1081 ccgctctcag atgttgctgc agattctctt tctaaatttt actatccacc agtcgcagca 1141 gtgtcccttt cttatcccaa agaagcaatt agaccagaat gcttgatcga tggtgaacta 1201 aaaggattcg ggcaattgca tccccgcagc cagggtgtgg aaaccttggg aacaatttat 1261 agttcatctc ttttccctgg tcgagcaccc cccggtagga ccttgatctt gagctacatt 1321 ggaggtgcta caaatcttgg catattacaa aagagtgaag atgaacttgc ggagacagtt 1381 gataaggatc tcagaaaaat tctgataaat ccaaatgcga aaggcagccg tgttctggga 1441 gtgagagtat ggccaaaagc aatcccccaa tttttagttg gtcactttga tgtgctagat 1501 gctgcaaaag ctggtttggc aaatgctggg caaaaggggt tgtttcttgg tggtaattat 1561 gtatcaggtg ttgccttggg gaggtgtata gagggtgctt atgactctgc ttctgaggta 1621 gtggatttcc tctcacagta caaagataag tag

TABLE 8

Coding and amino acid sequences of *Amaranthus tuberculatus* biotype herbicide-susceptible WC mitochondrial protoporphyrinogen oxidase (PPX2) mRNA, nuclear gene for mitochondrial product, corresponding to NCBI Accession DQ386113 and SEQ ID NO:19 (cDNA) and NO:20 (amino acid)

MGNISERDEPTSAKRVAVVGAGVSGLAAAYKLKSHGLNVTLFEADSRAGGKLKTVKKDGFIWDEGANTMT
ESEAEVSSLIDDLGLREKQQLPISQNKRYIARDGLPVLLPSNPAALLTSNILSAKSKLQIMLEPFFWRKH
NATELSDEHVQESVGEFFERHFGKEFVDYVIDPFVAGTCGGDPQSLSMHHTFPEVWNIEKRFGSVFAGLI
QSTLLSKKEKGGGGNASIKKPRVRGSFSFHGGMQTLVDTICKQLGEDELKLQCEVLSLSYNQKGIPSLGN
WSVSSMSNNTSEDQSYDAVVVTAPIRNVKEMKIMKFGNPFSLDFIPEVSYVPLSVMITAFKKDKVKRPLE
GFGVLIPSKEQHNGLKTLGTLFSSMMFPDRAPSDMCLFTTFVGGSRNRKLANASTDELKQIVSSDLQQLL
GTEDEPSFVNHLFWSNAFPLYGHNYDSVLRAIDKMEKDLPGFFYAGNHKGGLSVGKAMASGCKAAELVIS
YLDSHIYVKMDEKTA 1 atgggcaaca tttctgagcg ggatgaaccc acttctgcta aaagggttgc tgttgttggt 61 gctggagtta gtggacttgc tgctgcatat aagctaaaat cccatggttt gaatgtgaca 121 ttgtttgaag ctgattctag agctggaggc aaacttaaaa ctgttaaaaa agatggtttt 181 atttgggatg agggggcaaa tactatgaca gaaagtgagg cagaagtctc gagtttgatc 241 gatgatcttg ggcttcgtga gaagcaacag ttgccaattt cacaaaataa aagatacata 301 gctagagatg gtcttcctgt gctactacct tcaaatcccg ctgcactgct cacgagcaat 361 atcctttcag caaaatcaaa gctgcaaatt atgttggaac catttttctg gagaaaacac 421 aatgctactg agctttctga tgagcatgtt caggaaagcg ttggtgaatt ttttgagcga TABLE 8-continued

| Coding and amino acid sequences of *Amaranthus tuberculatus* biotype herbicide-susceptible WC mitochondrial protoporphyrinogen oxidase (PPX2) mRNA, nuclear gene for mitochondrial product, corresponding to NCBI Accession DQ386113 and SEQ ID NO:19 (cDNA) and NO:20 (amino acid) |
|---|
| 481 cattttggga aagagtttgt tgattatgtt attgaccctt ttgttgcggg tacatgtggt |
| 541 ggagatcctc aatcgctttc tatgcaccat acatttccag aagtatggaa tattgaaaaa |
| 601 aggtttggct ctgtgtttgc tggactaatt caatcaacat tgttatctaa gaaggaaaag |
| 661 ggtggaggag gaaatgcttc tatcaagaag cctcgtgtac gtggttcatt ttcattccat |
| 721 ggtggaatgc agacacttgt tgacacaata tgcaaacagc ttggtgaaga tgaactcaaa |
| 781 ctccagtgtg aggtgctgtc cttgtcatac aaccagaagg ggatcccttc attagggaat |
| 841 tggtcagtct cttctatgtc aaataatacc agtgaagatc aatcttatga tgctgtggtt |
| 901 gtcactgctc caattcgcaa tgtcaaagaa atgaagatta tgaaattcgg aaatccattt |
| 961 tcacttgact ttattccaga ggtgagttac gtacccctct ctgttatgat tactgcattc |
| 1021 aagaaggata aagtgaagag accactcgag ggctttggag ttcttatccc ctctaaagag |
| 1081 caacataatg gactgaagac tcttggtact ttattttcct ccatgatgtt tcccgatcgt |
| 1141 gctccatctg acatgtgtct ctttactaca tttgtcggag gaagcagaaa tagaaaactt |
| 1201 gcaaacgctt caacggatga attgaagcaa atagtttctt ctgaccttca gcagctgttg |
| 1261 ggcactgagg acgaaccttc atttgtcaat catctctttt ggagcaacgc attcccgttg |
| 1321 tatggacaca attacgattc tgttttgaga gccatagaca agatggaaaa ggatcttcct |
| 1381 ggattttttt atgcaggtaa ccataagggt ggactttcag tgggaaaagc gatggcctcc |
| 1441 ggatgcaagg ctgcggaact tgtaatatcc tatctggact ctcatatata tgtgaagatg |
| 1501 gatgagaaga ccgcgtaa |

TABLE 9

| Coding and amino acid sequence of *Amaranthus tuberculatus* biotype herbicide-susceptible WC mitochondrial protoporphyrinogen oxidase (PPX2L) mRNA, nuclear gene for mitochondrial product, corresponding to NCBI Accession DQ386114 and SEQ ID NO:21 (cDNA) and NO:22 (amino acid) |
|---|
| MVIQSITHLSPNLALPSPLSVSTKNYPVAVMGNISEREEPTSAKRVAVVGAGVSGLAAAYKLKSHGLSVT<br>LFEADSRAGGKLKTVKKDGFIWDEGANTMTESEAEVSSLIDDLGLREKQQLPISQNKRYIARDGLPVLLP<br>SNPAALLTSNILSAKSKLQIMLEPFLWRKHNATELSDEHVQESVGEFFERHFGKEFVDYVIDPFVAGTCG<br>GDPQSLSMHHTFPEVWNIEKRFGSVFAGLIQSTLLSKKEKGGENASIKKPRVRGSFSFQGGMQTLVDTMC<br>KQLGEDELKLQCEVLSLSYNQKGIPSLGNWSVSSMSNNTSEDQSYDAVVVTAPIRNVKEMKIMKFGNPFS<br>LDFIPEVTYVPLSVMITAFKKDKVKRPLEGFGVLIPSKEQHNGLKTLGTLFSSMMFPDRAPSDMCLFTTF<br>VGGSRNRKLANASTDELKQIVSSDLQQLLGTEDEPSFVNHLFWSNAFPLYGHNYDSVLRAIDKMEKDLPG<br>FFYAGNHKGGLSVGKAb4ASGCKAAELVISYLDSHIYVKMDEKTA |
| 1 atggtaattc aatccattac ccacctttca ccaaaccttg cattgccatc gccattgtca |
| 61 gtttcaacca agaactaccc agtagctgta atgggcaaca tttctgagcg ggaagaaccc |
| 121 acttctgcta aaagggttgc tgttgttggt gctggagtta gtggacttgc tgctgcatat |
| 181 aagctaaaat cccatggttt gagtgtgaca ttgtttgaag ctgattctag agctggaggc |
| 241 aaacttaaaa ctgttaaaaa agatggtttt atttgggatg agggggcaaa tactatgaca |
| 301 gaaagtgagg cagaggtctc gagtttgatc gatgatcttg ggcttcgtga gaagcaacag |
| 361 ttgccaattt cacaaaataa aagatacata gctagagacg gtcttcctgt gctactacct |
| 421 tcaaatcccg ctgcactact cacgagcaat atcctttcag caaaatcaaa gctgcaaatt |
| 481 atgttggaac catttctctg gagaaaacac aatgctactg aactttctga tgagcatgtt |
| 541 caggaaagcg ttggtgaatt ttttgagcga cattttggga aagagtttgt tgattatgtt |

TABLE 9-continued

Coding and amino acid sequence of *Amaranthus tuberculatus* biotype herbicide-susceptible WC mitochondrial protoporphyrinogen oxidase (PPX2L) mRNA, nuclear gene for mitochondrial product, corresponding to NCBI Accession DQ386114 and SEQ ID NO:21 (cDNA) and NO:22 (amino acid)

```
 601 atcgaccctt ttgttgcggg tacatgtggt ggagatcctc aatcgctttc catgcaccat

 661 acatttccag aagtatggaa tattgaaaaa aggtttggct ctgtgtttgc tggactaatt

 721 caatcaacat tgttatctaa gaaggaaaag ggtggagaaa atgcttctat taagaagcct

 781 cgtgtacgtg gttcattttc atttcaaggt ggaatgcaga cacttgttga cacaatgtgc

 841 aaacagcttg gtgaagatga actcaaactc cagtgtgagg tgctgtcctt gtcatataac

 901 cagaagggga tcccctcatt agggaattgg tcagtctctt ctatgtcaaa taataccagt

 961 gaagatcaat cttatgatgc tgtggttgtc actgctccaa ttcgcaatgt caaagaaatg

1021 aagattatga aatttggaaa tccattttca cttgacttta ttccagaggt gacgtacgta

1081 ccccttttccg ttatgattac tgcattcaaa aaggataaag tgaagagacc tcttgagggc

1141 ttcggagttc ttatcccctc taaagagcaa cataatggac tgaagactct tggtacttta

1201 ttttcctcca tgatgtttcc tgatcgtgct ccatctgaca tgtgtctctt tactacattt

1261 gtcggaggaa gcagaaatag aaaacttgca aacgcttcaa cggatgaatt gaagcaaata

1321 gtttcttctg accttcagca gctgttgggc actgaggacg aaccttcatt tgtcaatcat

1381 ctcttttgga gcaacgcatt cccattgtat ggacacaatt acgattctgt tttgagagcc

1441 atagacaaga tggaaaagga tcttcctgga tttttttatg caggtaacca taagggtgga

1501 ctttcagtgg gaaaagcgat ggcctccgga tgcaaggctg cggaacttgt aatatcctat

1561 ctggactctc atatatacgt gaagatggat gagaagaccg cgtaa //
```

TABLE 10

*Amaranthus tuberculatus* biotype herbicide-resistant AC plastid protoporphyrinogen oxidase (PPX1) mRNA, nuclear gene for plastid product, corresponding to NCBI Accession DQ386115 and SEQ ID NO:23 (cDNA) and NO:24 (amino acid)

```
MSAMALSSSILQCPPHSDISFRFFAHTRTPSPIFFGRTRKLSYIHCSTSSSSTANYQNTITSQGEGDKVL
DCVIVGAGISGLCIAQALSTKHIQSNLNFIVTEAKHRVGGNITTMESDGYIWEEGPNSFQPSDPVLTMAV
DSGLKDDLVLGDPNAPRFVLWNGKLRPVPSKPTDLPFFDLMSFPGKIRAGLGALGLRPPPPPPSYEESVE
EFVRRNLGDEVFERLIEPFCSGVYAGDPAKLSMKAAFGKVWTLEQKGGSIIAGTLKTIQERKNNPPPPRD
PRLPKPKGQTVGSFRKGLIMLPTAIAARLGSKVKLSWTLSNIDKSLNGEYNLTYQTPDGPVSVRTKAVVM
TVPSYIASSLLRPLSDVAADSLSKFYYPPVAAVSLSYPKEAIRPECLIDGELKGFGQLHPRSQGVETLGT
IYSSSLFPGRAPPGRTLILSYIGGATNLGILQKSEDELAETVDKDLRKILINPNAKGSRVLGVRVWPKAI
PQFLVGHFDVLDAAKAGLANAGLKGLFLGGNYVSGVALGRCIEGAYDSASEVVDFLSQYKDK
   1 atgagtgcga tggcgttatc gagcagcatt ctacaatgtc cgccgcactc cgacatctcg

  61 ttccgctttt ttgctcatac acgaacccca tcccccatct tcttcggaag aacacgaaaa

 121 ttatcatata tccattgttc cacaagctca agctcaactg ccaattacca gaacacgatt

 181 acgagccaag gagaaggaga taaagtatta gattgtgtaa ttgttggagc tggtatcagt

 241 ggactttgca ttgctcaggc tctttctacc aaacacattc aatccaatct caatttcatt

 301 gtcactgaag ctaaacatcg tgttggaggt aatatcacta ccatggagtc cgatggctat

 361 atctgggaag agggtcctaa tagtttccaa ccctccgatc ctgtgcttac tatggcggtt

 421 gacagtggat tgaaagacga tttagtcttg ggagatccta atgcccctcg tttcgtgctc

 481 tggaatggta aattaaggcc tgttccttcc aaacctacgg accttccctt ttttgatctc

 541 atgagctttc ctggtaagat tagggctggt cttggtgcac ttggtcttcg tcctcctcct

 601 cctcctcctt cttatgagga atctgttgaa gaatttgtgc gccgtaatct cggcgatgag
```

TABLE 10-continued

*Amaranthus tuberculatus* biotype herbicide-resistant AC plastid protoporphyrinogen oxidase (PPX1) mRNA, nuclear gene for plastid product, corresponding to NCBI Accession DQ386115 and SEQ ID NO:23 (cDNA) and NO:24 (amino acid)

661 gtcttcgaac gcttgatcga accctttgt tctggtgtct atgctggtga tcctgcaaag 721 ttgagtatga aagctgcatt tggaaaggtc tggaccttag agcaaaaggg tggtagtatc 781 atagccggta cactcaaaac tattcaggaa aggaaaaata atcctccacc ccctcgagac 841 ccccgccttc ctaaacctaa gggccagact gttggatcct ttaggaaagg gctcattatg 901 ttacctaccg ccattgctgc taggcttggc agtaaagtca aactatcgtg gacactttct 961 aatattgata agtcgctcaa tggagaatac aatctcactt atcaaacacc cgatggaccg 1021 gtttctgtta ggaccaaagc ggttgtcatg accgtccctt cgtacattgc aagtagcttg 1081 cttcgtccgc tctcagatgt tgctgcagat tctctttcta aattttacta tccaccagtc 1141 gcagcagtgt ccctttctta tcccaaagaa gcaattagac cagaatgctt gattgatgga 1201 gaactaaaag gattcgggca attgcatccc cgcagccagg gtgtggaaac cttgggaaca 1261 atttatagtt catctctttt ccctggtcga gcaccacccg gtaggacctt gatcttgagc 1321 tacattggag gtgctacaaa tcttggcata ttacaaaaga gtgaagatga actcgcggag 1381 acagttgata aggatctcag aaaaattctg ataaatccaa atgcgaaagg cagccgtgtt 1441 ctgggagtga gagtatggcc aaaggcaatc ccccaatttt tagttggtca ctttgatgtg 1501 ctagatgctg caaaagctgg tttggcaaat gctgggctaa aggggttgtt tcttggtggt 1561 aattatgtat caggtgttgc cttggggagg tgtatagagg gtgcttatga ctctgcttct 1621 gaggtagtgg atttcctctc acagtacaaa gataagtag //

TABLE 11

*Amaranthus tuberculatus* biotype herbicide-resistant AC mitochondrial protoporphyrinogen oxidase (PPX2L) mRNA, complete cds; nuclear gene for mitochondrial product, corresponding to NCBI Accession DQ386116 and to SEQ ID NO:25 (cDNA) and NO:26 (amino acid)

MVIQSITHLSPNLALPSPLSVSTKNYPVAVMGNISEREEPTSAKRVAVVGAGVSGLAAAYKLKSHGLSVT
LFEADSRAGGKLKTVKKDGFIWDEGANTMTESEAEVSSLIDDLGLREKQQLPISQNKRYIARDGLPVLLP
SNPAALLTSNILSAKSKLQIMLEPFLWRKHNATELSDEHVQESVGEFFERHFGKEFVDYVIDPFVAGTCG
DPQSLSMHHTFPEVWNIEKRFGSVFAGLIQSTLLSKKEKGGENASIKKPRVRGSFSFQGGMQTLVDTMCK
QLGEDELKLQCEVLSLSYNQKGIPSLGNWSVSSMSNNTSEDQSYDAVVVTAPIRNVKEMKIMKFGNPFSL
DFIPEVTYVPLSVMITAFKKDKVKRPLEGFGVLIPSKEQHNGLKTLGTLFSSMMFPDRAPSDMCLFTTFV
GGSRNRKLANASTDELKQIVSSDLQQLLGTEDEPSFVNHLFWSNAFPLYGHNYDCVLRAIDKMEKDLPGF
FYAGNHKGGLSVGKAMASGCKAAELVISYLDSHIYVKMDEKTA 1 atggtaattc aatccattac ccacctttca ccaaaccttg cattgccatc gccattgtca 61 gtttccacca agaactaccc agtagctgta atgggcaaca tttctgagcg agaagaaccc 121 acttctgcta aaagggttgc tgttgttggt gctggagtta gtggacttgc tgctgcatat 181 aagctaaaat cccatggttt gagtgtgaca ttgtttgaag ctgattctag agctggaggc 241 aaacttaaaa ctgttaaaaa agatggtttt atttgggatg agggggcaaa tactatgaca 301 gaaagtgagg cagaggtctc gagtttgatc gatgatcttg ggcttcgtga gaagcaacag 361 ttgccaattt cacaaaataa aagatacata gctagagacg gtcttcctgt gctactacct 421 tcaaatcccg ctgcactact cacgagcaat atcctttcag caaaatcaaa gctgcaaatt 481 atgttggaac catttctctg gagaaaacac aatgctactg aactttctga tgagcatgtt 541 caggaaagcg ttggtgaatt ttttgagcga cattttggga aagagtttgt tgattatgtt 601 attgaccctt ttgttgcggg tacatgtgga gatcctcaat cgctttccat gcaccataca TABLE 11-continued

*Amaranthus tuberculatus* biotype herbicide-resistant AC mitochondrial protoporphyrinogen oxidase (PPX2L) mRNA, complete cds; nuclear gene for mitochondrial product, corresponding to NCBI Accession DQ386116 and to SEQ ID NO:25 (cDNA) and NO:26 (amino acid)

```
 661 tttccagaag tatggaatat tgaaaaaagg tttggctctg tgtttgctgg actaattcaa
 721 tcaacattgt tatctaagaa ggaaaagggt ggagaaaatg cttctattaa gaagcctcgt
 781 gtacgtggtt cattttcatt tcaaggtgga atgcagacac ttgttgacac aatgtgcaaa
 841 cagcttggtg aagatgaact caaactccag tgtgaggtgc tgtccttgtc atataaccag
 901 aaggggatcc cctcattagg gaattggtca gtctcttcta tgtcaaataa taccagtgaa
 961 gatcaatctt atgatgctgt ggttgtcact gctccaattc gcaatgtcaa agaaatgaag
1021 attatgaaat ttggaaatcc attttcactt gactttattc cagaggtgac gtacgtaccc
1081 ctttccgtta tgattactgc attcaaaaag gataaagtga agagacctct tgagggcttc
1141 ggagttctta tcccctctaa agagcaacat aatggactga agactcttgg tactttattt
1201 tcctccatga tgtttcctga tcgtgctcca tctgacatgt gtctctttac tacatttgtc
1261 ggaggaagca gaaatagaaa acttgcaaac gcttcaacgg atgaattgaa gcaaatagtt
1321 tcttctgacc ttcagcagct gttgggcact gaggacgaac cttcatttgt caatcatctc
1381 ttttggagca acgcattccc attgtatgga cacaattacg attgtgtttt gagagccata
1441 gacaagatgg aaaaggatct tcctggattt ttttatgcag gtaaccataa gggtggactt
1501 tcagtgggaa aagcgatggc ctccggatgc aaggctgcgg aacttgtaat atcctatctg
1561 gactctcata tatacgtgaa gatggatgag aagaccgcgt aa //
```

TABLE 12

*Amaranthus tuberculatus* biotype herbicide-susceptible AC mitochondrial protoporphyrinogen oxidase (PPX2L) mRNA, nuclear gene for mitochondrial product, corresponding to NCBI Accession DQ386117 and to SEQ ID NO:27 and NO:28

```
MVIQSITHLSPNLALPSPLSVSTKNYPVAVMGNISEREEPTSAKRVAVVGAGVSGLAAAYKLKSHGLSVT
LFEADSRAGGKLKTVKKDGFIWDEGANTMTESEAEVSSLIDDLGLREKQQLPISQNKRYIARAGLPVLLP
SNPAALLTSNILSAKSKLQIMLEPFLWRKHNATELSDEHVQESVGEFFERHFGKEFVDYVIDPFVAGTCG
GDPQSLSMHHTFPEVWNIEKRFGSVFAGLIQSTLLSKKEKGGENASIKKPRVRGSFSFQGGMQTLVDTMC
KQLGEDELKLQCEVLSLSYNQKGIPSLGNWSVSSMSNNTSEDQSYDAVVVTAPIRNVKEMKIMKFGNPFS
LDFIPEVTYVPLSVMITAFKKDKVKRPLEGFGVLIPSKEQHNGLKTLGTLFSSMMFPDRAPSDMCLFTTF
VGGSRNRKLANASTDELKQIVSSDLQQLLGTEDEPSFVNHLFWSNAFPLYGHNYDSVLRAIDKMEKDLPG
FFYAGNHKGGLSVGKAMASGCKAAELVISYLDSHIYVKMDEKTA
   1 atggtaattc aatccattac ccacctttca ccaaaccttg cattgccatc gccattgtca
  61 gtttcaacca agaactaccc agtagctgta atgggcaaca tttctgagcg ggaagaaccc
 121 acttctgcta aaagggttgc tgttgttggt gctggagtta gtggacttgc tgctgcatat
 181 aagctaaaat cccatggttt gagtgtgaca ttgtttgaag ctgattctag agctggaggc
 241 aaacttaaaa ctgttaaaaa agatggtttt atttgggatg agggggcaaa tactatgaca
 301 gaaagtgagg cagaggtctc gagtttgatc gatgatcttg ggcttcgtga gaagcaacag
 361 ttgccaattt cacaaaataa aagatacata gctagagccg gtcttcctgt gctactacct
 421 tcaaatcccg ctgcactact cacgagcaat atcctttcag caaaatcaaa gctgcaaatt
 481 atgttggaac catttctctg gagaaaacac aatgctactg aactttctga tgagcatgtt
 541 caggaaagcg ttggtgaatt ttttgagcga catttggga aagagtttgt tgattatgtt
 601 attgaccctt ttgttgcggg tacatgtggt ggagatcctc aatcgctttc catgcaccat
 661 acatttccag aagtatggaa tattgaaaaa aggtttggct ctgtgtttgc cggactaatt
```

TABLE 12-continued

*Amaranthus tuberculatus* biotype herbicide-susceptible AC mitochondrial protoporphyrinogen oxidase (PPX2L) mRNA, nuclear gene for mitochondrial product, corresponding to NCBI Accession DQ386117 and to SEQ ID NO:27 and NO:28

721 caatcaacat tgttatctaa gaaggaaaag ggtggagaaa atgcttctat taagaagcct 781 cgtgtacgtg gttcattttc atttcaaggt ggaatgcaga cacttgttga cacaatgtgc 841 aaacagcttg gtgaagatga actcaaactc cagtgtgagg tgctgtcctt gtcatataac 901 cagaagggga tcccctcact agggaattgg tcagtctctt ctatgtcaaa taataccagt 961 gaagatcaat cttatgatgc tgtggttgtc actgctccaa ttcgcaatgt caaagaaatg 1021 aagattatga aatttggaaa tccattttca cttgacttta ttccagaggt gacgtacgta 1081 ccccttttccg ttatgattac tgcattcaaa aaggataaag tgaagagacc tcttgagggc 1141 ttcggagttc ttatcccctc taaagagcaa cataatggac tgaagactct tggtacttta 1201 ttttcctcca tgatgtttcc tgatcgtgct ccatctgaca tgtgtctctt tactacattt 1261 gtcggaggaa gcagaaatag aaaacttgca aacgcttcaa cggatgaatt gaagcaaata 1321 gtttcttctg accttcagca gctgttgggc actgaggacg aaccttcatt tgtcaatcat 1381 ctcttttgga gcaacgcatt cccattgtat ggacacaatt acgattctgt tttgagagcc 1441 atagacaaga tggaaaagga tcttcctgga ttttttttatg caggtaacca taagggtgga 1501 ctttcagtgg gaaaagcgat ggcctccgga tgcaaggctg cggaacttgt aatatcctat 1561 ctggactctc atatatacgt gaagatggat gagaagaccg cgtaa //

TABLE 13

*Amaranthus tuberculatus* biotype herbicide-resistant CC mitochondrial protoporphyrinogen oxidase (PPX2L) mRNA, nuclear gene for mitochondrial product, corresponding to Accession DQ386118 and SEQ ID NO:29 and NO:30.

MVIQSITHLSPNLALPSPLSVSTKNYPVAVMGNISEREEPTSAKRVAVVGAGVSGLAAAYKLKSHGLSVT
LFEANSRAGGKLKTVKKDGFIWDEGANTMTESEAEVSSLIDDLGLREKQQLPISQNKRYIARDGLPVLLP
SNPAALLTSNILSAKSKLQIMLEPFLWRKHNATELSDEHVQESVGEFFERHFGKEFVDYVIDPFVAGTCG
DPQSLSMYHTFPEVWNIEKRFGSVFAGLIQSTLLSKKEKGGENASIKKPRVRGSFSFQGGMQTLVDTMCK
QLGEDELKLQCEVLSLSYNQKGIPSLGNWSVSSMSNNTSEDQSYDAVVVTAPIRNVKEMKIMKFGNPFSL
DFIPEVTYVPLSVMITAFKKDKVKRPLEGFGVLIPSKEQHNGLKTLGTLFSSMMFPDRAPSDMCLFTTFV
GGSRNRKLANASTDELKQIVSSDLQQLLGTEDEPSFVNHLFWSNAFPLYGHNYDSVLRAIDKMEKDLPGF
FYAGNHKGGLSVGKAMASGCKAAELVISYLDSHIYVKMDEKTA 1 atggtaattc aatccattac ccacctttca ccaaaccttg cattgccatc gccattgtca 61 gtttccacca agaactaccc agtagctgta atgggcaaca tttctgagcg ggaagaaccc 121 acttctgcta aaagggttgc tgttgttggt gctggagtta gtggacttgc tgctgcatat 181 aagctaaaat cccatggttt gagtgtgaca ttgtttgaag ctaattctag agctggaggc 241 aaacttaaaa ctgttaaaaa agatggtttt atttgggatg agggggcaaa tactatgaca 301 gaaagtgagg cagaggtctc gagtttgatc gatgatcttg ggcttcgtga gaagcaacag 361 ttgccaattt cacaaaataa aagatacata gctagagacg gtcttcctgt gctactacct 421 tcaaatcccg ctgcactact cacgagcaat atcctttcag caaaatcaaa gctgcaaatt 481 atgttggaac catttctctg gagaaaacac aatgctactg aactttctga tgagcatgtt 541 caggaaagcg ttggtgaatt ttttgagcga cattttggga aagagtttgt tgattatgtt 601 attgaccctt ttgttgcggg tacatgtgga gatcctcaat cgctttccat gtaccataca 661 tttccagaag tatggaatat tgaaaaaagg tttggctctg tgtttgctgg actaattcaa 721 tcaacattgt tatctaagaa ggaaaagggt ggagaaaatg cttctattaa gaagcctcgt TABLE 13-continued

*Amaranthus tuberculatus* biotype herbicide-resistant CC mitochondrial protoporphyrinogen oxidase (PPX2L) mRNA, nuclear gene for mitochondrial product, corresponding to Accession DQ386118 and SEQ ID NO:29 and NO:30.

```
 781 gtacgtggtt cattttcatt tcaaggtgga atgcagacac ttgttgacac aatgtgcaaa

 841 cagcttggtg aagatgaact caaactccag tgtgaggtgc tgtccttgtc atataaccag

 901 aaggggatcc cctcattagg gaattggtca gtctcttcta tgtcaaataa taccagtgaa

 961 gatcaatctt atgatgctgt ggttgtcact gctccaattc gcaatgtcaa agaaatgaag

1021 attatgaaat ttggaaatcc attttcactt gactttattc cagaggtgac gtacgtaccc

1081 ctttccgtta tgattactgc attcaaaaag gataaagtga agagacctct tgagggcttc

1141 ggagttctta tcccctctaa agagcaacat aatggactga agactcttgg tactttattt

1201 tcctccatga tgtttcctga tcgtgctcca tctgacatgt gtctctttac tacatttgtc

1261 ggaggaagca gaaatagaaa acttgcaaac gcttcaacgg atgaattgaa gcaaatagtt

1321 tcttctgacc ttcagcagct gttgggcact gaggacgaac cttcatttgt caatcatctc

1381 ttttggagca acgcattccc attgtatgga cacaattacg attctgtttt gagagccata

1441 gacaagatgg aaaaggatct tcctggattt ttttatgcag gtaaccataa gggtggactt

1501 tcagtgggaa aagcgatggc ctccggatgc aaggctgcgg aacttgtaat atcctatctg

1561 gactctcata tatacgtgaa gatggatgag aagaccgcgt aa //
```

TABLE 14

*Amaranthus tuberculatus* biotype WCS (herbicide sensitive) mitochondrial protoporphyrinogen oxidase long form (PPX2L) gene, partial cds from genomic DNA; nuclear gene for mitochondrial product, corresponding to Accesssion DQ394875 and to SEQ ID NO:31 and NO:32. The protein coding region begins at 65 and continues beyond 4797, with coding sequence splicing as follows:

```
join(<65..185, 287..326, 516..651, 755..820, 1227..1277,
1399..1455, 2081..2157, 2646..2682, 2777..2842, 3374..>3414)
MVIQSITHLSPNLALPSPLSVSTKNYPVAVMGNISEREEPTSAKRVAVVGAGVSGLAAAYKLKSHGLSVT
LFEADSRAGGKLKTVKKDGFIWDEGANTMTESEAEVSSLIDDLGLREKQQLPISQNKRYIARDGLPVLLP
SNPAALLTSNILSAKSKLQIMLEPFLWRKHNATELSDEHVQESVGEFFERHFGKEFVDYVIDPFVAGTCG
GDPQSLSMHHTFPEVWNIEK
   1 aagaattgaa ttggcagatt gagacaaaat tggattcaga atttagcaaa tttaaaccga

  61 tcgtatggta attcaatcca ttacccacct ttcaccaaac cttgcattgc catcgccatt

 121 gtcagtttca accaagaact acccagtagc tgtaatgggc aacatttctg agcgggaaga

 181 acccagtaag tcaacctttc ttcacatatc ttaaagcaat cccttttcaa ctacactttc

 241 ttttgatgat ttcacattct gagttttttt tattggggat ttttagcttc tgctaaaagg

 301 gttgctgttg ttggtgctgg agttaggtaa attttatgtt tcttttccag aaagattgta

 361 aaattttgct ttgattgttc tgaattttga tgggtttttg cataatgatt tgtatttggg

 421 atgggcaaat ttttcagtag atcatactac ttttaacttc tattttctgt ataattttat

 481 tgatttccta aactgttttt gtggaattgt tctagtggac ttgctgctgc atataagcta

 541 aaatcccatg gtttaagtgt gacattgttt gaagctgatt ctagagctgg aggcaaactt

 601 aaaactgtta aaaaagatgg ttttatttgg gatgaggggg caaatactat ggtaatgttt

 661 atcaacaatg ctggttttct gatttagaac caattacttg ctggattttg ggtcaattct

 721 gtggttaaca tgtcactttc tgatatgctt gtagacagaa agtgaggcag aggtctcgag

 781 tttgatcgat gatcttgggc ttcgtgagaa gcaacagttg gtaagttttc tgtctaagcc
```

TABLE 14-continued

| *Amaranthus tuberculatus* biotype WCS (herbicide sensitive) mitochondrial protoporphyrinogen oxidase long form (PPX2L) gene, partial cds from genomic DNA; nuclear gene for mitochondrial product, corresponding to Accesssion DQ394875 and to SEQ ID NO:31 and NO:32. The protein coding region begins at 65 and continues beyond 4797, with coding sequence splicing as follows: |
|---|
| 841 cattcccttt gcttgctaga gtccgtagcg caaaaatacg gtaatagtca tgatcgtggt |
| 901 aatgacatgg tgatgcggtg acaggagtca tgtgatcgtt attccaacta taggtcaaaa |
| 961 acatgatatt ttccttgtga cgccccaaaa tgcagtattt ttacaccttt acattgcggg |
| 1021 gaaaaatagg tttattatgt tgaaaacctt tacaaggcgg ctgatgcgat gcggccttgt |
| 1081 ttttgcatta tgttcttgaa gcaacttatt atatctttga ttaatgtatc atcagcttaa |
| 1141 aacagcctta ttgtacttct taatctagtt ttgacttttg aggttgcttt tacaagatct |
| 1201 ttatatgatt ggttcttctg tcacagccaa tttcacaaaa taaaagatac atagctagag |
| 1261 acggtcttcc tgtgctagta agtcctctgc atttactttt gacctctatg aacttctaac |
| 1321 actggatact aagttgtatt cgaggcaaat tctgtatttt ccaatctgct tattgacagt |
| 1381 tgcttgcaaa ctttgcagct accttcaaat cccgctgcac tactcacgag caatatcctt |
| 1441 tcagcaaaat caaaggttat caatgctaaa atcatgtttg gtatttgatt acttagcttt |
| 1501 tggtgtatgc aataatttgg tttctaaaac taagtgattg acggaaaagg agggacgaag |
| 1561 gacatagaat tgcaattttg tgttcttcat gtatttttac ttttagagta ggtaagtcac |
| 1621 tttcggtccg tttggttaat ggtactagtt ggtggtaata ggaatgattt gtagtgtaaa |
| 1681 ttttcaagat atatatcatg tcattcccat ggtaatgaaa gtttgatcat aaaaaggttt |
| 1741 tttgttcaca attttccatt accacctaat accacatgtt taaatggtaa tgcattggaa |
| 1801 tgagttttgt gaagaaaatg agtttgttga gaaagaataa gcatggtcat taaatttgtc |
| 1861 aagagatatt cctatcaaaa ttacactagc tttccattat catttcacca tttagtaccg |
| 1921 attaccaaat gggccgttta tagtttggga agagcatacg tttgtgtaaa acttttattt |
| 1981 tgaagttgaa agaatttgtt gcaccttttg ttatgattag gttttgatgt ttttagctgc |
| 2041 aataaatttg ttgatgaaaa agccactact tttttctcag ctgcaaatta tgttggaacc |
| 2101 atttctctgg agaaaacaca atgctactga actttctgat gagcatgttc aggaaaggca |
| 2161 agtgccacat actattaagt gttagttgct gagaatatat ttgaatctaa gatgcacgaa |
| 2221 gaccactggt gcccttgctc tatcaattct gatggaaagg attatcgctg aatttacctt |
| 2281 ctactaaaac atcgataaaa tacttcatta ttagcatcaa aagattccct ccatccttct |
| 2341 ggttttgcta gacttgcctt atgaaggtgt tcaaggagta gtttgctacc cttcaagata |
| 2401 gggtagtggt tgccgtctct cataatttca gtcactcgtt ttcctctcct aattcaagcc |
| 2461 ataattttta tggttcctcc acacaacact tgctaaattt gaaaagtagc aaagaggaag |
| 2521 tgagcaaaat cagcaggagt aggactgatg agtaagagct tgattaagtg tagaggattt |
| 2581 tcttttgtgt tgaatatgaa tgcatcatgc atgactgtag aattgacata atgatttgtc |
| 2641 tgcagcgttg gtgaattttt tgagcgacat tttgggaaag aggtattgtt gccaattgcc |
| 2701 atgctctatt cattccggtg aattaacaaa tgttgtgctt ctgcttacta ttgcttataa |
| 2761 ttattgtttg ttgcagtttg ttgattatgt tattgaccct tttgttgcgg gtacatgtgg |
| 2821 tggagatcct caatcgcttt ccgtgagtta aatactgtgc ttgctttttt ttttcaacat |
| 2881 tttctggagg ctgtaaataa attatactcc ttcctattct aatcaaatat cctatttccc |
| 2941 cttttggcat attcaaattt agttaaatat tgtgtaaatt atttacacaa ttgccattaa |

TABLE 14-continued

| Amaranthus tuberculatus biotype WCS (herbicide sensitive) mitochondrial protoporphyrinogen oxidase long form (PPX2L) gene, partial cds from genomic DNA; nuclear gene for mitochondrial product, corresponding to Accesssion DQ394875 and to SEQ ID NO:31 and NO:32. The protein coding region begins at 65 and continues beyond 4797, with coding sequence splicing as follows: |
|---|
| 3001 attttcactt ttcccttact cactcttctc atgtgtccct tccccctttt cttaaaattg |
| 3061 gtgcattatc aaataggaca tttgatttga ataggcggga gtttccaatt gtgcttccaa |
| 3121 aggtagcttg tcactttttc tttttcttta aattttgtac catgccatgc attttgaacc |
| 3181 tcaactcatt tcgccataaa ggaatattat gtttgagaag aacgaggata ctattatctt |
| 3241 atagataaca tataggtttc attatcaatg attgtttgat tttcaactct tcttttcctt |
| 3301 tcatgctcat attgatgtta tttctatttg ttatgaatta tgtccattgt gttaatgtct |
| 3361 ttctttattg tagatgcacc atacatttcc agaagtatgg aatattgaaa aaaggtatga |
| 3421 accttaaagc tttaattttc ttcgaactta atgtttctta attgattctt ttggatcaat |
| 3481 ttccataaga atggaaattt aaaaaaaggt atgaacctta aagatttctt cgaacttata |
| 3541 tgttttgtaa ttcatgcttt tagatgttgc accattttat ctatgtgtct taagtttgtt |
| 3601 gtaatcattt gtagaccaaa agaatgaatg gtctggtttg aaatggttca tcgtgcaaaa |
| 3661 atgcgatttt gcttgtgatt gaggtaacat tcaaggtgat gtgtttgtcg tactgtcaaa |
| 3721 tgtcttccta taccatatga tatatatata agcctaaaat gatatattgt atacctttag |
| 3781 gatgtggata gcaggggttc agtacatatg aaaaatcctt gcaatttgat ctgtacgata |
| 3841 caatgtgatt ttgccttttg ccttttgcct tttgttatat gatgatgatt ccatgtgaaa |
| 3901 ttttgggatt tagaaaattc acttgtttaa gaacatttga atcaaacttt caccaatttc |
| 3961 aaccacattt aattgcggca aagccgaact ttaaaagtca ctcccaatct ttgagatatc |
| 4021 caaactccaa aacttctatt agctttcatg ttttcactaa gtaaagttgg tgcgactcct |
| 4081 taccattttc tttattatgc atttcgttga tgtataatag tatagattgg tgctctcttc |
| 4141 gctctccttc caacatgcat aacttctagt tcttgtcgtt ttcttttcct ccctattttt |
| 4201 atttgacttg tagctatttt tgttcactct tctcgcccaa tccaaaactt gtagctaaag |
| 4261 aaacttgatt tcattgattt tgtaactgat atgcaattca tttttgtttg cttttagttg |
| 4321 ttgattcaaa aacaataatg ctaaagccct aatcctaaca tgtcgggtta gctgttgaaa |
| 4381 caatacttga aattgctata aaaagggatt tttttcgggt acttcagttg ttgagattga |
| 4441 tatggtcaag tataatttgt tttaacacaa tttgtaatga tttaatggct tagtttcata |
| 4501 gctgtttgta ttaataaagg aaggaggact atccgaaatt gcaataggaa agagatttta |
| 4561 gttcggtatt tggttgttta aattgatatg gccaagtaat gttcatttta cacaattggt |
| 4621 aatgttttat tggctcaata gtgtttgtaa gtatgcgact caaatttaat caagtataac |
| 4681 ttattgaaac ataaataaat atccattagg tttggctctg tgtttgctgg actaattcaa |
| 4741 tcaacattgt tatctaagaa ggaaaagggt ggagaaaatg cttcataaga agcctcg |

TABLE 15

| *Amaranthus tuberculatus* biotype ACR mitochondrial protoporphyrinogen oxidase long form (PPX2L) gene with partial cds; nuclear gene for mitochondrial product, corresponding to NCBI Accession DQ394876 and SEQ ID NO:33 (DNA) and NO:34 (amino acid). Splicing is as follows for mRNA: |
|---|
| join (<65..185, 287..326, 516..651, 755..820, 1227..1277, 1399..1455, 2080..2156, 2645..2681, 2776..2838, 3366..>3406) |
| CDS join (65..185, 287..326, 516..651, 755..820, 1227..1277, 1399..1455, 2080..2156, 2645..2681, 2776..2838, 3366..>3406) |
| MVIQSITHLSPNLALPSPLSVSTKNYPVAVMGNISEREEPTSAKRVAVVGAGVSGLAAAYKLKSHGLSVTLFEADSRAGGKLKTVKKDGFIWDEGANTMTESEAEVSSLIDDLGLREKQQLPISQNKRYIARDGLPVLLPSNPAALLTSNILSAKSKLQIMLEPFLWRKHNATELSDEHVQESVGEFFERHFGKEFVDYVIDPFVAGTCGDPQSLSMHHTFPEVWNIEK |
| 1 aagaattgaa ttggcagatt gagacaaaat tggattcaga atttagcaaa tttaaaccga |
| 61 tcgtatggta attcaatcca ttacccacct ttcaccaaac cttgcattgc catcgccatt |
| 121 gtcagtttcc accaagaact acccagtagc tgtaatgggc aacatttctg agcgagaaga |
| 181 acccagtaag tcaacctttc ttcacatatc ttaaagcaat cccttttcaa ctacactttc |
| 241 ttttgatgat ttcacattct gagttttttt tattggggat ttttagcttc tgctaaaagg |
| 301 gttgctgttg ttggtgctgg agttaggtaa attttatgtt tcttttccag aaagattgta |
| 361 aaatttttgct ttgattgttc tgaattttga tgggtttttg cataatgatt tgtatttggg |
| 421 atgggcaaat ttttcagtag atcatactac ttttaacttc tattttctgt ataattttat |
| 481 tgatttccta aattgttttt gtggaattgt tctagtggac ttgctgctgc atataagcta |
| 541 aaatcccatg gtttgagtgt gacattgttt gaagctgatt ctagagctgg aggcaaactt |
| 601 aaaactgtta aaaaagatgg ttttatttgg gatgaggggg caaatactat ggtaatgttt |
| 661 atcaacaatg ctggttttct gatttagaac caattacttg ctggattttg ggtcaattct |
| 721 gtggttaaca tgtcactttc tgatatgctt gtagacagaa agtgaggcag aggtctcgag |
| 781 tttgatcgat gatcttgggc ttcgtgagaa gcaacagttg gtaagttttc tgtctaagcc |
| 841 cattcccttt gcttgctaga gtccgtagcg caaaaaatacg gtaatagtca tgatcgtggt |
| 901 aatgacatgg tgatgcggtg acaggagtca tgtgatcgtt attccaacta taggtcaaaa |
| 961 acatgatatt ttccttgtga cgccccaaaa tgcggtattt ttacaccttt acattgcggg |
| 1021 gaaaaatagg tttattatgt tgaaaacctt tacaaggcgg ctgatgcgat gcggccttgt |
| 1081 ttttgcatta tgttctagaa gcaacttatt atatctttga ttaatgtatc atcagcttaa |
| 1141 aacagcctta ttgtacttct taatctagtt ttgacttttg aggttgcttt tacaagatct |
| 1201 ttatatgatt ggttcttctg tcacagccaa tttcacaaaa taaaagatac atagctagag |
| 1261 acggtcttcc tgtgctagta agtcctctgc atttactttt gacctctatg aacttctaac |
| 1321 actggatact aagttgtatt cgaggcaaat tctgtatttt ccaatctgct tattgacagt |
| 1381 tgcttgcata ctttgcagct accttcaaat cccgctgcac tactcacgag caatatcctt |
| 1441 tcagcaaaat caaaggttat caatgctaaa atcatgtttg gtatttgatt acttagcttt |
| 1501 tggtgtatgc aataatttgg tttctaaaac taagtgattg acggaaaagg agggacgaag |
| 1561 gacatagaat tgcaattttg tgttcttcat gtatttttac ttttagagta ggtaagtcac |
| 1621 tttcggtccg tttggttaat ggtactagtt ggtggtaata ggaatgattt gtagtgtaaa |
| 1681 ttttcaagat atatatcatg tcattcccat ggtaatgaaa gtttgatcat aaaaaggttt |
| 1741 tttgttcaca attttccatt accacctaat accacatgtt taaatggtaa tgcattggaa |
| 1801 tgagttttgt gaagaaaatg agtttgttga gaaagaataa gcatggtcat taaatttgtc |
| 1861 aagagatatt cctatcaaaa ttacactagc tttccattat catttcacca tttagtaccg |
| 1921 attaccaaat gggccgttta tagtttggga agagcatacg tttgtgtaaa acttttattt |

TABLE 15-continued

| |
|---|
| *Amaranthus tuberculatus* biotype ACR mitochondrial protoporphyrinogen oxidase long form (PPX2L) gene with partial cds; nuclear gene for mitochondrial product, corresponding to NCBI Accession DQ394876 and SEQ ID NO:33 (DNA) and NO:34 (amino acid). Splicing is as follows for mRNA: |

1981 tgaagttgaa agaatttgtt gcaccttttg ttatgattaa gttttgatgt ttttagctgc 2041 aataatttgt tgatgaaaaa gccactactt ttttctcagc tgcaaattat gttggaacca 2101 tttctctgga gaaaacacaa tgctactgaa ctttctgatg agcatgttca ggaaaggcaa 2161 gtgccacata ctattaagtg ttagttgctg agaatatatt tgaatctaag atgcacgaag 2221 accactggtg cccttgctct atcaattctg atggaaagga ttatcgctga atttaccttc 2281 tactaaaaca tcgataaaat acttcattat tagcatcaaa agattccctc catccttctg 2341 gttttgctag acttgcctta tgaaggtgtt caaggagtag tttgctaccc ttcaagatag 2401 ggtagtggtt gccgtctctc ataatttcag tcactcgttt tcctctccta attcaagcca 2461 taatttttat ggttcctcca cacaacactt gctaaatttg aaaagtagca aagaggaagt 2521 gagcaaaatc agcaggagta ggactgatga gtaagagctt gattaagtgt agaggatttt 2581 cttttgtgtt gaatatgaat gcatcatgca tgactgtaga attgacataa tgatttgtct 2641 gcagcgttgg tgaatttttt gagcgacatt ttgggaaaga ggtattgttg ccaattgcca 2701 tgctctattc attccggtga attaacaaat gttgtgcttc tgcttactat tgcttataat 2761 tattgtttgt tgcagtttgt tgattatgtt attgaccctt ttgttgcggg tacatgtgga 2821 gatcctcaat cgctttccgt gagttaaata ctgtgcttgc tttttttttt caacattttc 2881 tggaggctgt aaataaatta tactccttcc tattctaatc aaatatccta tttccccttt 2941 tggcatattc aaatttagtt aaatattgtg taaattattt acacaattgc cattaaattt 3001 tcacttttcc cttactcttc tcatgtgtcc cttccccctt ttcttaaaat tggtgcatta 3061 tcaaatagga catttgattt gaataggcgg gagtttccaa ttgtgcttcc aaaggtagct 3121 tgtcactttt tctttttctt taaattttgt accatgccat gcattttgaa cctcaactca 3181 tttcgccata aaggaatatt atgtttgaga agaacgagga tactattatc ttatagataa 3241 catataggtt tcattatcaa tgattgtttg attttcaact cttcttttcc tttcatgctc 3301 atattgatgt tatttctatt tgttatgaat tatgtccatt gtgttaatgt ctttctttat 3361 tgtagatgca ccatacattt ccagaagtat ggaatattga aaaaaggtat gaaccttaaa 3421 gctttaattt tcttcgaact taatgtttct taattgattc ttttggatca atttccataa 3481 gaatggaaat ttaaaaaagg gtatgaacct taaagatttc ttcgaactta tatgttttgt 3541 aattcatgct tttagatgct gcaccatttt atctatgtgt cttaagtttg ttgtaatcat 3601 ttgtagacca aaagaatgaa tggtctggtt tgaaatggtt catcgtgcaa aaatgcgatt 3661 ttgcttgtga ttgaggtaac attcaaggtg gtgtgtttgt cgtactgtca aatgtcttcc 3721 tataccatgt gatatatata agcctaaaat gatatattgt acacctttag gatgtggata 3781 gcaggggttc agtacatatg aaaaatcctt gcaatttgat ctgtacgatc aatgtgattt 3841 tgccttttgc cttttgcctt ttgttatatg atgatgattc catgtgaaat tttgggattt 3901 agaaaattca cttgtttaag aacatttgaa tcaaactttc accaatttca accacattta 3961 attgcggcaa agccgaactt taaaagtcac tcccaatctt tgagatatcc aaactccaaa 4021 acttctatta gctttcatgt tttcactaag taaagttggt gcgactcctt accattttct 4081 ttattatgca tttcgttgat gtataatagt atagattggt gctctcttcg ctctccttcc TABLE 15-continued

*Amaranthus tuberculatus* biotype ACR mitochondrial protoporphyrinogen oxidase long form (PPX2L) gene with partial cds; nuclear gene for mitochondrial product, corresponding to NCBI Accession DQ394876 and SEQ ID NO:33 (DNA) and NO:34 (amino acid). Splicing is as follows for mRNA:

```
4141 aacatgcata acttctagtt cttgtcgttt tcttttcctc cctattttta tttgacttgt

4201 agctattttt gttcactctt ctcgcccaat ccatagctaa agaaacttga tttcattgat

4261 tttgtaactg atatgcaatt catttttgtt tgcttttagt tgttgattca aaaacaataa

4321 tgctaaagcc ctaatcctaa catgtcgggt tagctgttga aacaatactt gaaattgcta

4381 taaaaaggga ttttttttcgg gtacttcagt tgttgagatt gatatggtca agtataattt

4441 gttttaacac aatttgtaat gatttaatgg cttagtttca tagctgtttg tattaataaa

4501 ggaaggagga ctatctgaaa ttgcaatagg aaagagattt tagttcggta tttggttgtt

4561 taaattgata tggccaagta atgttcattt tacacaattg gtaatgtttt attggctcaa

4621 tagtgtttgt aagtatgcga ctcaaattta atcaagtata acttattgaa acataaataa

4681 atatccatta ggtttggctc tgtgtttgct ggactaattc aatcaacatt gttatctaag

4741 aaggaaaagg gtggagaaaa tgcttcataa gaagcctcgg acgtc
```

TABLE 16

Coding Squence of Chimeric Herbicide resistant PPXL2 Used in Arabidopsis Transformation Experiments (MTX_SRS; SEQ ID NO:45; encodes protein of SEQ ID NO:14 which is identical to SEQ ID NO:46)

```
ATGGTAATTCAATCCATTACCCACCTTTCACCAAACCTTGCATTGCCATC
GCCATTGTCAGTTTCAACCAAGAACTACCCAGTAGCTGTAATGGGCAACA
TTTCTGAGCGGGAAGAACCCACTTCTGCTAAAAGGGTTGCTGTTGTTGGT
GCTGGAGTTAGTGGACTTGCTGCTGCATATAAGCTAAAATCCCATGGTTT
GAGTGTGACATTGTTTGAAGCTGATTCTAGAGCTGGAGGCAAACTTAAAA
CTGTTAAAAAAGATGGTTTTATTTGGGATGAGGGGGCAAATACTATGACA
GAAAGTGAGGCAGAGGTCTCGAGTTTGATCGATGATCTTGGGCTTCGTGA
GAAGCAACAGTTGCCAATTTCACAAAATAAAAGATACATAGCTAGAGACG
GTCTTCCTGTGCTACTACCTTCAAATCCCGCTGCACTACTCACGAGCAAT
ATCCTTTCAGCAAAATCAAAGCTGCAAATTATGTTGGAACCATTTCTCTG
GAGAAAACACAATGCTACTGAACTTTCTGATGAGCATGTTCAGGAAAGCG
TTGGTGAATTTTTTGAGCGACATTTTGGGAAAGAGTTTGTTGATTATGTT
ATTGACCCTTTTGTTGCGGGTACATGTGGAGATCCTCAATCGCTTTCCAT
GCACCATACATTTCCAGAAGTATGGAATATTGAAAAAAGGTTTGGCTCTG
TGTTTGCTGGACTAATTCAATCAACATTGTTATCTAAGAAGGAAAAGGGT
GGAGAAAATGCTTCTATTAAGAAGCCTCGTGTACGTGGTTCATTTTCATT
TCAAGGTGGAATGCAGACACTTGTTGACACAATGTGCAAACAGCTTGGTG
AAGATGAACTCAAACTCCAGTGTGAGGTGCTGTCCTTGTCATATAACCAG
AAGGGGATCCCCTCATTAGGGAATTGGTCAGTCTCTTCTATGTCAAATAA
TACCAGTGAAGATCAATCTTATGATGCTGTGGTTGTCACTGCTCCAATTC
GCAATGTCAAAGAAATGAAGATTATGAAATTTGGAAATCCATTTTCACTT
GACTTTATTCCAGAGGTGACGTACGTACCCCTTTCCGTTATGATTACTGC
ATTCAAAAAGGATAAAGTGAAGAGACCTCTTGAGGGCTTCGGAGTTCTTA
TCCCCTCTAAAGAGCAACATAATGGACTGAAGACTCTTGGTACTTTATTT
TCCTCCATGATGTTTCCTGATCGTGCTCCATCTGACATGTGTCTCTTTAC
TACATTTGTCGGAGGAAGCAGAAATAGAAAACTTGCAAACGCTTCAACGG
ATGAATTGAAGCAAATAGTTTCTTCTGACCTTCAGCAGCTGTTGGGCACT
GAGGACGAACCTTCATTTGTCAATCATCTCTTTTGGAGCAACGCATTCCC
ATTGTATGGACACAATTACGATTCTGTTTTGAGAGCCATAGACAAGATGG
AAAAGGATCTTCCTGGATTTTTTTATGCAGGTAACCATAAGGGTGGACTT
TCAGTGGGAAAAGCGATGGCCTCCGGATGCAAGGCTGCGGAACTTGTAAT
ATCCTATCTGGACTCTCATATATACGTGAAGATGGATGAGAAGACCGCGT
AA
```

TABLE 17

Coding Sequence for herbicide sensitive PPX2L used in certain experiments (SEQ ID NO:47; encodes protein of SEQ ID NO:48)

```
ATGGTAATTCAATCCATTACCCACCTTTCACCAAACCTTGCATTGCCATC
GCCATTGTCAGTTTCAACCAAGAACTACCCAGTAGCTGTAATGGGCAACA
TTTCTGAGCGGGAAGAACCCACTTCTGCTAAAAGGGTTGCTGTTGTTGGT
GCTGGAGTTAGTGGACTTGCTGCTGCATATAAGCTAAAATCCCATGGTTT
GAGTGTGACATTGTTTGAAGCTGATTCTAGAGCTGGAGGCAAACTTAAAA
CTGTTAAAAAAGATGGTTTTATTTGGGATGAGGGGGCAAATACTATGACA
GAAAGTGAGGCAGAGGTCTCGAGTTTGATCGATGATCTTGGGCTTCGTGA
GAAGCAACAGTTGCCAATTTCACAAAATAAAAGATACATAGCTAGAGACG
GTCTTCCTGTGCTACTACCTTCAAATCCCGCTGCACTACTCACGAGCAAT
ATCCTTTCAGCAAAATCAAAGCTGCAAATTATGTTGGAACCATTTCTCTG
GAGAAAACACAATGCTACTGAACTTTCTGATGAGCATGTTCAGGAAAGCG
TTGGTGAATTTTTTGAGCGACATTTTGGGAAAGAGTTTGTTGATTATGTT
ATCGACCCTTTTGTTGCGGGTACATGTGGTGGAGATCCTCGATCGCTTTC
CATGCACCATACATTTCCAGAAGTATGGAATATTGAAAAAAGGTTTGGCT
CTGTGTTTGCTGGACTAATTCAATCAACATTGTTATCTAAGAAGGAAAAG
GGTGGAGAAAATGCTTCTATTAAGAAGCCTCGTGTACGTGGTTCATTTTC
ATTTCAAGGTGGAATGCAGACACTTGTTGACACAATGTGCAAACAGCTTG
GTGAAGATGAACTCAAACTCCAGTGTGAGGTGCTGTCCTTGTCATATAAC
CAGAAGGGGATCCCCTCATTAGGGAATTGGTCAGTCTCTTCTATGTCAAA
TAATACCAGTGAAGATCAATCTTATGATGCTGTGGTTGTCACTGCTCCAA
TTCGCAATGTCAAAGAAATGAAGATTATGAAATTTGGAAATCCATTTTCA
CTTGACTTTATTCCAGAGGTGACGTACGTACCCCTTTCCGTTATGATTAC
TGCATTCAAAAAGGATAAAGTGAAGAGACCTCTTGAGGGCTTCGGAGTTC
TTATCCCCTCTAAAGAGCAACATAATGGACTGAAGACTCTTGGTACTTTA
TTTTCCTCCATGATGTTTCCTGATCGTGCTCCATCTGACATGTGTCTCTT
TACTACATTTGTCGGAGGAAGCAGAAATAGAAAACTTGCAAACGCTTCAA
CGGATGAATTGAAGCAAATAGTTTCTTCTGACCTTCAGCAGCTGTTGGGC
ACTGAGGACGAACCTTCATTTGTCAATCATCTCTTTTGGAGCAACGCATT
CCCATTGTATGGACACAATTACGATTCTGTTTTGAGAGCCATAGACAAGA
TGGAAAAGGATCTTCCTGGATTTTTTTATGCAGGTAACCATAAGGGTGGA
CTTTCAGTGGGAAAAGCGATGGCCTCCGGATGCAAGGCTGCGGAACTTGT
AATATCCTATCTGGACTCTCATATATACGTGAAGATGGATGAGAAGACCG
CGTAA
```

DISCUSSION

While PPO inhibitor-resistant plants have been generated through genetic engineering approaches (Choi, 1998; Lee, 2000; Lermontova. 2000; Ha, 2004; Jung, 2004; Lee, 2004; Li, 2005), *A. tuberculatus* populations have developed resistance from the repeated use of these herbicides in agronomic production systems. The consequence of *A. tuberculatus* evolving resistance to PPO inhibitors, combined with its already widespread resistance to ALS-inhibiting herbicides, is that the only remaining chemical option for its control following emergence in *Glycine max* (soybean) production systems is glyphosate, which requires the planting of glyphosate-resistant varieties (Patzoldt, 2005). Although the molecular mechanisms of evolved resistance to many herbicides have been identified, such has not yet been elucidated for resistance to PPO inhibitors.

Seven different mechanisms of PPO inhibitor resistance have been proposed for plants (Dayan, 1997). Two of these mechanisms include either enhanced metabolic degradation of the herbicide or an alteration of the herbicide target site, which together constitute the majority of mechanisms for herbicide resistance in weed species. Of these, an altered herbicide target enzyme (PPO) was investigated based on previous characterization of R *A. tuberculatus* plants (Patzoldt, 2004). It was later determined in an independently identified PPO inhibitor-resistant *A. tuberculatus* population that enhanced metabolism was not responsible for resistance (Shoup, 2005).

The mechanism of PPO inhibitor resistance that was selected within natural populations of *A. tuberculatus* populations was a codon deletion in a gene encoding PPO. While alterations of herbicide target proteins are common mechanisms for conferring resistance, several characteristics about this specific mechanism merit highlighting. First, PPO inhibitors have two herbicide target sites in plants; i.e., in plastids and mitochondria (Jacobs, 1984); therefore, in order for target-site resistance to occur, two altered genes would need to be selected. However, *A. tuberculatus* plants have overcome this obstacle via mutation in a single gene (PPX2L) that encodes both plastidic and mitochondrial PPO isoforms. Second, the specific alteration of PPO2L that confers resistance to PPO-inhibiting herbicides is an amino acid deletion resulting from a three-bp deletion in the genomic (coding) DNA. This is the first report of an amino acid deletion, rather than a substitution, in a herbicide target site being selected in a natural (field) population as a resistance mechanism. While intentional selection for resistance to PPO inhibitors identified amino acid substitutions that conferred resistance (Li, 2005; U.S. Pat. No. 5,939,602), the codon-deletion approach revealed by *A. tuberculatus* is instructive of an alternative approach to achieve resistance. Third, the R biotype was found to be resistant to multiple chemical families of PPO inhibitors, albeit at different levels (Patzoldt, 2005), indicating that the ΔG210 mutation confers resistance to all PPO inhibitors. Finally, that R *A. tuberculatus* plants lacked one of the PPO genes (PPX2) found in plants from the S biotype is curious and requires further research. However, the absence of PPX2 in the R biotype likely is not related to the resistance phenotype since resistance was (incompletely) dominant and exhibited single-locus inheritance, PPX2L co-segregated with resistance, and the ΔG210 mutation was sufficient to confer lactofen insensitivity.

While the origin of the G210 codon deletion of PPX2L identified in the R *A. tuberculatus* biotype is uncertain, nucleotide length polymorphisms are not uncommon in this plant species. Codon insertion/deletions (indels) among populations of *A. tuberculatus* were previously identified in other genes encoding herbicide target proteins, e.g., ALS, and EPSPS (5-enolpyruvylshikimate-3-phosphate synthase. Furthermore, other indels, in addition to the G210 indel, were found among PPX genes in this study. In PPX1 (see SEQ ID NOs:13 and 14 and SEQ ID N019 and 20 and GenBank accessions DQ386112 and DQ386115), there were two additional, adjacent proline codons in the nucleotide sequence from R plants relative to S plants. An indel was also identified when PPX2 was compared with PPX2L from S plants (See SEQ ID NOs: 19-20 and 21-22; NCBI Accessions DQ386113 and DQ386114). As observed for the G210 polymorphism between R and S PPX2Ls, this also resulted in a glycine amino acid indel, but was located at a different position (128 nucleotides downstream of the G210 codon). The codon indels observed in *A. tuberculatus* typically are associated with short, simple sequence repeats (SSRs). The G210 indel in PPX2L is part of a bi-GTG repeat (or a bi-TGG repeat), the PPX21PPX2L indel is part of a tri-GGA repeat, and the PPX1 indel is part of a hexa-CCT repeat. SSRs are recognized as a means to provide adaptive genetic variation for evolutionary processes because of their high mutability (Kashi, 2006). Although the numbers of repeats associated with some of the PPX indels are fewer than typically recognized for SSRs that the indels are found within repeated nucleotides suggests a means for their evolutionary origin.

In regards to PPO inhibitor-resistant *A. tuberculatus* in agro-ecosystems, resistance can be transmitted maternally and paternally, and therefore is able to spread through seed dispersal or, more rapidly, via wind dispersal of pollen. Since *A. tuberculatus* is a dioecious plant, it is forced to outcross. This obligate outcrossing, combined with a significant level of resistance that is expressed in the heterozygous state (FIG. 2), will make pollen a very effective means for dissemination of the resistance. In addition to dissemination from a single "source" population, resistance to PPO inhibitors could become more widespread in *A. tuberculatus* populations by independent selection events. In fact, it seems likely that this already has occurred given the distinct locations where PPO inhibitor-resistant populations have been identified (Shoup, 2003; Li, 2004; Patzoldt, 2005), and the different PPX2L alleles containing the ΔG210 mutation identified in this study (FIG. 7).

*A. tuberculatus* is one of the most problematic weeds in agronomic fields throughout the Midwestern United States. In particular, the propensity of *A. tuberculatus* to rapidly evolve herbicide resistance makes its management difficult (Patzoldt, 2004). The herbicide resistance mechanism reported herein illustrates the sophisticated means by which it can adapt and evolve in response to weed control efforts. With the loss of PPO inhibitors as an effective *A. tuberculatus* management tool in soybean, farmers will become even more reliant on glyphosate.

In summary, an altered herbicide target site confers PPO inhibitor resistance in the R biotype. Several unique characteristics about this herbicide resistance mechanism deserve mention. First, PPO inhibitors have two herbicide target sites in plants (i.e. plastids and mitochondria (Jacobs and Jacobs, 1984); therefore, in order for target-site resistance to occur, two altered genes would need to be selected. Without wishing to be bound by theory, the inventors believe that plants from the R waterhemp biotype have overcome this obstacle with natural selection of a mutation in a single gene (PPX2L) that encodes two proteins that theoretically function in both plastids and mitochondria. Second, the specific alteration of PPO2 that confers resistance to PPO-inhibiting herbicides is an amino acid deletion rather than a substitution, unlike prior art mutations (see, e.g., U.S. Pat. Nos. 6,282,837; 5,939,602; and 6,808,904). Substitution mutations, in addition to the Gly deletion, have been observed in naturally resistant waterhemp.

The examples provided herein are for illustrative purposes and are not intended to limit the scope of the invention as claimed. Any variations in the exemplified compositions, plants and methods which occur to the skilled artisan are intended to fall within the scope of the present invention.

EXAMPLES

Detailed procedures for generation and analysis of *A. tuberculatus* lines, herbicide dose-response, and calculation of degree of dominance experiments and certain other procedures follow.

Example 1

*A. tuberculatus* Biotypes

The R biotype used in this study was derived from an *A. tuberculatus* (waterhemp) population originally collected in Adams County, Ill., and confirmed resistant to PPO-, ALS-, and photosystem II-inhibiting herbicides (Patzoldt, 2005). The S biotype was collected in Wayne County, Ill., and was identified in previous experiments to be susceptible to all herbicides tested (Patzoldt, 2002). *A. tuberculatus* plants derived from the original Adams County population that were PPO inhibitor-susceptible (S-BioAC), and those from a PPO inhibitor-resistant biotype collected in Clinton County, Ill. (R-BioCC), were utilized for sequencing of PPX2L alleles only.

Example 2

Plant Culture

*A. tuberculatus* seeds for each experiment were sown in flats (surface area of 930 $cm^2$) containing a 1:1:1 mixture of soil:peat:sand. Seedlings for each experiment were transplanted when needed into 12-cm square pots containing 800 ml of soil plus 0.2% (by vol) 14-14-14 Nutricote (Agrivert Inc., Glenpool, Okla.) when they were approximately 1-cm in height. Plants were grown in a greenhouse maintained at 28/22° C. day/night with supplemental light (minimum of 800 $\mu mol\ m^{-2}\ s^{-1}$ photon flux at the plant canopy) provided by mercury halide and sodium vapor lamps programmed for a 16-hour photoperiod.

Example 3

Herbicide Applications

Herbicide treatments were applied using a compressed air, moving nozzle laboratory sprayer equipped with an 80° flat fan nozzle (Teejet, Spraying Systems Co, Wheaton, Ill.) delivering 187 L $ha^{-1}$ of water at 207 kPa. The nozzle was maintained approximately 45 cm above the plant canopy. Plants were returned to the greenhouse immediately after herbicide treatment. All foliar-applied herbicide treatments were made when *A. tuberculatus* plants were 10-12 cm in height.

Example 4

Generation of $F_1$, $F_2$, and BC Lines

To create $F_1$ lines, *A. tuberculatus* plants from the R biotype were crossed with plants from the S biotype. Plants from the R biotype were confirmed herbicide-resistant by treatment with a herbicide mixture containing lactofen at 175 g active ingredient (ai) $ha^{-1}$, imazamox at 44 g acid equivalent (ae) $ha^{-1}$, and atrazine at 1000 g ai $ha^{-1}$, a PPO, acetolactate synthase (ALS), and photosystems II (PSII) inhibitor, respectively, plus 1% (by vol) crop oil concentrate (COC; Herbimax, Loveland Industries) and 2.5% (by vol) ammonium sulfate (AMS; Agriliance, St. Paul, Minn.). $F_1$ lines were created where the maternal parent was either S $\{F_1(S)\}$ or R $\{F_1(R)\}$. Following maturity, seeds were harvested from each female individually as full-sib lines. $F_1$ male plants were crossed with female plants from the S biotype, R biotype, or $F_1$ full-sibs to create $BC_S$, $BC_R$, or $F_2$ lines, respectively. Separate crosses were conducted using males from $F_1(S)$ or $F_1(R)$ lines. All F1 plants used for crossing were confirmed herbicide-resistant by treating with a mixture of lactofen, imazamox and atrazine as described herein. Each genetic combination was conducted twice with new *A. tuberculatus* plants, thus constituting a complete replication of the experiment. Crosses were conducted in growth chambers maintained at 28/22° C. day/night with fluorescent and incandescent bulbs providing 400 $\mu mol\ m^{-2}\ s^{-1}$ photon flux at the plant canopy programmed for a 16-hour photoperiod.

Example 5

Evaluation of $F_2$ and BC Lines

To confirm that $F_1$ lines were uniform in response, *A. tuberculatus* plants from $F_1(S)$, $F_1(R)$, R-parent, or S-parent lines were treated with lactofen at 110 g ai $ha^{-1}$ plus 1% (by vol) COC when they were 10-12 cm in height. Plants were qualitatively assessed 15 days after treatment as either R or S, followed by removal of above-ground tissue, drying at 65° C. for at least three days, and weighing to obtain dry mass measurements. *A. tuberculatus* lines were evaluated in a completely randomized design with 100 replications (plants) per line. Dry weight measurements of lactofen-treated plants were compared with control plants from the same line that received an application of 1% (by vol) COC only. Data from $F_1$ lines were compared to the parental biotypes and analyzed using PROC GLM in SAS (SAS Systems Inc.) using single degree of freedom contrast statements.

When analyzed, the R parent and both $F_1$ lines were significantly different from the S-parent in their response to lactofen at 110 g ai $ha^{-1}$ ($P<0.0001$). Furthermore, both $F_1(S)$ and $F_1(R)$ lines were significantly different from the R-parent ($P=0.0009$ or $P=0.0008$, respectively), but were not different from one another ($P=0.9790$). Even though $F_1$ lines were significantly different from the R-parent when comparing mean responses, individual heterozygous plants could not be distinguished from homozygous R plants due to their wide overlap of responses (FIG. A6). These results demonstrated that treatments with lactofen at 110 g ai $ha^{-1}$ plus 1% (by vol) COC were able to distinguish lactofen-susceptible plants based on dry weights, and were useful for determining the inheritance of PPO inhibitor resistance in $F_2$ and backcrossed (BC) lines.

Inheritance of PPO inhibitor resistance was determined by evaluating R or S responses of plants from $F_2$ and BC lines 15 days after treatment with lactofen at 110 g ai $ha^{-1}$ plus 1% (by vol) COC. From each $F_2$ or BC line, 50 plants from each cross (including replicated crosses) were assessed in a completely randomized design. The entire experiment was conducted twice, with a total of 100 plants assessed from each cross. Responses of each cross were subjected to Chi-square analysis to determine if responses were due to the inheritance of a single genetic unit of inheritance. No differences were observed among replications of the same cross; therefore, data obtained from similar crosses were combined.

Alternatively, waterhemp plants from $F_1$(S), $F_1$(R), R-parent, or S-parent lines were treated with lactofen at 110 g ai $ha^{-1}$ plus 1% (by vol) COC when they reached 10-12 cm in height. Plants were qualitatively assessed 15 days after treatment as either R or S, followed by removal of above-ground tissue, drying at 65° C. for at least three days, and weighing to obtain dry mass measurements. Waterhemp lines were evaluated in a completely randomized design with 100 replications (plants) per line. Dry weight measurements of lactofen-treated plants were compared with control plants from the same line that received an application of 1% (by vol) COC only. Data from $F_1$ lines were compared to the parental biotypes and analyzed using PROC GLM in SAS software (SAS Institute, Cary, N.C.) using single degree of freedom contrast statements.

Example 6

Calculation of Degree of Dominance

*A. tuberculatus* plants from the $F_1$(S) or $F_1$(R) lines, including plants from the S or R parental biotypes, were treated with various rates of lactofen or acifluorfen to calculate dominance of PPO inhibitor resistance. Herbicides were applied at rates incrementally spaced along a base 10 logarithmic scale. Herbicide rates for acifluorfen and lactofen for each *A. tuberculatus* line were: 0.00022 to 220 g ai $ha^{-1}$ for the S-parent; 0.00022 to 22000 g ai $ha^{-1}$ for $F_1$s; and 0.0022 to 22000 g ai $ha^{-1}$ for the R-parent.

Herbicide treatment dispersions with acifluorfen or lactofen included 1% (by vol) COC. Herbicide dose-response experiments were conducted using a completely randomized design with six replications per treatment. Both sets of $F_1$s (including reciprocals) were used in dose-response experiments, thus constituting a complete replication. Above-ground tissue from all herbicide dose-response experiments with acifluorfen was harvested 10 days after treatment (DAT), while tissue treated with lactofen was harvested either 10 or 15 DAT. Plant material was dried at 65° C. for at least three days, and dry weights recorded. SAS was used to analyze differences between experimental runs using PROC GLM, and $GR_{50}$ (growth reduction by 50%) estimates were calculated using PROC NLIN using percent dry weight values compared with control plants (Seefeldt et al. 1995). Control plants from each *A. tuberculatus* line received a treatment solution containing 1% (by vol) COC only. The degree of dominance (D) for PPO inhibitor resistance was calculated using the formula $D=(2W_3-W_2-W_1)/(W_2-W_1)$, where $W_1=\log(GR_{50})$ of the S-parent, $W_2=\log(GR_{50})$ of the R-parent, and $W_3=\log(GR_{50})$ of the $F_1$(S) or $F_1$(R) lines (0 to 1=dominant; 0=partially dominant; 0 to −1=recessive) (Stone, 1968).

Waterhemp plants from the $F_1$(S) or $F_1$(R) lines, plus plants from the S or R parents, were treated with lactofen or acifluorfen when they reached 10 to 12 cm in height. Herbicides were applied at rates incrementally spaced along a base 10 logarithmic scale. Herbicide rates for acifluorfen and lactofen for each waterhemp line were: 0.00022 to 220 g ai $ha^{-1}$ for the S-parent; 0.00022 to 22000 g ai $ha^{-1}$ for $F_1$s; and 0.0022 to 22000 g ai $ha^{-1}$ for the R-parent. Herbicide treatment dispersions with acifluorfen or lactofen included 1.0% (by vol) COC.

Herbicide dose-response experiments were conducted using a completely randomized design with six replications per treatment. Both sets of $F_1$s (including reciprocals) were used in dose-response experiments, thus constituting a complete replication. Above-ground tissue from all herbicide dose-response experiments with acifluorfen was harvested 10 days after treatment (DAT), while those treated with lactofen were harvested either 10 or 15 DAT. Plant material was dried at 65° C. for at least three days, and dry weights recorded. SAS (statistical software package, SAS Institute Inc., Cary, N.C.) was used to analyze differences between experimental runs using PROC GLM, and $GR_{50}$ (growth reduction by 50%) estimates were calculated using PROC NLIN as described by Seefeldt et al. (1995) using percent dry weight values compared with control plants. Control plants from each waterhemp line received a treatment solution containing 1% (by vol) COC only. The degree of dominance (D) for PPO inhibitor resistance was calculated using the formula $D=(2W_3-W_2-W_1)/(W_2-W_1)$, where $W_1=\log(GR_{50})$ of the S-parent, $W_2=\log(GR_{50})$ of the R-parent, and $W_3=\log(GR_{50})$ of the $F_1$(S) or $F_1$(R) lines (0 to 1=dominant; 0=partially dominant; 0 to −1=recessive) (Stone 1968).

Example 7 cDNA Sequencing

Total RNA was isolated using young leaf tissue from a single plant from each of the R and S biotype (McCarty, 1986), followed by purification of mRNA (Promega, Madison, Wis.). Upon sequencing PPX2 from the S biotype, two transcripts were identified of different length; these were designated as PPX2S or PPX2L for short or long forms, respectively.

Purified mRNA was used to obtain full-length sequences of PPX1 or PPX2 using 5' and 3' RACE (Rapid Amplification of cDNA Ends, Invitrogen, Carlsbad, Calif.). Primers were designed based on conserved regions of nucleotide sequences of PPX1 or PPX2 from numerous plant species (Che et al. 2000; Horikoshi et al. 1999; Johnston et al. 1998; Lermontova et al. 1997; Narita et al. 1996; Watanabe et al. 2001). Sequencing of the resultant fragments facilitated the design of gene-specific primers for *A. tuberculatus* PPX1 and PPX2 that were used to obtain their full-length sequences.

Total RNA was individually isolated from three *A. tuberculatus* plants each of the R or S biotypes, and used to create cDNA in reactions with reverse transcriptase (Invitrogen). PCR was used to amplify PPX1, PPX2, or PPX2L with the following primers: PPX1, forward 5'-gagagagtgcgagagagatgag-3' (SEQ ID NO:1) and reverse 5'-caagatgctggagccctattgac-3' (SEQ ID NO:2); PPX2, forward 5'-gccatcgccattgtcagtttac-3' (SEQ ID NO:3) and reverse 5'-gaattacgcggtcttctcatccat-3' (SEQ ID NO:4); PPX2L, forward 5'-gacaaaattggattcagaatttagc-3' (SEQ ID NO:5) and reverse 5'-gaattacgcggtcttctcatccat-3' (SEQ ID NO:6). PCRs contained 1 µl cDNA, 400 nM each of forward and reverse primers, 0.2 mM each of dATP, dCTP, dGTP, and dTTP, 1.5 mM $MgCl_2$, and 1.0 unit of High Fidelity Taq polymerase (Roche Molecular Biochemicals, Indianapolis, Ind.) with a 1× concentration of supplied buffer in a final volume of 25 µl. The reactions were subjected to a 3 min incubation at 95° C.; 35 cycles of 0.5 min at 95° C., 1 min at 58° C., and 1.5 min at 72° C.; then 5 min at 72° C. Resultant PCR products were isolated by gel electrophoresis, sequenced (Patzoldt, 2001), and compared using both Sequencher 4.1™ (Gene Codes Corporation, Ann Arbor, Mich.) and online software (described in Thompson et al. 1994. Nucl. Acids Res. 22:4673-4690). Sequences among plants from the same biotypes were similar: therefore, only a single sequence is presented for each gene/biotype combination.

Example 8

Southern Blot

Genomic DNA (gDNA) was isolated from young leaves of *A. tuberculatus* plants from the S or R biotypes (Ausubel, 1999). PPO inhibitor responses of each plant were confirmed by treatment with lactofen at 175 g ai $ha^{-1}$ plus 1% (by vol) COC. Samples were prepared by digesting 7.5 μg gDNA with 100 units of either EcoRI or HindIII to completion, followed by separation in a 1% (by wt) agarose gel, and then transferred to a nylon membrane (Roche Molecular Biochemicals, Indianapolis, Ind.). The membrane was probed with a DIG-labeled (Roche Molecular Biochemicals) PCR fragment of PPX2L amplified from gDNA isolated from a single S plant. Hybridization and probe detection were performed following the manufacturer's instructions.

Example 9

PCR-Based Molecular Markers

Inheritance of PPX1 and PPX2L alleles in BCs progeny was studied by treating plants with lactofen at 110 g ai $ha^{-1}$ plus 1% (by vol) COC when they were 10-12 cm in height. Prior to lactofen applications, tissue samples were obtained from each plant to isolate DNA (Doyle and Doyle, 1990). PCR-based molecular markers were used to identify the parental origin (R or S) of the PPX alleles contributed by the $F_1$ male to the BCs progeny.

To differentiate R or S PPX1 alleles, a fragment of genomic PPX1 was amplified via PCR using the forward primer, 5'-tgataagtcgctcaatggaga-3' (SEQ ID NO:7), and reverse primer 5'-agatttgtagcacctccaatg-3' (SEQ ID NO:8), followed by BspDI digestion to identify S alleles (i.e., S PPX1 alleles contain a recognition sequence for BspDI, while R alleles do not).

To identify parent-specific PPX2L alleles, a fragment of genomic PPX2L was amplified via PCR using the forward primer, 5'-aagagacctcttgagggcttc-3' (SEQ ID NO:9), and reverse primer 5'-gaattacgcggtcttctcatccat-3' (SEQ ID NO:10), followed by TfiI digestion to identify S alleles (i.e., S PPX2L alleles contain a recognition sequence for TfiI, while R alleles do not). PCRs contained 40 ng total DNA, 400 nM each of forward and reverse primers, 0.2 mM each of dATP, dCTP, dGTP, and dTTP, 2.0 mM $MgCl_2$, and 1 unit of Taq polymerase (Invitrogen) with a 1× concentration of supplied buffer in a final volume of 20 μl. The reactions were subjected to a 3 min incubation at 95° C.; 40 cycles of 0.5 min at 95° C., 1 min at 60° C. or 64° C. for reactions with PPX1 or PPX2L primers, respectively, and 1.5 min at 72° C.; then 5 min at 72° C. Following PCR amplification, a mixture containing 0.5 unit of the appropriate restriction enzyme with a 1× concentration of supplied buffer in a final volume of 10 μl was added to each reaction. Digests with BspDI were incubated at 37° C. for four hrs, while digests with TfiI were incubated at 65° C. for two hrs. PCR products were fractionated in a 1% (by wt) agarose gel containing 0.5 μg $ml^{-1}$ ethidium bromide and visualized with ultraviolet light.

Example 10

PPX2L Genomic DNA Sequencing gDNA was isolated from leaf tissue of S or R plants (37) to sequence a portion of genomic PPX2L. Primers were designed that flanked the G210 codon of PP02L, then subsequent sequencing of amplified fragments facilitated the design of new primers until the exon containing the G210 codon was identified. Primer sets (A-D), starting with the largest fragment, were (forward then reverse): A, 5'-gccatcgccattgtcagtttac-3' (SEQ ID NO:3) and 5'-ggagcagtgacaaccacagcatca-3' (SEQ ID NO:36); B, 5'-atcgatgatcttgggcttcgtg-3' (SEQ ID NO:37) and 5'-aatggtaaggagtcgcaccaac-3' (SEQ ID NO:38); C, 5'-cttcaaatcccgctgcacta-3' (SEQ ID NO:39) and 5'-tacttctggaaatgtatgg-3' (SEQ ID NO:40) and D, 5'-gagaaaacacaatgctactgaa-3' (SEQ ID NO:41) and 5'-acagcctccagaaaatgttg-3' (SEQ ID NO:42). PCR amplification, sequencing, and analysis were similar to the method used for cDNA sequencing of PPX genes.

Example 11

Functional Complementation

A shortened version of PPX2L from the S *A. tuberculatus* biotype was cloned into a PBAD-TOPO expression vector (Invitrogen) so that translation began at the second ATG start codon (+91). PPX2L cDNA was PCR-amplified using the forward primer 5'-caggaataagtaatgggcaacatttctgag-3' (SEQ ID NO:11) containing both a ribosome binding site (AGGA) and ATG start codon, and reverse primer 5'-gaagaattacgcggtcttctcatc-3' (SEQ ID NO:12) containing a stop codon. In order to create PPO inhibitor R and S plasmids that would encode proteins differing only in the presence/absence of G210, PPX2L was PCR-amplified from multiple cDNA samples and a region of the gene encompassing an approximately 500-bp XhoI/DraIII fragment was sequenced. The 3-bp polymorphism corresponding to the ΔG210 mutation was within this XhoI/DraIII fragment. Two XhoI/DraIII fragments were identified that were identical except for the presence/absence of the G210 codon and a C/T nucleotide polymorphism that was in the third position of a serine codon (and therefore did not alter the encoded protein). These two fragments were each used to replace the corresponding fragment in the pBAD-TOPO PPX2L construct. The region encompassing the replaced fragment was sequenced from the two resulting constructs to confirm the existence of the 3-bp polymorphism, and that no other polymorphisms were created during the cloning process.

Susceptible and R PPO plasmids were used to transform a hemG mutant strain of *E. coli*, SASX38 (Sasarman, 1979). The SASX38 *E. coli* strain was maintained on LB media supplemented with 20 μg $ml^{-1}$ hematin. Transformation-competent *E. coli* were prepared using $CaCl_2$ (Sambrook, 1989). Transformed colonies of SASX38 and non-transformed controls were tested for their ability to grow on LB media alone or supplemented with 20 μg $ml^{-1}$ hematin or with the PPO inhibitor lactofen ranging from 0.01 to 100 μM, and incubated at 37° C. for 14 hrs.

Example 12

Herbicide-Tolerant Plants by Overexpression of Plant PPO Genes

To express the herbicide resistant PPO from waterhemp in transgenic plants, the appropriate full length cDNA is inserted into a plant expression vector, desirably under the regulatory control of a plant expressible, constitutive promoter and desirably a binary vector suitable for *Agrobacterium tumefaciens*-mediated transformation of plant cells, plant tissue. The resulting plasmid is transformed into a suitable *A. tumefaciens* strain. See, e.g. Uknes et al. 1993. Plant Cell 5:159-169.

Leaf disks of *Nicotiana tabacum* cv. Xanthi-nc are infected with *A. tumefaciens* harboring the herbicide resistant PPO expression vector generally as described by Horsch et al. 1985. Science 227: 1229. Kanamycin-resistant shoots from 15 independent leaf disks are transferred to rooting medium, transplanted to soil and the resulting plants are grown to maturity in the greenhouse. Seeds from these plants are collected and germinated on MS agar medium containing kanamycin. Multiple individual kanamycin resistant seedlings from each independent primary transformant are grown to maturity in the greenhouse, and their seed collected. These seeds are germinated on MS agar medium containing kanamycin.

Plant lines that give rise to exclusively kanamycin resistant seedlings are homozygous for the inserted gene and are subjected to further analysis. Leaf disks of each of the 15 independent transgenic lines are excised with a paper punch and placed onto MS agar containing various increasing concentrations of a PPO inhibitory herbicide. After three weeks, two sets of 10 disks from each line are weighed, and the results recorded. Transgenic lines more resistant to the inhibitor than wild type (non-transformed) plants are selected for further analysis.

RNA is extracted from leaves of each of these lines. Total RNA from each independent homozygous line, and from non-transgenic control plants, is separated by agarose gel electrophoresis in the presence of formaldehyde (Ausubel et al. 1989. Current Protocols in Molecular Biology, Wiley & Sons, New York). The gel is blotted to nylon membrane (Ausubel et al., supra.) and hybridized with the radiolabeled *Arabidopsis* protox cDNA. Hybridization and washing conditions are as described by Church and Gilbert. 1984. Proc. Natl. Acad. Sci. USA 81:1991-1995. The filter is analyzed by autoradiography, and intense RNA bands corresponding to the protox transgene are detected in all herbicide-tolerant transgenic plant lines.

To further evaluate resistance of the protox-overexpressing line, plants are grown in the greenhouse and treated with various concentrations of a protox-inhibiting herbicide.

Example 13

Growth of Tobacco Cells in Suspension Culture Media

MX1 medium consists of Murashige and Skoog ("MS", T. Murashige et al. 1962. Physiol. Plant. 15:473-497) major salts, minor salts and Fe-EDTA (Gibco #500-1117; 4.3 g/l), 100 mg/l myo-inositol, 1 mg/l nicotinic acid, 1 mg/l pyridoxine-HCl, 10 mg/l thiamine—HCl, 2-3 g/l sucrose, 0.4 mg/l 2,4-dichlorophenoxyacetic acid, and 0.04 mg/l kinetin, pH 5.8. The medium is sterilized by autoclaving.

N6 medium comprises macroelements, microelements and Fe-EDTA as described by C-C. Chu et al. 1075. Scientia Sinica 18:659, and the following organic compounds: pyridoxine-HCl (0.5 mg/l), thiamine-HCl (0.1 mg/l), nicotinic acid (0.5 mg/l), glycine (2.0 mg/l), and sucrose (30.0 g/l). The solution is autoclaved. The final pH is 5.6.

Macroelements are made up as a 10× concentrated stock solution, and microelements as a 1000× concentrated stock solution. Vitamin stock solution is normally prepared 100× concentrated. Suspension cultured cells of *Nicotiana tabacum*, line S3, are grown in liquid culture medium MX1. 100 ml Erlenmeyer flasks containing 25 ml medium MX1 are inoculated with 10 ml of a cell culture previously grown for 7 days. Cells are incubated at 25° C. in the dark on an orbital shaker at 100 rpm (2 cm throw). Cells are subcultured at 7 day intervals by inoculating an aliquot sample into fresh medium, by decanting or pipetting off around 90% of the cell suspension followed by replenishing fresh medium to give the desired volume of suspension. 5-8 grams of fresh weight cell mass are produced within 10 days of growth from an inoculum of 250-350 mg cells.

Example 14

Production of Tobacco Cell Cultures Tolerant to Herbicidal PPO Inhibitors by Plating Cells on Solidified Selection Medium Cells are pregrown and harvested by allowing cells to sediment, or by brief centrifugation at 500×g, and the spent culture medium is removed. Cells are then diluted with fresh culture medium to give a cell density suitable for cell plating, about 10,000 colony forming units per ml. For plating, cells in a small volume of medium (approx. 1 ml) are evenly spread on top of solidified culture medium (MX1, 0.8% agar) containing the desired concentration of the inhibitor. About 20-30 ml of medium are used per 10 cm Petri plate. The suitable inhibitor concentration is determined from a dose-response curve, and is at least twofold higher than the $IC_{50}$ of sensitive wild-type cells. Transgenic plant cells carrying either the wild type waterhemp or the resistant waterhemp PPO are compared with respect to their properties.

Culture plates containing cells spread onto selection medium are incubated under normal growth conditions at 25-28° C. in the dark until colonies are formed. Emerging colonies are transferred to fresh medium containing the inhibitor in the desired concentration. In a modification of the described method, the pregrown suspension of cultured cells is first spread in a small volume of liquid medium on top of the solidified medium. An equal amount of warm liquid agar medium (1.2-1.6% agar) kept molten at around 40° C. is added and the plate gently but immediately swirled to spread the cells evenly over the medium surface and to mix cells and agar medium, before the medium solidifies.

Alternatively, the cells are mixed with the molten agar medium prior to spreading on top of the selection medium. This method has the advantage that the cells are embedded and immobilized in a thin layer of solidified medium on top of the selection medium. It allows for better aeration of the cells as compared to embedding cells in the whole volume of 20-30 ml.

Example 15

Production of Tobacco Cell Cultures Tolerant to an Herbicidal PPO Inhibitor by Growing Cells in Liquid Selection Medium Cells cultured as described above are inoculated at a suitable cell density into liquid medium MX1 containing the desired concentration of an herbicidal PPO inhibitor. Cells are incubated and grown as described above. Cells are subcultured, as appropriate depending on the rate of growth, using fresh medium containing the desired inhibitor concentration after a period of 7-10 days. Depending on the inhibitor concentration used, cell growth may be slower than in the absence of inhibitor.

Example 16

Production of Tobacco Cells with Enhanced Levels of PPO Enzyme

To obtain cell cultures or callus with enhanced levels of an herbicide resistant PPO of the present invention, transgenic suspension cultures or callus are transferred, in a step-wise manner, to increasingly higher concentrations of an herbicidal PPO inhibitor. In particular, the following steps are performed:

Colonies emerging from plated cells are transferred to liquid MX1 medium containing the same concentration of PPO inhibitor as used in the selection described above in order to form suspension cultures. Alternatively, selected cell suspension cultures are subcultured in liquid MX1 medium containing the same concentration of PPO inhibitor as used for selection as set forth above.

Cultures are subcultured 1-20 times at weekly intervals, and they are then subcultured into MX1 medium containing the next higher herbicide concentration. The cells are cultured for 1-10 subcultures in medium containing this higher concentration of herbicide. The cells are then transferred to MX1 medium containing the next higher concentration of herbicide.

Alternatively, pieces of selected transgenic callus are transferred to solidified MX1 medium supplemented with the desired herbicide concentration. Transfer to higher herbicide concentrations follows the procedure outlined in the preceding paragraph except that solidified medium is used.

Example 17

Herbicide Dose-Dependent Growth of Cells in Suspension Cultures

To establish a dose-response curve, the growth of cells in medium in the presence of different concentrations of herbicide is determined. Suspension culture cells of herbicidal PPO inhibitor sensitive wild-type tobacco cells S3 and herbicide tolerant transgenic cells are pregrown in liquid medium at high cell density for 2-4 days. The cells are washed free of spent medium; fresh medium without herbicide is added to give the desired cell density (about 150 mg fresh weight, FW) cells per ml of suspension). A 2.5 ml aliquot of cell suspension, containing approx. 250-300 mg fresh weight (FW) cells, is inoculated into about 30 ml of liquid medium with the desired herbicide concentration contained in a 100 ml Erlenmeyer flask. Care is taken to inoculate the same amount of cells into each flask. Each flask contains an equal volume of medium. 3-6 replicate flasks are inoculated per herbicide concentration. The herbicide concentrations are zero (=control), 0.1 ppb, 0.3 ppb, 1 ppb, 3 ppb, 10 ppb, 30 ppb, 100 ppb, 300 ppb, 1000 ppb, 3000 ppb, and 10,000 ppb. Samples of inoculum are also analyzed to determine the mass of cells inoculated per flask.

Cells are then incubated for growth under controlled conditions at 28° C. in the dark for 10 days. The cells are harvested by pouring the contents of each flask onto a filter paper disk attached to a vacuum suction device to remove all liquid and to obtain a mass of reasonably dry fresh cells. The fresh mass of cells is weighed. The dry weight of samples may be obtained after drying.

Cell growth is determined and expressed as relative cell gain within 10 days and expressed as a percentage relative to cells grown in the absence of herbicide according to the formula: (final mass of herbicide-grown cells minus inoculum mass.times.100 divided by final mass of cells grown without herbicide minus inoculum mass). $IC_{50}$ values are determined from graphs of plotted data (relative cell mass vs. herbicide concentration). $IC_{50}$ denotes the herbicide concentration at which cell growth is 50% of control growth (cells grown in the absence of herbicide).

In a modification of the method several pieces of transgenic callus derived from a herbicide resistant cell culture, obtained as described above, are transferred to solidified callus culture medium containing the different herbicide concentrations. Relative growth is determined after a culture period of 2-6 weeks by weighing callus pieces and comparing to a control culture grown in medium without herbicide. However, the suspension culture method has its greater accuracy.

Example 18

Determination of Cross Tolerance

To determine the extent at which cells show tolerance to analogous or other herbicides, cells are grown in increasing concentrations of chosen herbicides. The relative growth of the cells and their $IC_{50}$ value is determined for each herbicide for comparison.

Example 19

Determining the Stability of the Herbicide Tolerance Phenotype

To determine whether the herbicide resistant phenotype of a cell culture is maintained over time, cells are transferred from herbicide-containing medium to medium without herbicide. Cells are grown as described above in the absence of herbicide for a period of 3 months, employing regular subcultures at suitable intervals (7-10 days for suspension cultures; 3-6 weeks for callus cultures). A known quantity of cells is then transferred back to herbicide-containing medium and cultured for 10 days (suspension cultures) or 4 weeks (callus cultures). Relative growth is determined as described above.

Example 20

Production of Herbicide Resistant Corn

Ears are harvested from self pollinated corn plants of a line of corn susceptible to transformation and regeneration 12-14 days post pollination. Husks are removed, and the ears are sterilized for about 15 minutes by shaking in a 20% solution of commercial bleach (5% sodium hypochlorite) solution with detergent added for better wetting. Ears are then rinsed several times with sterile water. All further steps are performed aseptically in a sterile air flow hood. Embryos (1.5-2.5 mm in length) are removed from the kernels with a spatula and placed, embryo axis downward, onto solid MS culture medium containing 2 mg/l 2,4-dichlorophenoxyacetic acid (2,4-D), 3% sucrose, solidified with 0.24% gellan gum.

Embryogenic callus forms on the scutellum tissue of the embryos within 2-4 weeks of culture at about 28° C. in the dark. The callus is removed from the explant and transferred to fresh solidified MS medium containing 2 mg/l 2,4-D. The subculture of embryogenic callus is repeated at weekly intervals. Only callus portions having an embryogenic morphology are subcultured. The cultured callus tissue is transformed with the resistant PPO of the present invention.

Plants are regenerated from the selected embryogenic callus cultures by transferring to fresh regeneration medium. Regeneration media used are: ON6 medium consisting of N6 medium lacking 2,4-3, or N61 consisting of N6 medium containing 0.25 mg/l 2,4-D and 10 mg/l kinetin (6-furfurylaminopurine), or N62 consisting of N6 medium containing 0.1 mg/l 2,4-D and 1 mg/l kinetin, all solidified with 0.24% gellan gum. Cultures are grown at 28° C. in the light (16 h per day of 10-100 μEinsteins/$m^2$ sec from white fluorescent lamps). The cultures are subcultured every two weeks onto fresh medium. Plantlets develop within 3 to 8 weeks. Plantlets at least 2 cm tall are removed from adhering callus and transferred to root promoting medium. Different root-promoting media are used. The media consist of N6 or MS medium lacking vitamins with either the usual amount of salts or with salts reduced to one half, sucrose reduced to 1 g/l, and further either lacking growth regulating compounds or containing 0.1 mg/l α-naphthaleneacetic acid. Once roots are sufficiently developed, plantlets are transplanted to a potting mixture consisting of vermiculite, peat moss and garden soil. At transplanting all remaining callus is trimmed away, all agar is rinsed off and the leaves are clipped about half. Plantlets are grown in the greenhouse initially covered for some days with an inverted clear plastic cup to retain humidity and grown with shading. After acclimatization plants are repotted and grown to maturity. Fertilizer Peters 20-20-20 is used to ensure healthy plant development. Upon flowering plants are pollinated, preferably self pollinated.

As an alternative, the following protocol is used to produce herbicide resistant corn using a resistance gene of the present invention. *Agrobacterium* cells harboring the waterhemp herbicide resistance sequence of the present invention on a plasmid are grown in YP medium supplemented with appropriate antibiotics for 1-3 days. A loop of *Agrobacterium* cells is collected and suspended in 2 ml M-LS-002 medium (LS-inf) and the tube containing *Agrobacterium* cells is kept on a shaker for 1-3 hrs at 1,200 rpm.

Corncobs of genotype J553x(HIIIAxA188) are harvested at 7-12 days after pollination. The cobs are sterilized in a 20% Clorox solution for 15 min followed by thorough rinsing with sterile water. Immature embryos with size 0.8-2.0 mm are dissected into the tube containing *Agrobacterium* cells in LS-inf solution.

Agro-infection is carried out by keeping the tube horizontally in the laminar hood at room temperature for 30 min. The *Agrobacterium* infection mixture is poured on to a plate containing the co-cultivation medium (M-LS-011). After the liquid agro-solution is removed (using a pipette, for example), the embryos are plated on the co-cultivation medium with scutellum side up and cultured in the dark at 22° C. for 2-4 days.

Embryos are transferred to M-MS-101 medium without selection. Seven to ten days later, embryos are transferred to M-LS-401 medium containing 0.75 uM imazethapyr (or lactofen) and grown for 4 weeks to select for transformed callus cells.

Plant regeneration is initiated by transferring resistant calli to M-LS-504 medium supplemented with 0.75 μM imazethapyr (or lactofen) and grown under light at 26° C. for two to three weeks. Regenerated shoots are then transferred to a rooting box with M-MS-607 medium (0.5 μM imazethapyr or lactofen).

Plantlets with roots are transferred to potting mixture and grown in a growth chamber for a week, then transplanted to larger pots and maintained in a greenhouse till maturity.

Example 21

Production of Herbicide Tolerant Plants by Overexpression of PPO Sequences

The wild-type and the resistant waterhemp PPO coding sequences are excised by restriction endonuclease digestion and cloned into a suitable plant vector, for example, the binary vector pCIB200. These binary plasmids are transformed by electroporation into *Agrobacterium* and then into *Arabidopsis thaliana* using the vacuum infiltration method (Bechtold et al., 1993). Transformants are selected on kanamycin, and T2 seed is generated from a number of independent lines. This seed is plated on GM media containing various concentrations of PPO-inhibiting herbicide and scored for germination and survival. Multiple transgenic lines overexpressing either the wild type or the resistant mutant PPO enzyme produce significant numbers of green seedlings on an herbicide concentration that is lethal to the empty vector control.

Example 22

Production of Transgenic Herbicide Resistant *Arabidopsis*

Reverse transcription PCR (RT-PCR) products from resistant and sensitive biotypes were used as template for cloning the resistant and sensitive genes through PCR amplifications. These amplifications were performed using the ligation independent cloning (LIC) adapted oligonucleotide primers specific to PPX2L, P1 and P2, and cloned into the LIC site of a plant transformation vector, using techniques known to those skilled in the art. These primers used in these experiments were as follows: P1, TTGCTCTTCCATGGTAATTCAATCCATTAC, SEQ ID NO:49; P2, TTGCTCTTCGTTACGCGGTCTTCTCATCCATC, SEQ ID NO:50; P3, CATCGATCAAACTCGAGACCTCTGCCTCACTTTC, SEQ ID NO:51; P4, GAGGCAGAGGTCTCGAGTTTGATCGATGATCTTG, SEQ ID NO:52; P5, TTCACCAAGCTGTTTGCACATTGTGTCAACAAGTGTCT, SEQ ID NO:53; and P6, AGACACTTGTTGACACAATGTGCAAACAGCTTGGTGAA, SEQ ID NO:54. These plant transformation vectors contained an imidazolinone tolerant *Arabidopsis* AHAS large subunit gene under the control of the actin promoter and octopine synthase terminator, which allowed selection on Pursuit (imazethapyr) for all transformants, especially for selection of lactofen sensitive transformants. For expression of the resistant and sensitive genes in *Arabidopsis*, the coding sequences for each resistant or sensitive gene were inserted after the parsley ubiquitin promoter and before the nopaline synthase terminator. Several clones each of susceptible and resistant PPX2L were obtained from different biotype isolates and each was sequenced.

In addition, a chimeric "SRS" gene (see SEQ ID NO:45), which has the 5' end of the susceptible coding sequence up to the unique XhoI site, the internal XhoI to DraIII fragment of the resistant coding sequence containing the resistance mutation, and the 3' end of the susceptible from the unique DraIII site to the stop codon, was produced by amplifying sensitive RT-PCR template with P1 and P3 as well as with P6 and P2. Resistant template was also amplified with P4 and P5. These amplicons were digested with XhoI and DraIII and purified, then ligated. The ligation reaction was cloned into the LIC site of the plant transformation vector, as above.

Three vector plasmids were constructed: VC-MBW101-1, containing the susceptible version of the PPX2L gene (SEQ ID NO:47); VC-MBW102-1, containing the resistant version of the PPX2L gene (SEQ ID NO:25); and VC-MBW103-1, containing the SRS version of the PPX2L gene (SEQ ID NO:45); All three of these plasmids were transformed into *Agrobacterium tumefaciens*. as follows:

1-5 ng of the plasmid DNA isolated was transformed by electroporation into competent cells of *Agrobacterium tumefaciens*, of strain GV 3101 pMP90 (Koncz and Schell. 1986. Mol. Gen. Gent. 204:383-396). Thereafter, complete medium (YEP) was added and the mixture was transferred into a fresh reaction vessel for 3 hours at 28° C. Thereafter, all of the reaction mixture was plated onto YEP agar plates supplemented with the respective antibiotics, e.g. rifampicin (0.1 mg/ml), gentamicin (0.025 mg/ml and kanamycin (0.05 mg/ml) and incubated for 48 hours at 28° C. The agrobacterial cells containing the desired, relevant plasmid constructs were then used for the transformation of plants.

A colony was picked from the agar plate with the aid of a pipette tip and taken up in 3 ml of liquid TB medium, which also contained suitable antibiotics as described above. This preculture was grown for 48 hours at 28° C. and 120 rpm.

400 ml of LB medium containing the same antibiotics as above were used for the main culture. The preculture was transferred into the main culture. It was grown for 18 hours at 28° C. and 120 rpm. After centrifugation at 4 000 rpm, the pellet was resuspended in infiltration medium (MS medium, 10% sucrose).

In order to grow the plants for the transformation, dishes (Piki Saat 80, green, provided with a screen bottom, 30×20×4.5 cm, from Wiesauplast, Kunststofftechnik, D E) were half-filled with a GS 90 substrate (standard soil, Werkverband E. V., Germany). The dishes were watered overnight with 0.05% Proplant solution (Chimac-Apriphar, BE). *Arabidopsis thaliana* C24 seeds (Nottingham *Arabidopsis* Stock Centre, UK; NASC Stock N906) were scattered over the dish, approximately 1 000 seeds per dish. The dishes were covered with a hood and placed in the stratification facility (8 h, 110 μmol/m2/s-1, 22° C.; 16 h, dark, 6° C.). After 5 days, the dishes were placed into the short-day controlled environment chamber (8 h 130 μmol/m2/s-1, 22° C.; 16 h, dark 20° C.), where they remained for approximately 10 days until the first true leaves had formed.

The seedlings were transferred into pots containing the same substrate (Teku pots, 7 cm, LC series, manufactured by Pöppelmann GmbH & Co, Del.). Five plants were picked out into each pot. The pots were then returned into the short-day controlled environment chamber for the plant to continue growing.

After 10 days, the plants were transferred into the greenhouse cabinet (supplementary illumination, 16 h, 340 μE, 22° C.; 8 h, dark, 20° C.), where they were allowed to grow for further 17 days.

For the transformation, 6-week-old *Arabidopsis* plants, which had just started flowering were immersed for 10 seconds into the above-described agrobacterial suspension which had previously been treated with 10 μl Silwett L77 (Crompton S. A., Osi Specialties, CH). The method is described in Clough and Bent. 1998. Plant J. 16:735-743.

The plants were subsequently placed for 18 hours into a humid chamber. Thereafter, the pots were returned to the greenhouse for the plants to continue growing. The plants remained in the greenhouse for another 10 weeks until the seeds were ready for harvesting. Seeds harvested from these plants are the T1 seed generation.

These T1 generation seeds, which represented a collection of a few transformed seeds in a population of untransformed seeds, were sterilized by liquid sterilization (rinsing in a solution of 400 mL of ddH2O+100 mL of bleach+250 uL of 20% SDS, followed by rinsing in sterile distilled water).

These T1 seeds were put into 0.8% agarose and plated onto MS media with 1% sucrose, Cefotaxmine (500 ug/mL) and benomyl (2 ug/mL). For selection of transformants, these contained either 100 nM Pursuit (imazethapyr), 70 nM Cobra (lactofen) or 125 nM Cobra. *Arabidopsis* ecotype Columbia-0 (Col0) was also plated as a control on all types of plates and the imidazolinone tolerant mutant csr1-2 was plated on Pursuit plates as a positive control. The seeds were stratified on the plates for three days at 4° C.

The plates were then incubated in a Percival Scientific (Perry, Iowa) growth chamber at 21-22° C. and 15 hours of light for six days and scored for viable seedlings on the selective plates. The results are given in Table 18.

TABLE 18

Results of Plant Transformation Experiment. Seeds able to germinate on the herbicide-containing medium are those which contain and express the herbicide resistant PPX2L coding sequence.

| T1 Seed Description | Number of Seeds plated on 70 nM Lactofen | Number of Germinated Seedlings on 70 nM lactofen | Number of Seeds plated on 125 nM Lactofen | Number of Germinated Seedlings on 125 nM Lactofen | Number of Germinated Seedlings on Imazethapyr | Calculated Number of Germinated Seedlings per 1000 Seeds for both rates of Lactofen |
|---|---|---|---|---|---|---|
| Columbia-0 (untransformed control) | 884 | 0 | 600 | 0 | 0 | 0 |
| PPX2L Resistant plasmid, transformation set 1 | 640 | 4 | 560 | 4 | 9 | 7 |
| PPX2L Resistant plasmid, transformation set 2 | 1276 | 3 | 1152 | 4 | 9 | 3 |
| PPX2L Resistant plasmid, transformation set 3 | 980 | 3 | 1664 | 1 | 6 | 2 |

TABLE 18-continued

Results of Plant Transformation Experiment. Seeds able to germinate on the herbicide-containing medium are those which contain and express the herbicide resistant PPX2L coding sequence.

| T1 Seed Description | Number of Seeds plated on 70 nM Lactofen | Number of Germinated Seedlings on 70 nM lactofen | Number of Seeds plated on 125 nM Lactofen | Number of Germinated Seedlings on 125 nM Lactofen | Number of Germinated Seedlings on Imazethapyr | Calculated Number of Germinated Seedlings per 1000 Seeds for both rates of Lactofen |
|---|---|---|---|---|---|---|
| PPX2L "SRS" plasmid, transformation set 4-390 | 1176 | 14 | 1160 | 6 | 10 | 9 |
| PPX2L "SRS" plasmid, transformation set 4-414 | 1036 | 7 | 880 | 2 | 11 | 5 |
| PPX2L Susceptible plasmid, transformation set 4-291 | 500 | 0 | 680 | 0 | 4 | 0 |
| PPX2L Susceptible plasmid, transformation set 5 | 460 | 1 | 764 | 0 | 12 | 1 |

The numbers of seeds were the raw counts of actual seeds on the selection plates. The numbers of seedlings were the number of green seedlings found on each plate, indicative of resistance to the selective agent (lactofen or imazethapyr). If there were no seedlings, there were no resistant plants. Only the "resistant" forms of PPX2L conferred lactofen tolerance, confirming that the isolated PPX2L coding sequence from the herbicide resistant waterhemp was sufficient to confer the PPO-inhibiting herbicide resistance phenotype on transgenic plants into which the plant expressible sequence was introduced. The seed number for imazethapyr was not shown; rather, the seedling number from approximately 1000 seeds is indicated in the table. Plants obtained from the imazethapyr selection indicated the presence of transformed seeds with the sensitive form of PPX2L. Without wishing to be bound by any particular theory, the single seedling on transformation set 5 is believed to have been a stray resistant transformant. These data demonstrate that the resistant form of PPX2L conferred resistance to a PPO inhibiting herbicide, lactofen, to the transgenic plants expressing the resistant PPX2L.

REFERENCES CITED IN THE TEXT OF THE APPLICATION

*Arabidopsis* Genome Initiative. (2000). Analysis of the genome sequence of the flowering plant *Arabidopsis thaliana*. *Nature* 408:796-815.

Beale, S. I. and J. D. Weinstein. 1990. Tetrapyrrole metabolism in photosynthetic organisms in Biosynthesis of heme and chlorophylls (ed. by H. A. Dailey). McGraw-Hill, New York. pp. 287-391.

Bevan, M. W. (1984). Binary *Agrobacterium* vectors for plant transformation. *Nucl. Acids Res.* 12:8711-8721.

Chabregas, S. M., Luche, D. D., Farias, L. P., Ribeiro, A. F., van Sluys, M. A., Menck, C. F., and Silva-Filho, M. C. (2001). *Plant Mol. Biol.* 46:639-650.

Che, F. S., N. Wantanabe, M. Iwano, H. Inokuchi, S. Takayama, S. Yoshida, and A. Isogai. 2000. Plant Physiol. 124:59-70.

Choi K. W. et al. 1998. Biosci. Biotech. Biochem. 62:558-560.

Chow, K. S. et al. 1997. J. Biol. Chem. 272:27565-27571.

Cox, G. S. and D. G. Whitten. 1983. Excited state interactions of protoporphyrin 1× and related porphyrins with molecular oxygen in solutions and organized assemblies, in Porphyrin photosensitization (ed. by D. Kessel and T. J. Dougherty). Plenum Press, New York, N.Y.

Dayan, F. E. and S. O. Duke. 1997. Phytotoxicity of protoporphyrinogen oxidase inhibitors: phenomenology, mode of action and mechanisms of resistance, in Herbicide activity: toxicology, biochemistry and molecular biology (ed. by R. M. Roe, J. D. Burton and R. J. Kuhr) IOS Press, Amsterdam, Netherlands. pp 11-36.

Deybach, J. C. et al. 1985. Eur. J. Biochem. 149:431-435.

Doyle, J. J. and J. L. Doyle. 1990. Focus 12:13-15.

Duke, S. O. et al. 1997. Mechanisms of resistance to protoporphyrinogen oxidase-inhibiting herbicides in Weed and crop resistance to herbicides (ed. by R. De Prado, J. Jorrin, and L. Garcia-Torres). Kluwer Academic Publishers. Netherlands. pp. 155-160.

Duke, S. O., Lydon, J., Becerril, J. M., Sherman, T. D., Lehnen, L. P., & Matsumoto, H. 1991. Weed Sci. 39: 465-473.

Emanuelsson, O., H. et al. 2000. J. Mol. Biol. 300:1005-1016.

Ha, S. B., Lee, S. B., Lee, Y., Yang, K., Lee, N., Jang, S. M., Chung, J. S., Jung, S., Kim, Y. S., Wi, S. G., and Back, K. 2004. Plant Cell Environ. 27: 79-88.

Horikoshi, M. and T. Hirooka. 1999. Pestic. Sci. 24:13-16.

Horikoshi, M., K. et al. 1999. *Nicotiana tabacum* protoporphyrinogen oxidase PX-2 mRNA. GenBank Accession No. AF044129.

Jacobs, J. M. and N. J. Jacobs. 1984. Arch. Biochem. Biophys. 229:312-319.

Jacobs, J. M. and N. J. Jacobs. 1993. Plant Physiol. 101:1181-1187.

Johnson, D. J. et al. 1998. Plant Physiol. 118:330-330.

Jung, S., Lee, Y., Yang, K., Lee, S. B., Jang, S. M., Ha, S. B. and Back, K. 2004. Plant Cell Environ. 27, 1436-1446.

Kashi, Y. and King, D. G. 2006. Trends Genetics 22: 253-259.

Koch, M., C. et al. 2004. EMBO 23:1720-1728.

Kojima, S. et al. 1991. Weed Res. 36:318-323.

Lee, H. J. et al. 1993. Plant Physiol. 102:881-889.

Lee, H. J. and S. O. Duke. 1994. J. Agric. Food Chem. 42:2610-2618.
Lee, H. J. et al. 2000. Plant Cell Physiol. 41:743-749.
Lee, Y., Jung, S., & Back, K. (2004) Pestic. Biochem. Physiol. 80, 65-74.
Lermontova, I. and B. Grimm. 2000. Plant Physiol. 122:75-83.
Lermontova, I. et al. 1997. PNAS 94:8895-8900.
Li, X. and D. Nicholl. 2005. Pest Manag. Sci. 61:277-285.
Li, X. et al. 2003. Plant Physiol. 133:736-747.
Li, J., Smeda, R. J., Nelson, K. A., and Dayan, F. E. (2004) Weed Sci. 52: 333-338.
Martz, E. 2002. Trends Biochem. Sci. 27: 107-109.
Matringe, M. et al. 1992. J. Biol. Chem. 267:4646-4651.
Matsunaka, S. (1976) in Herbicides: chemistry, degradation, and mode of action, vol 2, eds. Kearney, P. C. and Kaufman D. D. (Marcel-Dekker, New York), pp. 709-739.
McCarty, D. R. 1986. Maize Genetics Coop. Newslett. 60:61.
Narita, S. et al. 1996. Gene 182:169-175.
Papenbrock, J. and B. Grimm. 2001. Planta 213:667-681.
Patzoldt, W. L. et al. 2005. Weed Sci. 53:30-36.
Patzoldt, W. L. et al. 2002. Crop Prot. 21:707-712.1.
Patzoldt, W. L., Tranel, P. J., Alexander, A. L., and Schmitzer, P. R. 2001. Weed Sci. 49: 485-490.
Pornprom, T. et al. 1994. Pestic. Biochem. Physiol. 50:107-114.
Retzlaff, K. and P. Böger. 1996. Pest. Biochem. Physiol. 54:105-114.
Sasarman, A. et al. 1993/Can. J. Microbiol. 39:1155-1161.
Sasarman, A., Chartrand, P., Lavoie, M., Tardif, D., Proschek, R. and Lapointe, C. 1979. J. Gen. Microbiol. 113: 297-303.
Seefeldt, S. S. et al. 1995. Weed Technol. 9:218-227.
Shoup, D. E. et al. 2003. Weed Sci. 51:145-150.
Shoup, D. E. and Al-Khatib, K. 2005. Weed Sci. 53: 284-289
Smith, A. G. et al. 1993. Biochem J. 292:503-508.
Stone, B. F. 1968. A formula for determining degree of dominance in cases of monofactorial inheritance of resistance to chemicals. Bull. W. H. O. 38:325-326.
Thompson, J. D., Higgins, D. G., and Gibson, T. J. 1994. Nucleic Acids Res. 22: 4673-4690.
Volrath, S. L et al. 1999. U.S. Pat. No. 5,939,602.
Watanabe, N. et al. 1998. Plant Physiol. 118:751-758.
Watanabe, N. et al. 2001. J. Biol. Chem. 276:20474-204811.
Yang, H. et al. 1996. Proc. Natl. Acad. Sci USA 93:2459-2463.

What is claimed is:

1. An isolated nucleic acid molecule comprising a coding sequence for an herbicide resistant protoporphyrinogen oxidase (PPO) wherein said PPO comprises deletion of one glycine residue corresponding to glycine-glycine at amino acids 210-211 of the PPO amino acid sequence of SEQ ID NO:16, SEQ ID NO:22 or SEQ ID NO:28, or a sequence of one of the foregoing with from one to five amino acid substitution, deletion or insertion mutations, with the proviso that enzymatic activity and herbicide resistance are maintained.

2. The nucleic acid molecule of claim 1, wherein said herbicide resistant PPO is resistant to inhibition by lactofen, (±)-2-ethoxy-1-methyl-2-oxoethyl 5-{2-chloro-4-(trifluoromethyl)phenoxy}-2-nitrobenzoate; acifluorfen, 5-{2-chloro-4-(trifluoromethyl)phenoxy}-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-{2,4-dichloro-5-(1-methylethylethoxy)phenyl}-5-(1,1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-{1-(2,3,4-trichlorophenyl)-4-nitropyrazolyl-5-oxy}propionate; M&B 39279), pyridine derivatives (e.g. LS 82-556), phenopylate and O-phenylpyrrolidino- and piperidinocarbamate analogs thereof, and 3-phenyluracils of formula I

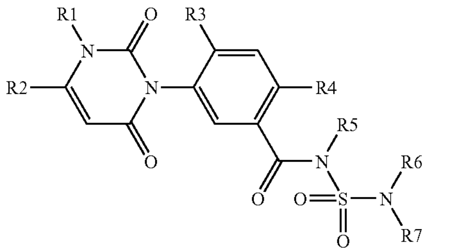

(I)

wherein $R^1$ is methyl or $NH_2$; $R^2$ is $C_1$-$C_2$-haloalkyl; $R^3$ is hydrogen or halogen; $R^4$ is halogen or cyano; $R^5$ is hydrogen, cyano, $C_1$-$C_6$-alkyl, $C_1$-$C_6$-alkoxy, $C_1$-$C_4$-alkoxy-$C_1$-$C_4$-alkyl, $C_3$-$C_7$-cycloalkyl, $C_3$-$C_6$-alkenyl, $C_3$-$C_6$-alkynyl or benzyl which is unsubstituted or substituted by halogen or alkyl; and $R^6$, $R^7$ independently of one another are hydrogen, $C_1$-$C_6$-alkyl, $C_1$-$C_6$-alkoxy, $C_3$-$C_6$-alkenyl, $C_3$-$C_6$-alkynyl, $C_3$-$C_7$-cycloalkyl, $C_3$-$C_7$-cycloalkenyl, phenyl or benzyl, where each of the 8 abovementioned substituents is unsubstituted or may be substituted by 1 to 6 halogen atoms and/or by one, two or three groups selected from: OH, $NH_2$, CN, $CONH_2$, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_1$-$C_4$-alkylamino, di($C_1$-$C_4$-alkyl)amino, formyl, $C_1$-$C_4$-alkylcarbonyl, $C_1$-$C_4$-alkoxycarbonyl, $C_1$-$C_4$-alkylaminocarbonyl, di($C_1$-$C_4$-alkyl)aminocarbonyl, $C_3$-$C_7$-cycloalkyl, phenyl and benzyl; or $R^6$, $R^7$ together with the nitrogen atom form a 3-, 4-, 5-, 6- or 7-membered saturated or unsaturated nitrogen heterocycle which may be substituted by 1 to 6 methyl groups and which may contain 1 or 2 further heteroatoms selected from the group consisting of nitrogen, oxygen and sulfur as ring members.

3. The nucleic acid molecule of claim 2, wherein said PPO comprises the amino acid sequence of SEQ ID NO:14, SEQ ID NO:26 or SEQ ID NO:30.

4. The nucleic acid molecule of claim 3, wherein said PPO comprises the amino acid sequence of SEQ ID NO:14.

5. The nucleic acid molecule of claim 3, wherein said PPO comprises the amino acid sequence of SEQ ID NO:26.

6. The nucleic acid molecule of claim 3, wherein said PPO comprises the amino acid sequence of SEQ ID NO:30.

7. The nucleic acid molecule of claim 4, wherein said herbicide resistant PPO sequence is encoded by SEQ ID NO:13 or SEQ ID NO:45.

8. The nucleic acid molecule of claim 5, wherein said PPO is encoded by SEQ ID NO:25.

9. The nucleic acid molecule of claim 6, wherein said PPO is encoded by SEQ ID NO:29.

10. The nucleic acid molecule of claim 1, further comprising a plant-expressible transcription regulatory sequence, said transcription regulatory sequence being operably linked to said coding sequence.

11. The nucleic acid molecule of claim 10, wherein said transcription regulatory sequence comprises a constitutive plant expressible promoter.

12. The nucleic acid of claim 11, wherein the plant expressible promoter is a *Arabidopsis thaliana* Act2 promoter, a Cauliflower mosaic virus 19 S promoter, a Cauliflower mosaic virus 35S promoter or a parsley ubiquitin promoter.

13. The nucleic acid of claim 1, further comprising a vector portion.

14. A method of using the nucleic acid molecule of claim 1 to produce a transgenic plant cell, transgenic plant tissue or a transgenic plant which is resistant to an herbicide which specifically inhibits protoporphyrinogen oxidase, said method comprising the steps of introducing the nucleic acid molecule of claim 1 into the plant cell, plant tissue or plant, selecting for the presence of the nucleic acid molecule to produce a transgenic plant cell or transgenic plant tissue, and optionally regenerating a plant from the transgenic plant cell or transgenic plant tissue, whereby a plant with an herbicide resistant phenotype is produced.

15. A transgenic plant containing and expressing the nucleic acid molecule of claim 1.

16. The transgenic plant of claim 15, wherein said plant is a dicotyledonous plant.

17. The transgenic plant of claim 16, wherein said plant is *Arabidopsis*, cotton, sunflower, cabbage, broccoli, cauliflower, Brussels sprout, canola, bean, pea, soybean, citrus, tomato, potato, sweet potato, plum, peach, apple, pear, cherry, grape, rose, tobacco, alfalfa, trefoil, sugar beet, blackberry, raspberry, blueberry, marionberry, loganberry, apricot, eggplant, pepper, pumpkin, squash, gourd, an ornamental plant, aspen, poplar, maple, oak, sunflower, rose or tobacco.

18. The transgenic plant of claim 15, wherein said plant is a monocotyledonous plant.

19. The transgenic plant of claim 18, wherein said plant is wheat, corn, rice, sorghum, oat, wild rice, barley, millet or grass.

20. The transgenic plant of claim 19, wherein said plant is corn.

21. The transgenic progeny plant of the plant of any of claims 15 to 20.

22. Transgenic seed containing within its genetic complement the nucleic acid molecule of claim 1.

23. A method of controlling weeds comprising the step of planting transgenic plants comprising the nucleic acid molecule of claim 1; and treating the plants with a PPO-inhibiting herbicide to which resistance is conferred by said molecule, whereby growth of weeds is controlled.

24. A method of selecting a transgenic plant cell containing and expressing the nucleic acid of claim 1, said method comprising the steps of growing said plant cell on medium comprising an amount of an inhibitor of porphoryinogen oxidase sufficient to prevent growth of a corresponding plant cell which does not contain and express said nucleic acid molecule.

25. An isolated protoporphyrinogen oxidase protein resistant to a PPO-inhbiting herbicide identified by the sequence given in SEQ ID NO:14, SEQ ID NO:26 or SEQ ID NO:30, or a sequence of the foregoing with from one to five amino acid substitutions, deletion or insertion mutations, provided that there is no insertion of a glycine residue after amino acid 210 of SEQ ID NO:14, SEQ ID NO:26 or SEQ ID NO:30.

26. The protoporphyrinogen oxidase of claim 25, wherein said protein consists of the sequence selected from the group consisting of SEQ ID NO:14, SEQ ID NO:26 and SEQ ID NO:30.

* * * * *